United States Patent
Tsou et al.

(10) Patent No.: US 11,851,435 B2
(45) Date of Patent: Dec. 26, 2023

(54) PTGR2 INHIBITORS AND THEIR USE

(71) Applicants: National Health Research Institutes, Miaoli County (TW); National Taiwan University, Taipei (TW)

(72) Inventors: Lun Kelvin Tsou, Miaoli County (TW); Ming-Shiu Hung, Miaoli County (TW); Chieh Wen Chen, Miaoli County (TW); Meng-Lun Hsieh, Taipei (TW); Yi-Cheng Chang, Taipei (TW); Lee Ming Chuang, Taipei (TW)

(73) Assignees: National Health Research Institutes, Miaoli County (TW); National Taiwan University, Taipei (TW)

( * ) Notice: Subject to any disclaimer, the term of this patent is extended or adjusted under 35 U.S.C. 154(b) by 0 days.

(21) Appl. No.: 17/688,369

(22) Filed: Mar. 7, 2022

(65) Prior Publication Data

US 2023/0279008 A1  Sep. 7, 2023

(51) Int. Cl.
C07D 487/04 (2006.01)
C07D 239/56 (2006.01)
C07D 417/12 (2006.01)

(52) U.S. Cl.
CPC ......... C07D 487/04 (2013.01); C07D 239/56 (2013.01); C07D 417/12 (2013.01)

(58) Field of Classification Search
CPC .............................. C07D 239/56; C07D 417/12
See application file for complete search history.

(56) References Cited

U.S. PATENT DOCUMENTS

| 8,759,357 B2 | 6/2014 | Shipps, Jr. et al. | |
| 2017/0158680 A1* | 6/2017 | Jiang | C07D 417/12 |

FOREIGN PATENT DOCUMENTS

WO    WO-2010/056631 A1    5/2010

OTHER PUBLICATIONS

Synthesis of novel S-acyl and S-alkylpyrimidinone derivatives as potential cytotoxic agents Makaram M. Said • Azza T. Taher Hala B. El-Nassan • Eman A. El-Khouly Res Chem Intermed (2016) 42:6643-6662 DOI 10.1007/s11164-016-2487-x.*

Discovery of Cdc25A Lead Inhibitors with a Novel Chemotype by Virtual Screening: Application of Pharmacophore Modeling Based on a Training Set with a Limited Number of Unique Components Yu-Shu Ge et al. ChemMedChem 2017, 12, 438-447, DOI: 10.1002/cmdc.201600644.*

Synthesis of novel S-acyl and S-alkylpyrimidinone derivatives as potential cytotoxic agents Makaram M. Said • Azza T. Taher Hala B. El-Nassan • Eman A. El-Khouly Res Chem Intermed (2016) 42:6643-6662 DOI 10.1007/s11164-016-2487-x (Year: 2016).*

Discovery of Cdc25A Lead Inhibitors with a Novel Chemotype by Virtual Screening: Application of Pharmacophore Modeling Based on a Training Set with a Limited Number of Unique Components Yu-Shu Ge et al. ChemMedChem 2017, 12, 438-447, DOI: 10.1002/cmdc.201600644 (Year: 2017).*

Lan et al "Small-Molecule Inhibitors of FABP4/5 Ameliorate Dyslipidemia But Not Insulin Resistance in Mice With Diet-Induced Obesity" Journal of Lipid Research vol. 52, pp. 646-656, 2011.

Parker et al "Ligand and Target Discovery by Fragment-Based Screening in Human Cells" Cell vol. 168, pp. 527-541, 2017.

Tseng et al "Increasing Endogenous PPARγ Ligands Improves Insulin Sensitivity and Protects Against Diet-Induced Obesity Without Side Effects of Thiazolidinediones" http://www.researchsquare.com/article/rs-490889/v1, 2021.

Wang et al "The Natural Product Essramycin and Three of its Isomers are Devoid of Antibacterial Activity" Journal of Natural Products vol. 79, pp. 1219-1222, 2016.

\* cited by examiner

*Primary Examiner* — Jeffrey S Lundgren
*Assistant Examiner* — Eric Tran
(74) *Attorney, Agent, or Firm* — Morse, Barnes-Brown & Pendleton, P.C.; Martin Z. Zhang, Esq.

(57) ABSTRACT

Disclosed are compounds of formula (I) as follows:

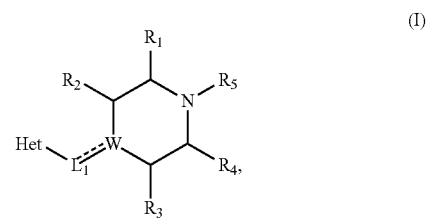

in which each of $R_1$, $R_2$, $R_3$, $R_4$, $R_5$, $L_1$, W, and Het is defined herein. Also provides are a method of inhibiting prostaglandin reductase 2 ("PTGR2") using such a compound and a pharmaceutical composition containing same.

22 Claims, 3 Drawing Sheets

PTGR2 INHIBITORS AND THEIR USE

BACKGROUND

More than thirty million Americans have type 2 diabetes, caused by insulin resistance in which the body does not respond correctly to insulin to move blood sugar into cells for energy storage.

Insulin sensitivity can be improved by activating peroxisome proliferator-activated receptor γ ("PPARγ"), a ligand-inducible transcriptional regulator of systemic and energy balance. PPARγ thus serves a target for treating type 2 diabetes. See Ahmadian et al., *Nat. Med.* 19, 557-66 (2013). Indeed, thiazolidinediones were developed as a PPARγ activator with robust insulin sensitizing activities. However, it imparts undesirable side effects including weight gain, fluid retention, and osteoporosis. See Soccio et al., *Cell Metab.* 20, 573-91 (2014).

Polyunsaturated fatty acid 15-keto-prostaglandin E2 ("15-keto-PGE2"), a natural endogenous ligand derived from prostaglandin E2 ("PGE2"), can activate PPARγ, thereby improving insulin sensitivity and also preventing diet-induced obesity. Unfortunately, 15-keto-PGE2 is rapidly reduced by prostaglandin reductase 2 ("PTGR2") to an inactive metabolite in the body. See Chou et al., *J. Biol. Chem.* 282, 18162-72 (2007). Inhibiting PTGR2 would preserve 15-keto-PGE2 and maintain its level in the body to boost insulin sensitivity.

There is a need to develop PTGR2 inhibitors for treating diabetes through PPARγ activation.

SUMMARY

The present invention is based on an unexpected discovery that certain compounds are effective PTGR2 inhibitors, suitable for treating diabetes.

In one aspect, this invention relates to a compound of formula (I):

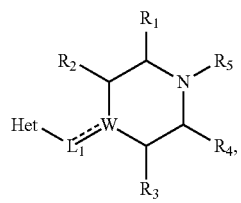

(I)

in which each of $R_1$, $R_2$, $R_3$, and $R_4$, independently, is H, halo, $C_{1-16}$ alkyl, $C_{1-16}$ alkoxy, or $R_2$ and $R_4$ together is a $C_{1-16}$ alkyl; $R_5$ is $C_{1-16}$ alkyl, $C_{3-10}$ cycloalkyl, $C_{1-10}$ heterocycloalkyl, aryl, heteroaryl, $C_{7-10}$ aralkyl, $C_{1-10}$ heteroaralkyl, $C(O)CH_2SR_6$, or $C(O)OR_7$, $R_6$ being $C_{1-10}$ heterocycloalkyl and $R_7$ being $C_{1-16}$ alkyl or $C_{7-10}$ aralkyl; W is N or CH; $L_1$ is $C_{1-6}$ alkyl, $C_{3-10}$ cycloalkyl, S—$CR_8R_9$—C(O), S—$CR_8R_9$—$CR_{10}R_{11}$, S—$CR_8R_9$—C(O)—NH, or S—$CR_8R_9$—$CR_{10}R_{11}$—C(O), each of $R_8$, $R_9$, $R_{10}$, and $R_{11}$, independently, being H or $C_{1-6}$ alkyl; Het is $C_{1-10}$ heterocyclyl; $=\!=\!=$ is a single or double bond; and each of $C_{1-6}$ alkyl, $C_{3-10}$ cycloalkyl, $C_{1-10}$ heterocycloalkyl, aryl, heteroaryl, $C_{7-10}$ aralkyl, $C_{1-10}$ heteroaralkyl, and heterocyclyl is optionally substituted with one or more of the chemical groups consisting of hydroxyl, halo, nitro, cyano, amino, $C_{1-6}$ alkyl, $C_{1-6}$ alkoxyl, $C_{3-10}$ cycloalkyl, aralkyl, and heteroaryl.

Compounds of formula (I) have one or more the following preferred features: (i) each of $R_1$, $R_2$, $R_3$, and $R_4$, independently, is H or methyl, or $R_2$ and $R_4$ together is methyl and each of $R_1$ and $R_3$ is H; (ii) $R_5$ is phenyl, chlorophenyl, dichlorophenyl, fluorophenyl, difluorophenyl, hydroxylphenyl, methylphenyl, dimethylphenyl, trifluoromethylphenyl, methoxyphenyl, ethoxyphenyl, phenylmethoxy, benzyl, thiazolyl, benzo[d]isothiazolyl, pyridinyl, trifluoromethylpyridinyl, benzo[d][1,3]dioxolyl, pyrimidinyl, methoxypyrimidinyl, dimethoxypyrimidinyl, trifluoromethylpyrimidinyl, chlorotrifluoromethylpyridinyl, methoxyethyl, phenylethyl, or cyclohexyl; (iii) each of $R_1$, $R_2$, $R_3$, and $R_4$ is H; (iv) $R_5$ is phenyl; (v) W is N and $=\!=\!=$ is a single bond; (vi) $L_1$ is $CH_2$, $CH(CH_3)$, $SCH_2C(O)$, $SCH_2CH_2C(O)$, $NHCH_2C(O)$, $SCH(CH_3)C(O)$, $SCH(C_3H_7)C(O)$, or $SCH_2C(CH_3)_2C(O)$; (vii) Het is

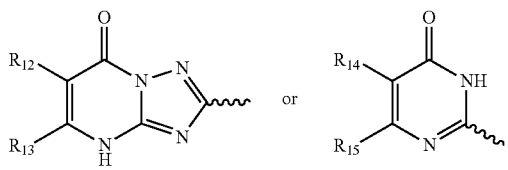

each of $R_{12}$, $R_{13}$, $R_{14}$, and $R_{15}$, independently, being hydroxyl, halo, nitro, cyano, amino, $C_{1-6}$ alkyl, $C_{1-6}$ alkoxyl, $C_{3-10}$ cycloalkyl, aralkyl, or heteroaryl; (viii) $L_1$ is $CH(CH_3)$ and Het is

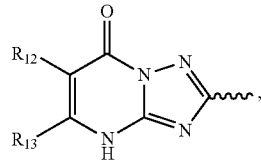

each of $R_{12}$ and $R_{13}$, independently, being halo, $C_{1-6}$ alkyl, $C_{1-6}$ alkoxyl, $C_{3-10}$ cycloalkyl, or aralkyl.

A subset of compounds of formula (I) are the compounds of formula (II):

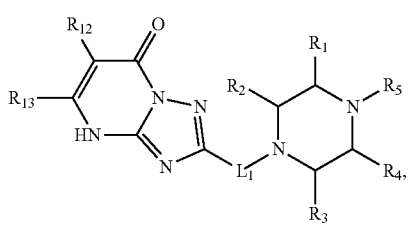

(II)

in which each of $R_1$, $R_2$, $R_3$, $R_4$, $R_5$, $R_{12}$, $R_{13}$, and $L_1$ is defined above.

Certain compounds of formula (II) contain one or more of features (i)-(iii) as described above. More preferably, $R_{12}$ is benzyl optionally substituted with one or more halo, $R_{13}$ is methyl, and $L_1$ is $CH(CH_3)$.

Another subset of compounds of formula (I) are the compounds of formula (III):

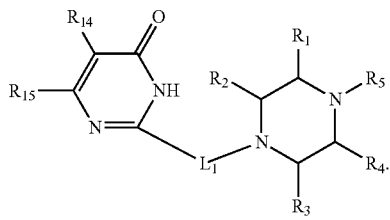

(III)

Each of $R_1$, $R_2$, $R_3$, $R_4$, $R_5$, $R_{14}$, $R_{15}$, and $L_1$ is defined above. Preferred features include: (i) each of $R_1$, $R_2$, $R_3$, and $R_4$ is H or methyl; (ii) $R_5$ is aryl or heteroaryl; (iii) each of $R_{14}$ and $R_{15}$, independently, is H, $C_{1-6}$ alkyl, or $C_{3-10}$ cycloalkyl; and (iv) $L_1$ is $SCH_2C(O)$, $SCH_2CH_2C(O)$, $NHCH_2C(O)$, $SCH(CH_3)C(O)$, $SCH(C_3H_7)C(O)$, or $SCH_2C(CH_3)_2C(O)$.

Table 1 below shows 72 exemplary compounds of formula (I) of this invention, i.e., Compounds 1-72, together with their structures.

TABLE 1

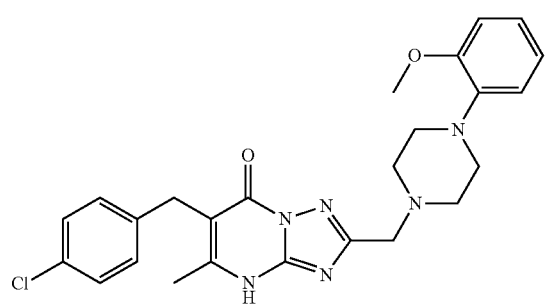 [SMILES: COc1ccccc1N1CCN(Cc2nc3[nH]c(C)c(Cc4ccc(Cl)cc4)c(=O)n3n2)CC1]

Compound 1

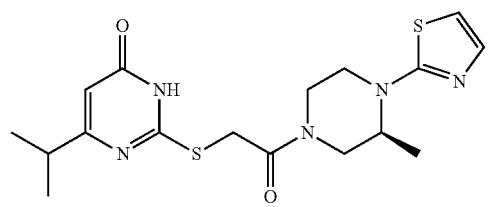 [SMILES: CC(C)c1cc(=O)[nH]c(SCC(=O)N2CCN(c3nccs3)[C@@H](C)C2)n1]

Compound 2

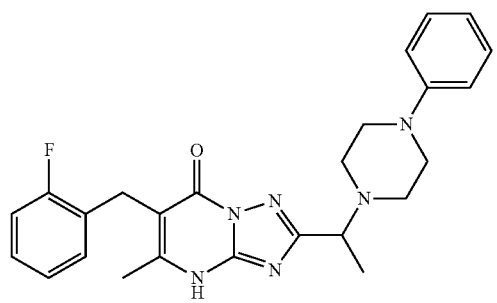 [SMILES: Cc1[nH]c2nc(C(C)N3CCN(c4ccccc4)CC3)nn2c(=O)c1Cc1ccccc1F]

Compound 3

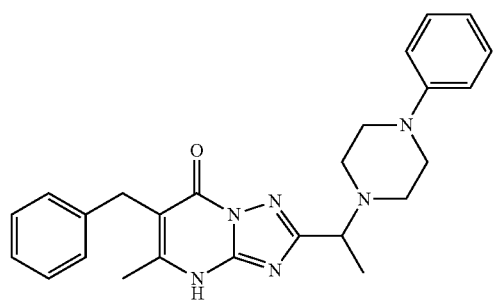 [SMILES: Cc1[nH]c2nc(C(C)N3CCN(c4ccccc4)CC3)nn2c(=O)c1Cc1ccccc1]

Compound 4

TABLE 1-continued
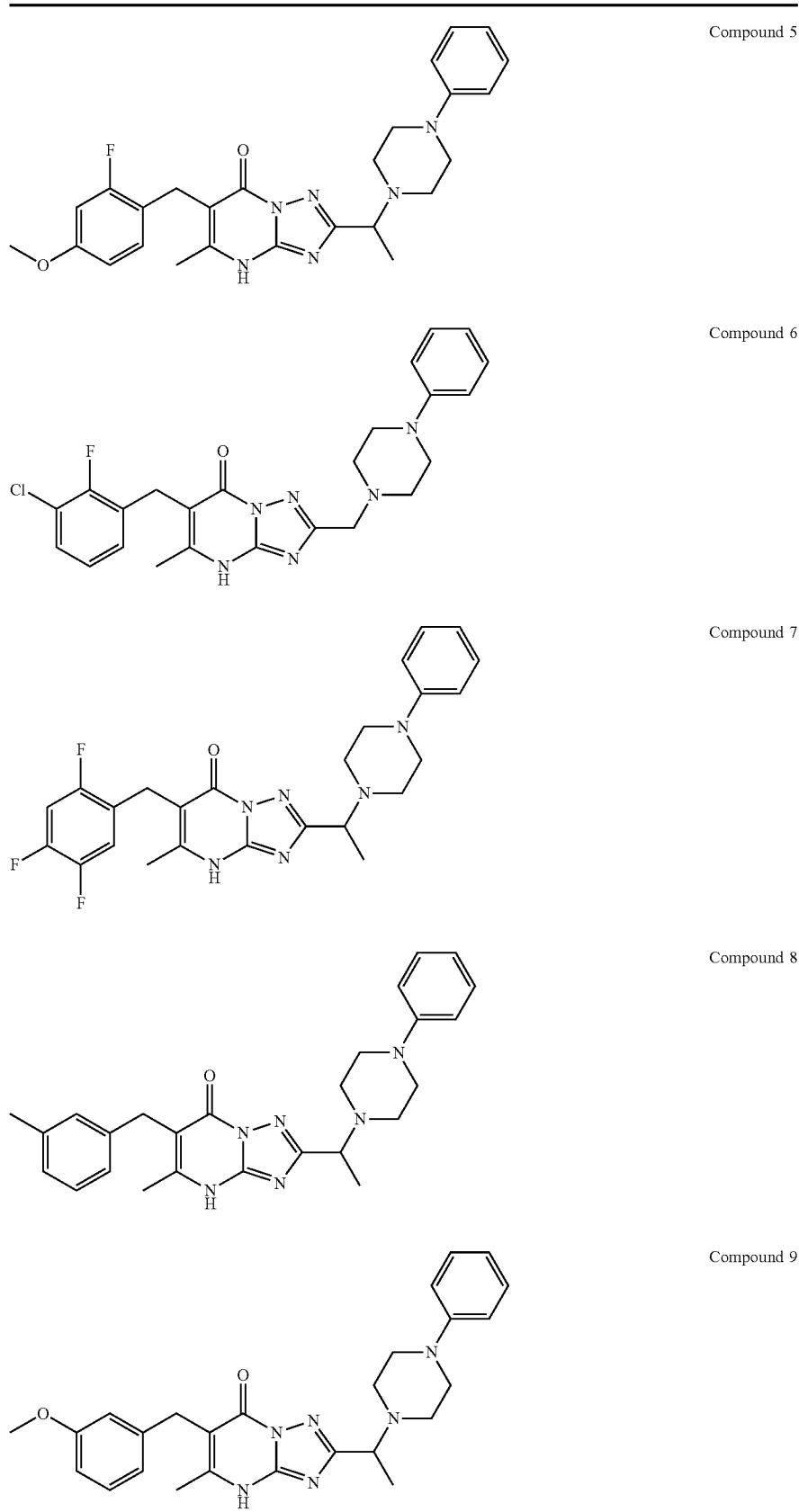
Compound 5
Compound 6
Compound 7
Compound 8
Compound 9

TABLE 1-continued
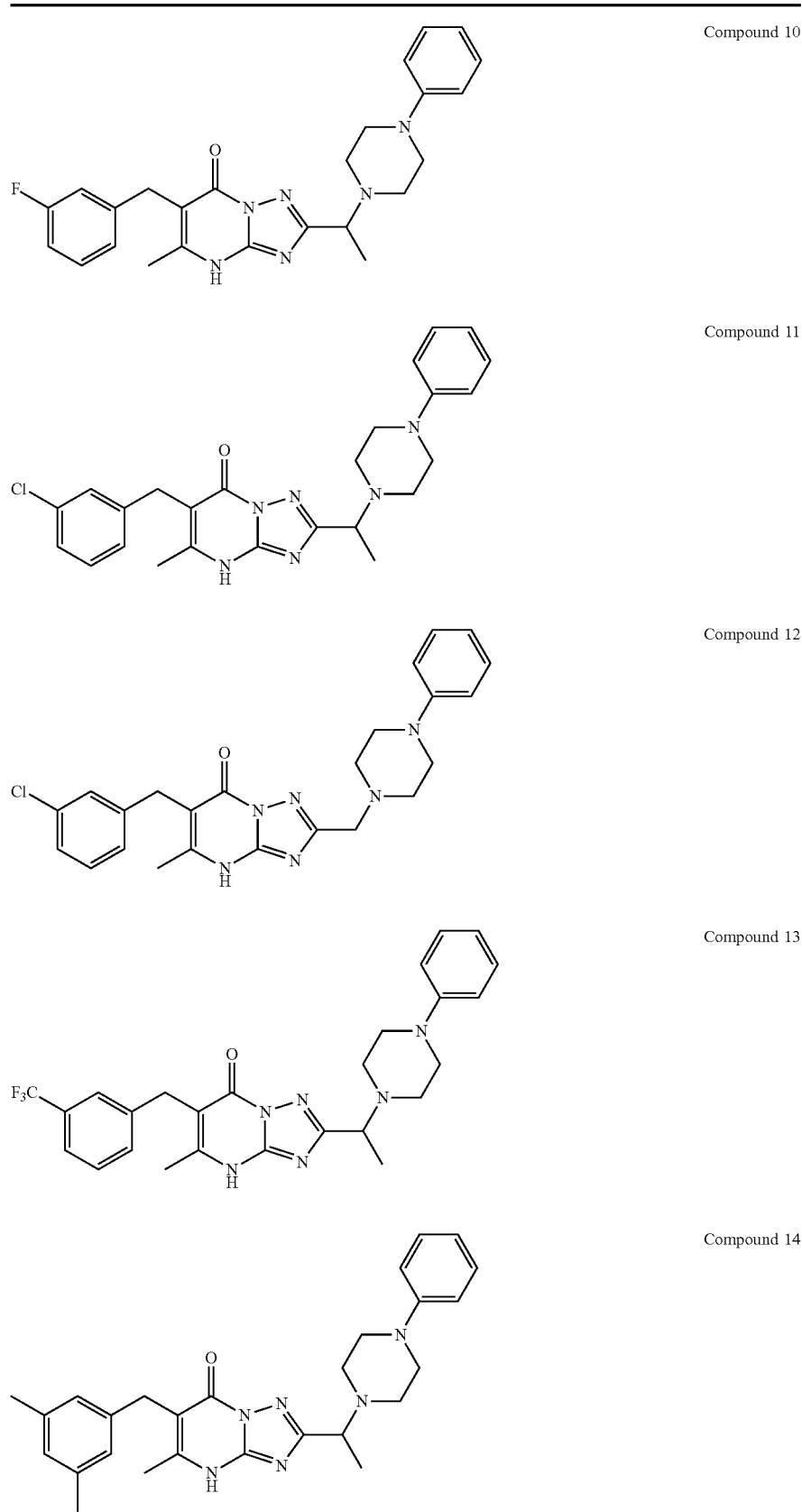
Compound 10
Compound 11
Compound 12
Compound 13
Compound 14

TABLE 1-continued
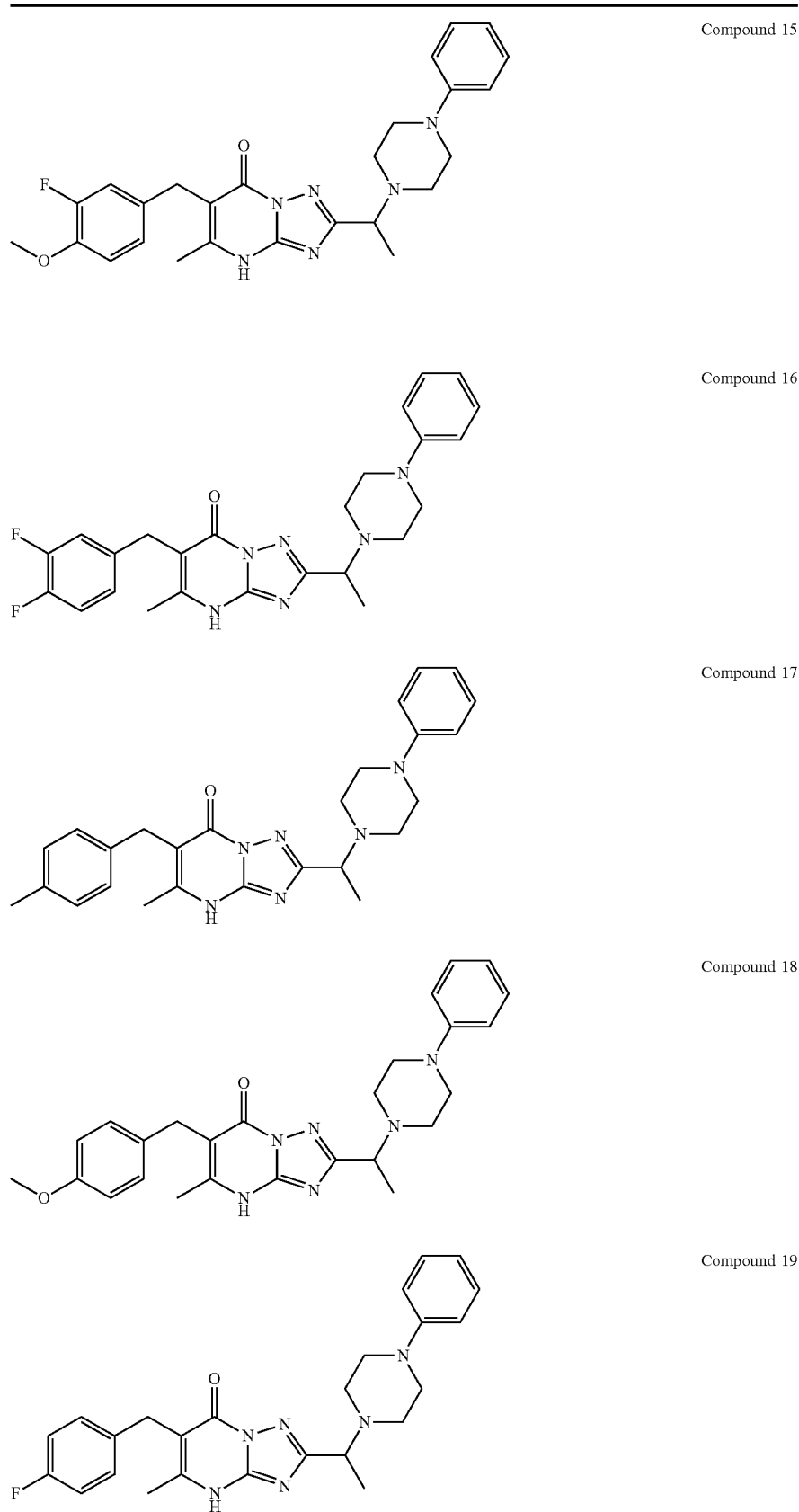
Compound 15
Compound 16
Compound 17
Compound 18
Compound 19

TABLE 1-continued
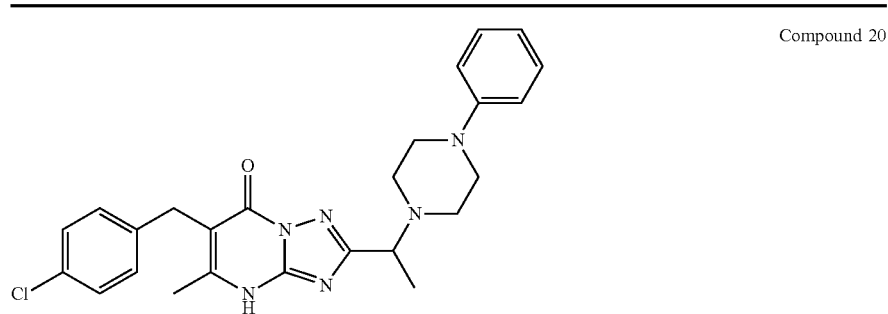
Compound 20
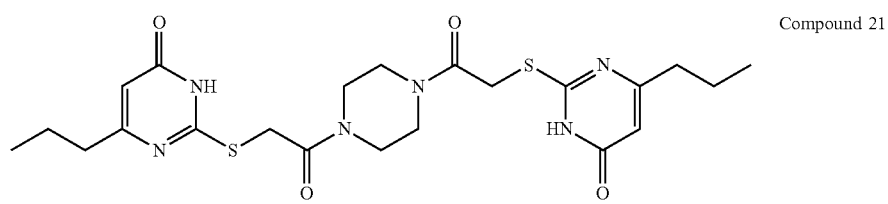
Compound 21
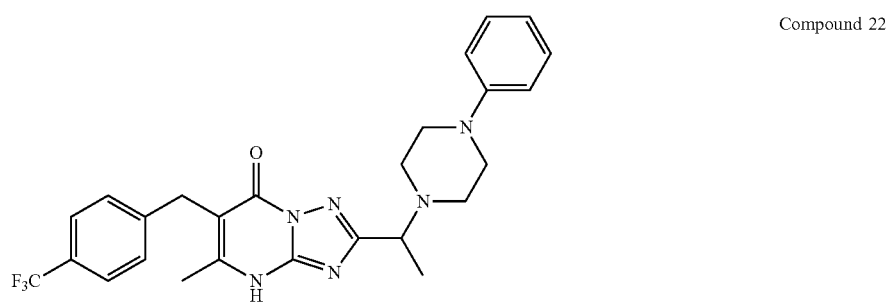
Compound 22
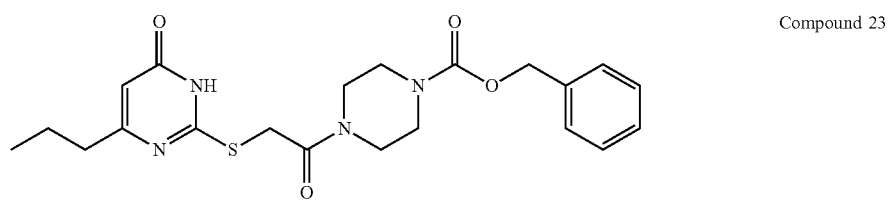
Compound 23
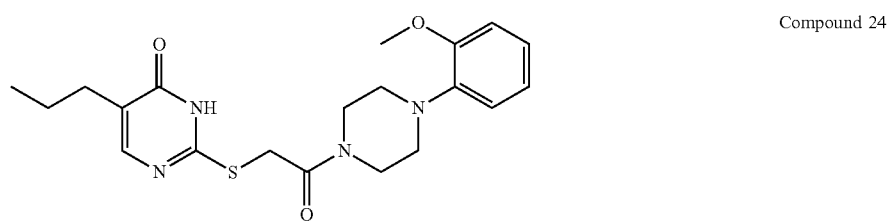
Compound 24
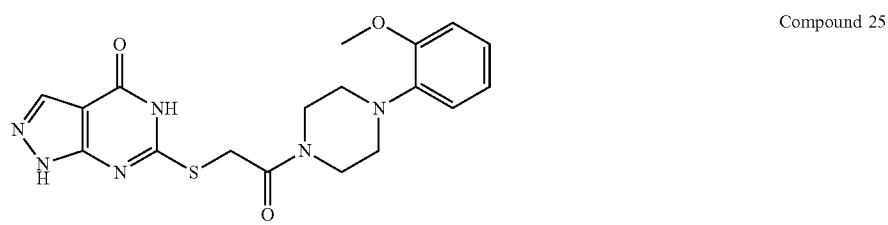
Compound 25

TABLE 1-continued
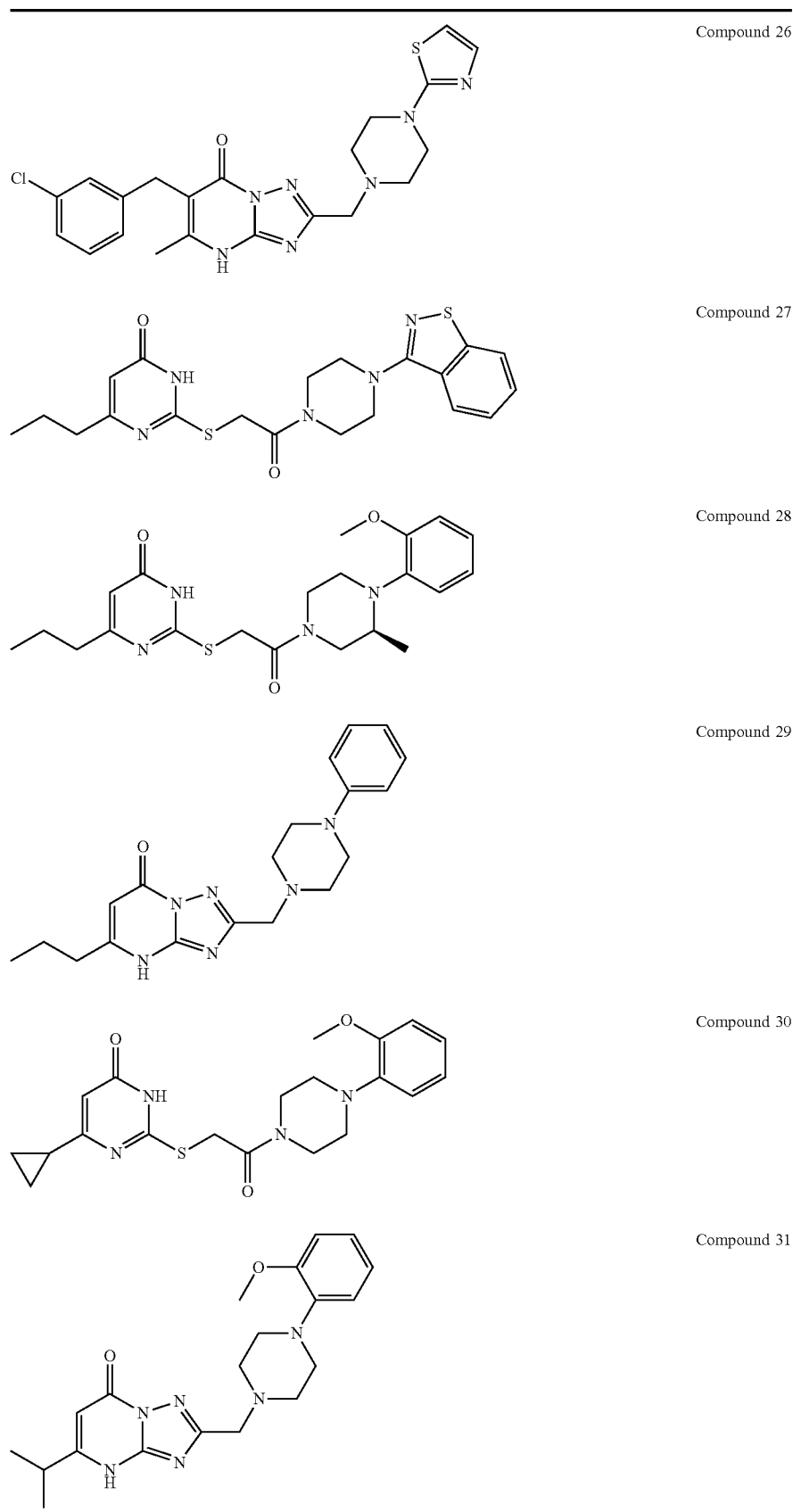
Compound 26
Compound 27
Compound 28
Compound 29
Compound 30
Compound 31

TABLE 1-continued
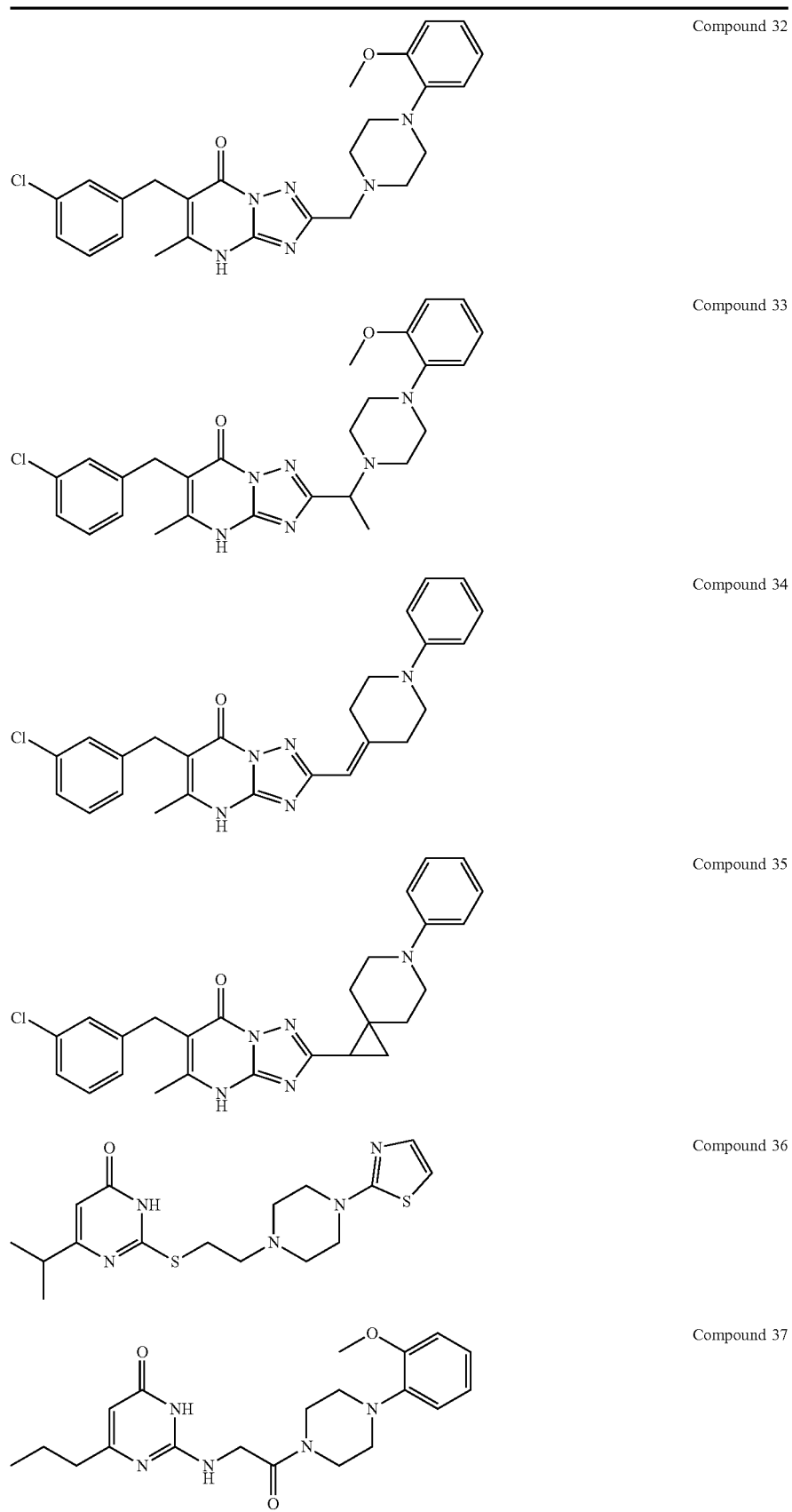
Compound 32
Compound 33
Compound 34
Compound 35
Compound 36
Compound 37

TABLE 1-continued
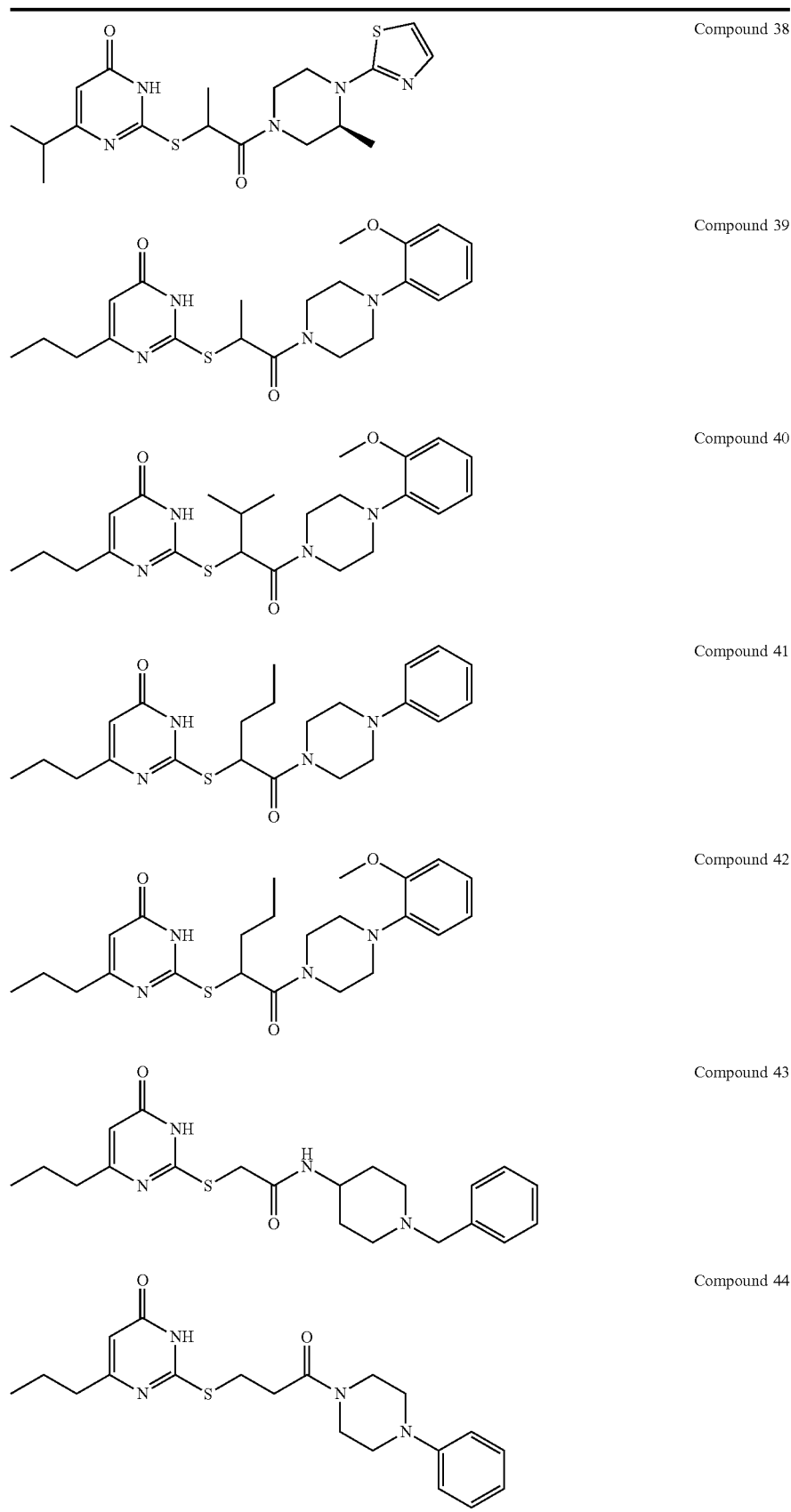
Compound 38
Compound 39
Compound 40
Compound 41
Compound 42
Compound 43
Compound 44

TABLE 1-continued
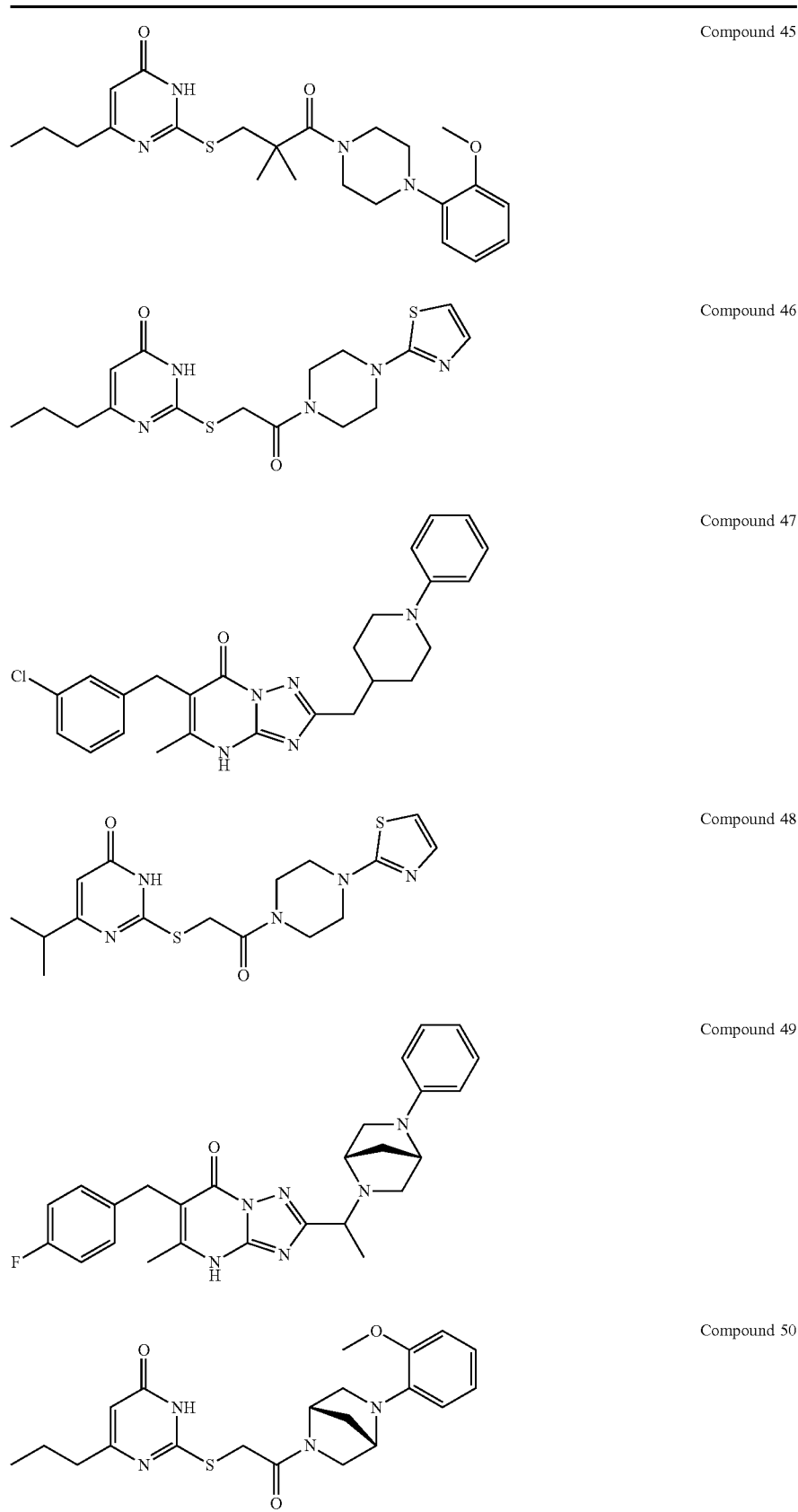
Compound 45
Compound 46
Compound 47
Compound 48
Compound 49
Compound 50

TABLE 1-continued
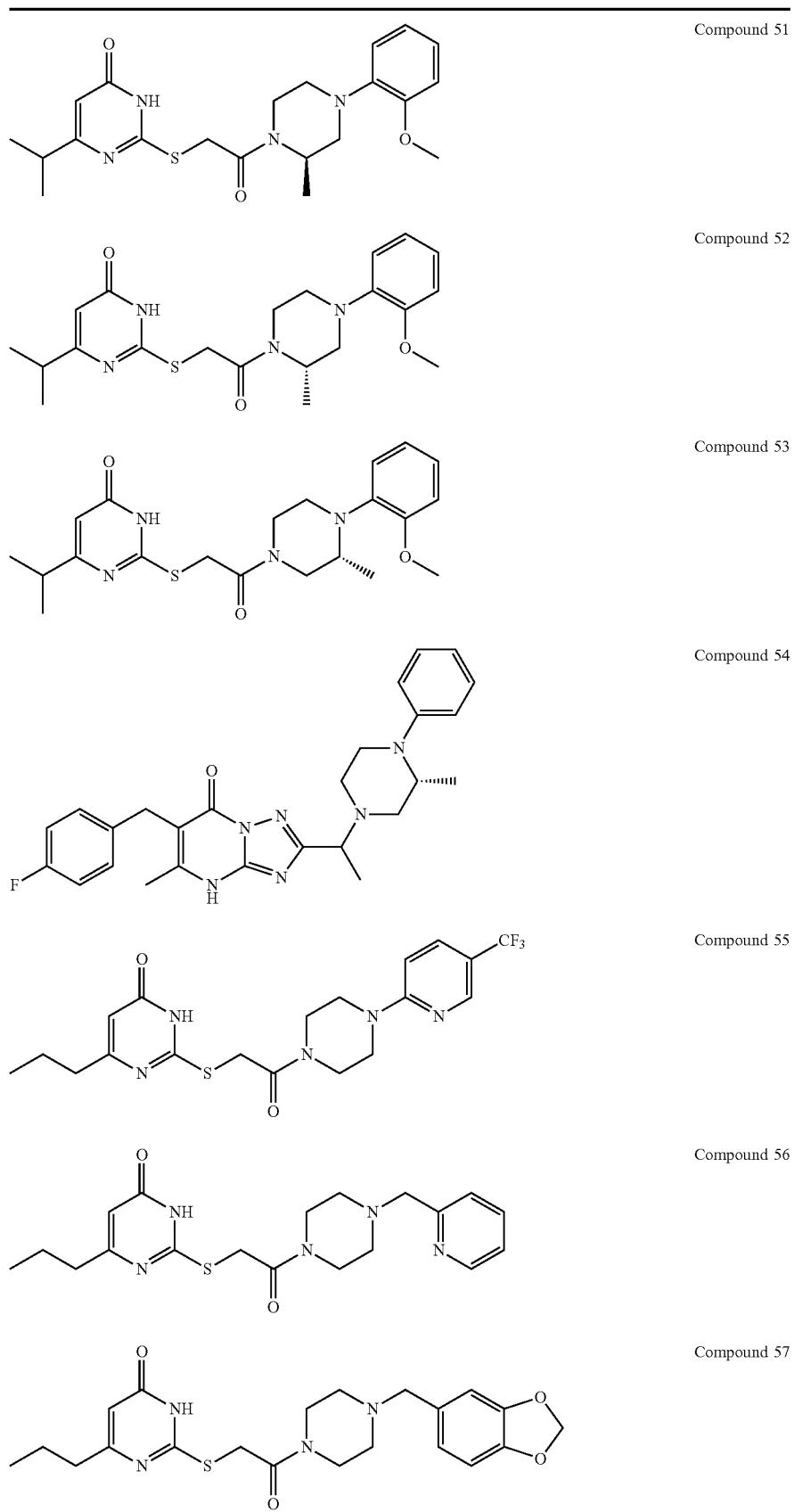
Compound 51
Compound 52
Compound 53
Compound 54
Compound 55
Compound 56
Compound 57

TABLE 1-continued
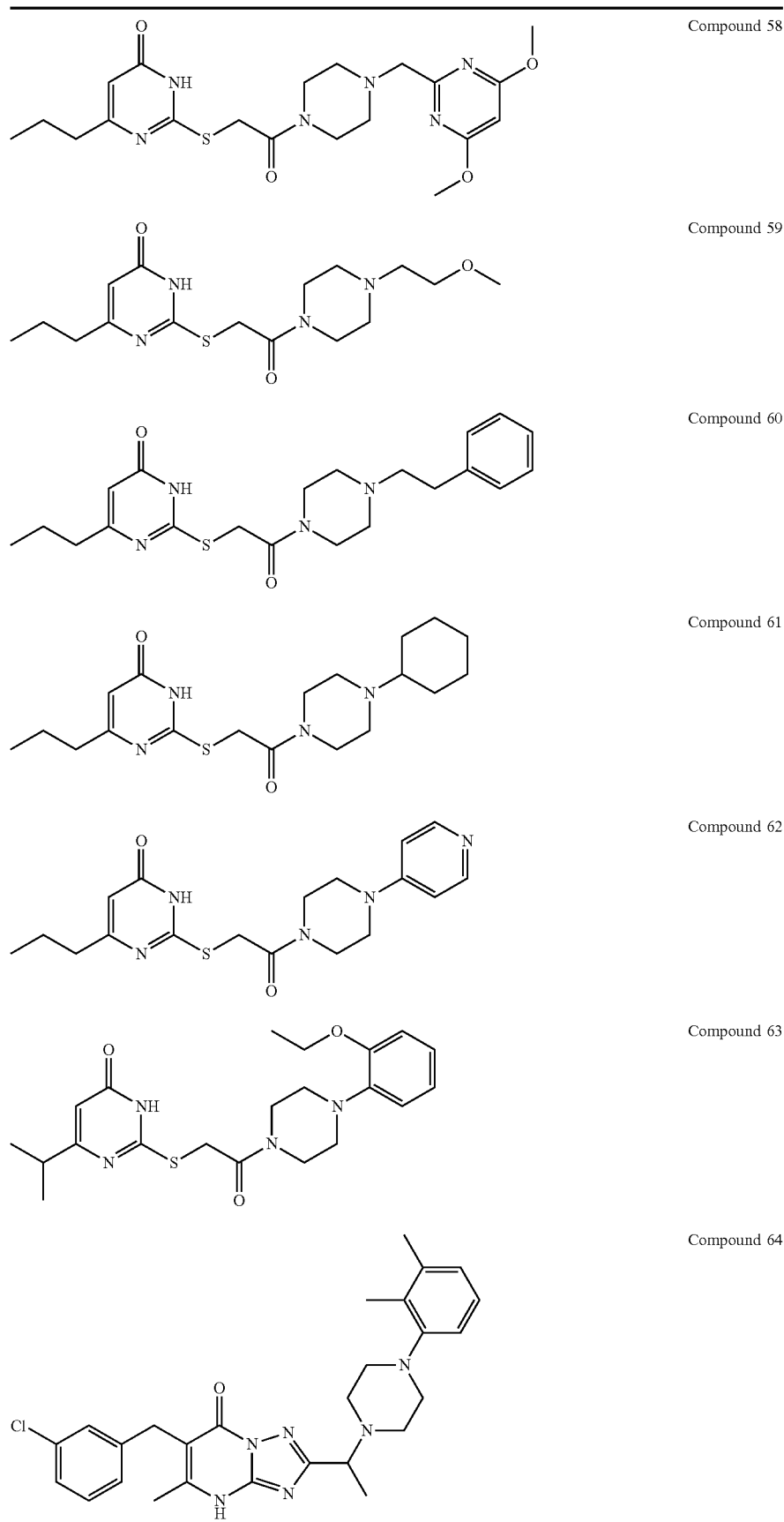
| | |
|---|---|
| | Compound 58 |
| | Compound 59 |
| | Compound 60 |
| | Compound 61 |
| | Compound 62 |
| | Compound 63 |
| | Compound 64 |

TABLE 1-continued
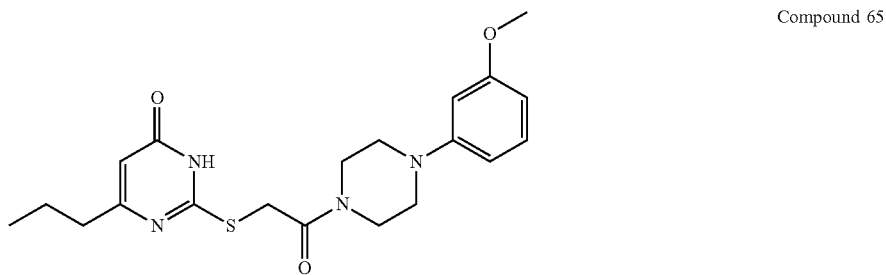
Compound 65
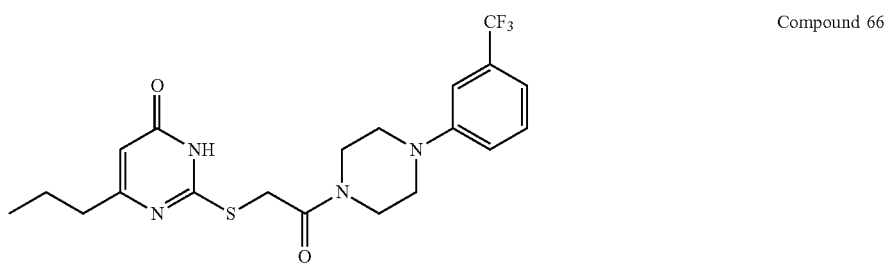
Compound 66
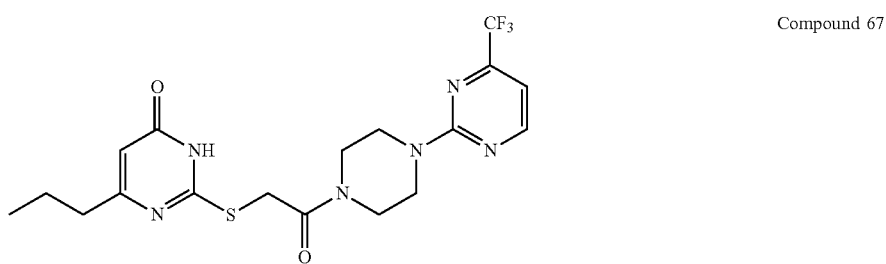
Compound 67
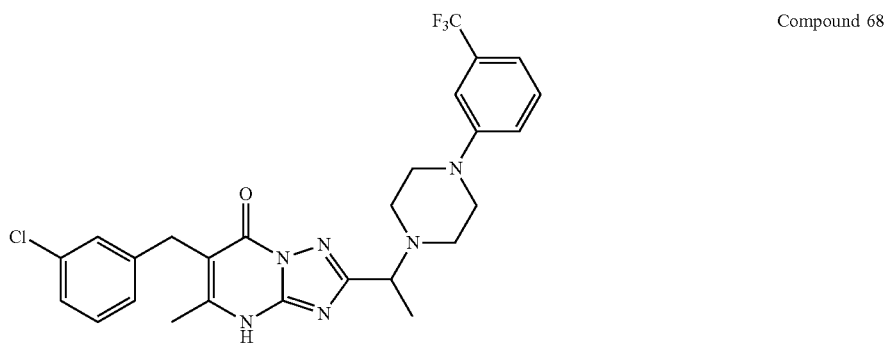
Compound 68
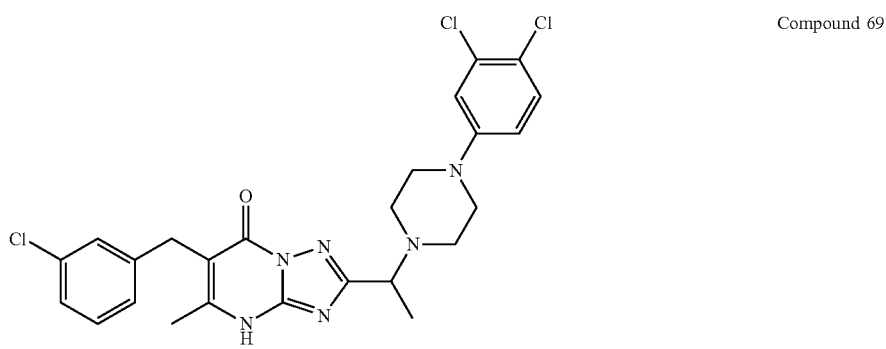
Compound 69

TABLE 1-continued

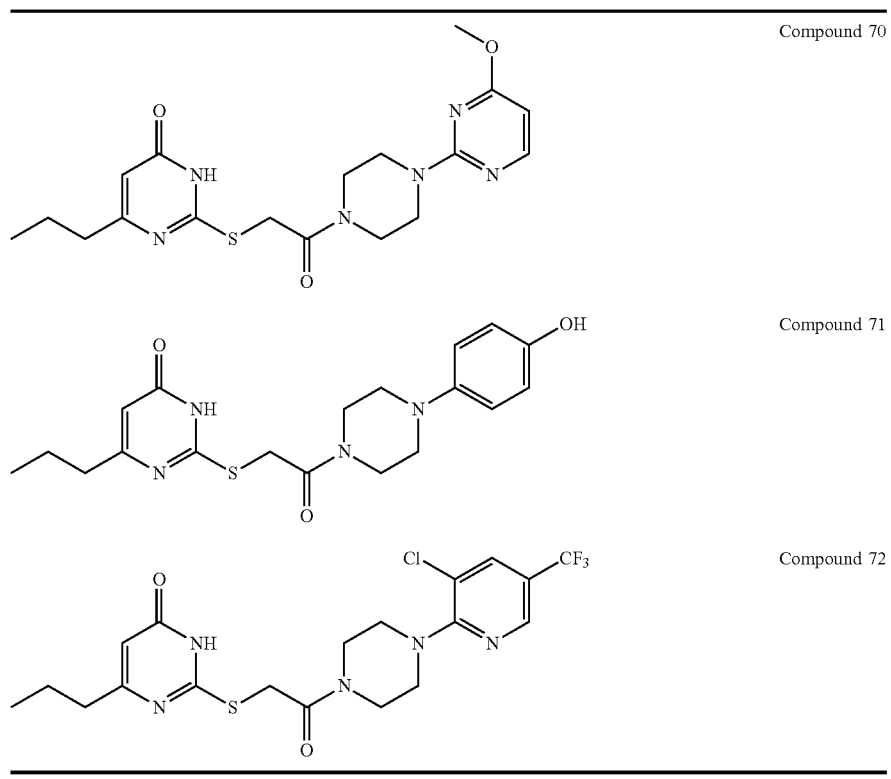

Compound 70

Compound 71

Compound 72

Preferred compounds include Compound 3, Compound 7, Compound 10, Compound 16, and Compound 19.

Also within the scope of this invention is a method of inhibiting prostaglandin reductase 2 ("PTGR2") by administering to a subject in need thereof an effective amount of any one of the compounds described above.

Still within the scope of this invention are pharmaceutical compositions containing any one of the above-described compounds and a pharmaceutically acceptable carrier thereof.

The term "alkyl" herein refers to a straight or branched hydrocarbon group, containing 1-20 (e.g., 1-10 and 1-6) carbon atoms. Exemplary alkyl groups are methyl ("Me"), ethyl ("Et"), n-propyl, iso-propyl, n-butyl, iso-butyl, and tert-butyl. Alkyl includes its halo substituted derivatives, i.e., haloalkyl, which refers to alkyl substituted with one or more halogen (chloro, fluoro, bromo, or iodo) atoms. Examples include trifluoromethyl, bromomethyl, and 4,4,4-trifluorobutyl. The term "alkoxy" refers to an —O-alkyl group (e.g., methoxy, ethoxy, propoxy, and isopropoxy). Alkoxy includes haloalkoxy, namely, alkoxy substituted with one or more halogen atoms, e.g., —O—$CH_2$Cl and —O—$CHClCH_2$Cl.

The term "cycloalkyl" refers to a saturated and partially unsaturated monocyclic, bicyclic, tricyclic, or tetracyclic hydrocarbon group having 3 to 12 carbons (e.g., $C_{3-10}$). Examples are cyclopropyl, cyclobutyl, cyclopentyl, cyclopentenyl, cyclohexyl, cyclohexenyl, cycloheptyl, and cyclooctyl. The term "cycloalkyloxy" refers to an —O—cycloalkyl group, e.g., cyclohexyloxy. Cycloalkyloxy includes halocycloalkyloxy, referring to cycloalkyloxy substituted with one or more halogen atoms.

The term "heterocycloalkyl" refers to a nonaromatic 3-8 membered monocyclic, 8-12 membered bicyclic, or 11-14 membered tricyclic ring system having one or more heteroatoms (e.g., O, N, P, and S). Examples of heterocycloalkyl groups include piperazinyl, piperidinyl, imidazolidinyl, azepanyl, pyrrolidinyl, dihydrothiadiazolyl, dioxanyl, morpholinyl, tetrahydropuranyl, and tetrahydrofuranyl. The term "heterocycloalkyloxy" refers to an —O-heterocycloalkyloxy. Each of hetercycloalkyl and heterocycloalkyloxy include its halogenated versions, i.e., those having one or more substitutions of halogen atoms.

The term "aryl" refers to a 6-carbon monocyclic, 10-carbon bicyclic, 14-carbon tricyclic aromatic ring system wherein each ring can have 1 to 5 substituents. Examples include phenyl, naphthyl, and anthracenyl. The term "aralkyl" refers to alkyl substituted with an aryl group. The term "aryloxy" refers to an —O-aryl group, e.g., phenoxy.

The term "heteroaryl" refers to an aromatic 5-8 membered monocyclic, 8-12 membered bicyclic, or 11-14 membered tricyclic ring system having one or more heteroatoms (e.g., O, N, P, and S). Examples include triazolyl, oxazolyl, thiadiazolyl, tetrazolyl, oxazolyl, isoxazolyl, pyrazolyl, pyridyl, carbazolyl, tetrahydropyranyl, furyl, imidazolyl, benzimidazolyl, pyrimidinyl, thienyl, quinolinyl, indolyl, thiazolyl, and benzothiazolyl. The term "heteroaryl alkyl" refers to an alkyl group substituted with a heteroaryl group. The term "heteroaryloxy" refers to an —O-heteroaryl group. The term "heterocyclyl" refers to heterocycloalkyl and heteroaryl.

The terms "halo" refers to a fluoro, chloro, bromo, or iodo radical. The term "amino" refers to a radical derived from amine, which is unsubstituted or mono-/di-substituted with alkyl, aryl, cycloalkyl, heterocycloalkyl, or heteroaryl. The term "alkylamino" refers to alkyl-NH—. The term "dialkylamino" refers to alkyl-N(alkyl)-.

Alkyl, cycloalkyl, heterocycloalkyl, aryl, heteroaryl, aralkyl, heteroaralkyl, alkoxy, and aryloxy mentioned herein include both substituted and unsubstituted moieties.

Examples of a substituent include halo, hydroxyl, amino, cyano, nitro, mercapto, alkoxycarbonyl, amido, carboxy, alkanesulfonyl, alkylcarbonyl, carbamido, carbamyl, carboxyl, thioureido, thiocyanato, sulfonamido, alkyl, alkenyl, alkynyl, alkyloxy, aryl, heteroaryl, cycloalkyl, and heterocycloalkyl, in which alkyl, alkenyl, alkynyl, alkyloxy, aryl, heteroaryl, cycloalkyl, and heterocycloalkyl may further substituted.

The term "compound", when referring to a compound of formula (I), also includes its salts, solvates, and prodrugs. A salt can be formed between an anion and a positively charged group (e.g., amino) on a compound. Examples of a suitable anion are chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. A salt can also be formed between a cation and a negatively charged group. Suitable cations include sodium ion, potassium ion, magnesium ion, calcium ion, and ammonium cation such as tetramethyl-ammonium ion. Further, a salt can contain quaternary nitrogen atoms. A solvate refers to a complex formed between an active compound and a pharmaceutically acceptable solvent. Examples of a pharmaceutically acceptable solvent include water, ethanol, isopropanol, ethyl acetate, acetic acid, and ethanolamine. A prodrug refers to a compound that, after administration, is metabolized into a pharmaceutically active drug. Examples of a prodrug include esters and other pharmaceutically acceptable derivatives.

The compounds may contain one or more non-aromatic double bonds or asymmetric centers. Each of them occurs as a racemate or a racemic mixture, a single R enantiomer, a single S enantiomer, an individual diastereomer, a diastereometric mixture, a cis-isomer, or a trans-isomer. Compounds of such isomeric forms are within the scope of this invention. They can be present as a mixture or can be isolated using chiral synthesis or chiral separation technologies.

This invention also features use of one or more of the above-described compounds of formula (I) for the manufacture of a medicament for treating and preventing diabetes or obesity.

The term "treating" or "treatment" refers to administering one or more of the compounds to a subject, who suffers from diabetes or obesity, or has a predisposition toward one of them, with the purpose to confer a therapeutic effect, e.g., to cure, relieve, alter, affect, ameliorate, or prevent diabetes or obesity, symptoms, or the predisposition. "An effective amount" refers to the amount of a compound that is required to confer the therapeutic effect. Effective doses will vary, as recognized by those skilled in the art, depending on the types of symptoms treated, route of administration, excipient usage, and the possibility of co-usage with other therapeutic treatment.

To practice the method of the present invention, a composition having one or more of the above-described compounds can be administered parenterally, orally, nasally, rectally, topically, or buccally.

The term "parenteral" as used herein refers to subcutaneous, intracutaneous, intravenous, intraperitoneal, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or di-glycerides). Fatty acid, such as oleic acid and its glyceride derivatives, are useful in the preparation of injectables, as are natural pharmaceutically acceptable oils, such as olive oil and castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens and Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents.

A composition having one or more of the above-described compounds can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active compound. Examples include colloidal silicon oxide, magnesium stearate, cellulose, sodium lauryl sulfate, and D&C Yellow #10.

The details of one or more embodiments of the invention are set forth in the description below. Other features, objects, and advantages of the invention will be apparent from the description and from the claims.

DETAILED DESCRIPTION

Figure 1:
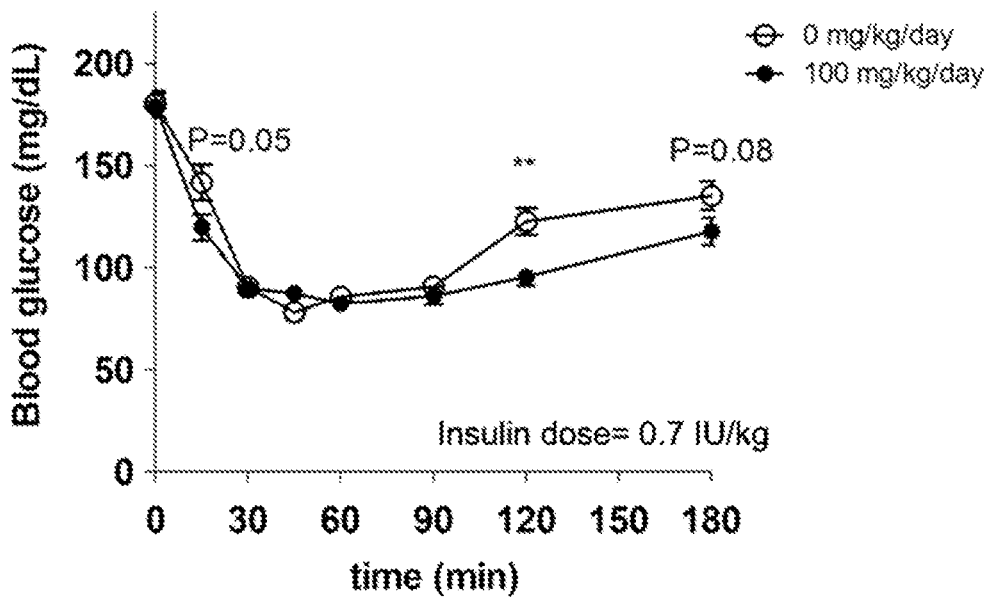
FIG. 1 shows animal blood glucose levels in a study of an insulin tolerance test ("ITT") at a 0.7 IU/kg insulin level, comparing the blood glucose levels in two groups of mice treated with: (i) 100 mg/kg/day of compound 3 dissolved in an aqueous solution containing 3% dimethylacetamide and 10% cremophor and (ii) an aqueous solution containing 3% dimethylacetamide and 10% cremophor as a vehicle control.

Described in detail below are compounds of formula (I) reproduced below, as well as their syntheses and their use in treating diabetes and obesity or inhibiting prostaglandin reductase 2 ("PTGR2").

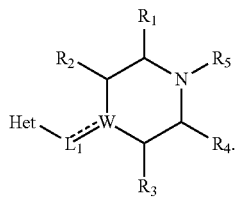

(I)

The present invention is based on a surprising discovery that the compounds of formula (I) are effective in modulating PTGR2's enzymatic and cellular activities, preventing diet-induced obesity, lowering fasting plasma glucose, improving glucose tolerance and insulin sensitivity. In vivo studies have demonstrated their efficacy in treating obesity and decreasing insulin-resistance.

The compounds of formula (I) can be prepared by synthetic methods well known in the art. See, e.g., R. Larock, Comprehensive Organic Transformations ($3^{rd}$ Ed., John Wiley and Sons 2018); P. G. M. Wuts and T. W. Greene, Greene's Protective Groups in Organic Synthesis ($4^{th}$ Ed., John Wiley and Sons 2007); L. Fieser and M. Fieser, Fieser and Fieser's Reagents for Organic Synthesis (John Wiley and Sons 1994); and L. Paquette, ed., Encyclopedia of Reagents for Organic Synthesis ($2^{nd}$ ed., John Wiley and Sons 2009) and subsequent editions thereof.

The compounds thus prepared can be purified following conventional methods such as crystallization, distillation/vacuum distillation, flash chromatography over silica, and preparative liquid chromatography.

Importantly, compounds of this invention can be initially screened using an in vitro method to identify PTGR2 inhibition activity.

The compounds of this invention are effective PTGR2 inhibitors as shown in examples below. They are useful in treating diabetes and obesity.

A compound of this invention is preferably formulated into a pharmaceutical composition containing a pharmaceutical carrier. The pharmaceutical composition is then given to a subject in need thereof to inhibit PTGR2 thus treating diabetes or obesity.

Without further elaboration, it is believed that one skilled in the art can, based on the above description, utilize the present invention to its fullest extent. The following examples are to be construed as merely illustrative and not limitative of the remainder of the disclosure in any way whatsoever. All publications cited herein are hereby incorporated by reference in their entirety.

Set forth below are examples illustrating preparation and efficacy evaluation of compounds of this invention.

Unless otherwise mentioned, all chemicals are commercially available from Sigma-Aldrich (St. Louis, Missouri).

Example 1: 6-(4-chlorobenzyl)-2-((4-(2-methoxyphenyl)piperazin-1-yl)methyl)-5-methyl-[1,2,4]triazolo[1,5-a]pyrimidin-7(4H)-one (Compound 1)

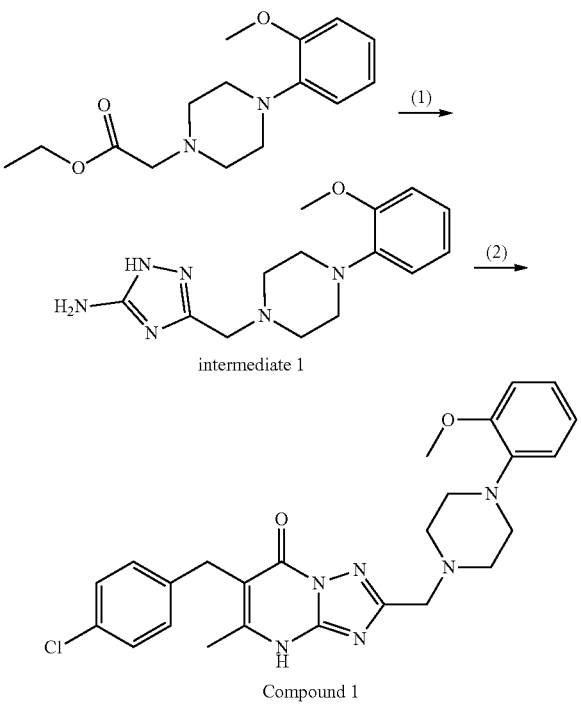

Reagents and conditions: (1) aminoguanidine bicarbonate, n-butyl alcohol, refluxing, 40 hours, yield 37%, and (2) ethyl 2-(4-chlorobenzyl)-3-oxobutanoate, acetic acid, refluxing, 16 hours, yield 39%.

Step 1

Aminoguanidine bicarbonate (341.6 mg, 2.51 mmol) and ethyl 2-(4-(2-methoxyphenyl) piperazin-1-yl)acetate (700 mg, 2.51 mmol) were dissolved in 1.5 mL n-butanol and heated at reflux for 40 hours. After removing the solvent, the reaction mixture was purified by column chromatography to give intermediate 1 as a yellow solid (266.9 mg, 37%).

$^1$H NMR (300 MHz, d$^6$-DMSO) δ 6.99-6.78 (m, 4H), 5.74 (s, 2H), 3.75 (s, 3H), 3.37 (s, 2H), 2.97-2.87 (m, 4H), 2.61-2.51 (m, 4H).

ESI-MS $C_{14}H_{20}N_6O$: 289.1 (M+H$^+$)$^+$ and 311.2 (M+Na$^+$)$^+$.

Step 2

Intermediate 1 (100 mg, 0.35 mmol) and ethyl 2-(4-chlorobenzyl)-3-oxobutanoate (89.1 mg, 0.35 mmol) were dissolved in 1 mL acetic acid and heated at reflux for 16 hours. After removing the solvent, the reaction mixture was neutralized by saturated sodium bicarbonate solution and then extracted by dicholoromethane. The resultant organic layers were collected, dried over MgSO$_4$, filtered, and concentrated to afford a crude, which was purified by column chromatography to obtain Compound 1 as a yellow oil (65.5 mg, 39%).

$^1$H NMR (300 MHz, CDCl$_3$): δ 7.18 (s, 4H), 7.01 (td, J=7.6, 1.7 Hz, 1H), 6.91 (dd, J=7.6, 1.7 Hz, 1H), 6.85 (dd, J=7.6, 1.7 Hz, 1H), 6.84 (td, J=7.6, 1.7 Hz, 1H), 3.93 (s, 2H), 3.84 (s, 3H), 3.82 (s, 2H), 3.06-3.00 (m, 4H), 2.83-2.74 (m, 4H), 2.53 (s, 3H).

ESI-MS $C_{25}H_{27}ClN_6O_2$: 479.2 (M+H$^+$)$^+$, 501.2 (M+Na$^+$)$^+$.

Example 2: (S)-6-isopropyl-2-((2-(3-methyl-4-(thiazol-2-yl)piperazin-1-yl)-2-oxoethyl)thio)pyrimidin-4(3H)-one (Compound 2)

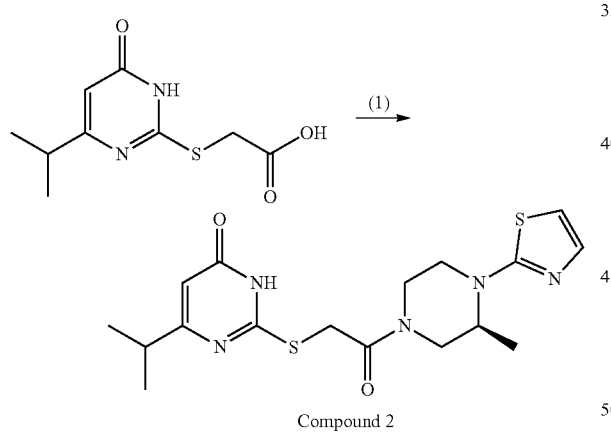

Compound 2

2-((4-Isopropyl-6-oxo-1,6-dihydropyrimidin-2-yl)thio) acetic acid (62 mg, 0.27 mmol), (S)-2-(2-methylpiperazin-1-yl)thiazole (49.5 mg, 0.27 mmol), 1-ethyl-3-(3-dimethyl-aminopropyl)carbodiimide ("EDC", 57 mg, 0.29 mmol) and 4-dimethylaminopyridine ("DMAP", 6 mg, 0.05 mmol) were dissolved in 2 mL diemthylformamide ("DMF"). The resultant mixture was stirred at room temperature for 16 hours, and then extracted with H$_2$O and CH$_2$Cl$_2$. The organic layer was collected, dried over MgSO$_4$, filtered, and concentrated to afford a crude, which was purified by column chromatography (5% MeOH in CH$_2$Cl$_2$ as eluent) to obtain Compound 2 as a white solid (67 mg, 63%).

$^1$H NMR (400 MHz, CDCl$_3$): δ 12.23 (s, 1H), 7.22 (d, J=3.6 Hz, 0.5H), 7.20 (d, J=3.6 Hz, 0.5H), 6.61 (d, J=3.6 Hz, 1H), 6.06 (d, J=2.1 Hz, 1H), 4.70-4.61 (m, 0.5H), 4.51-4.36 (m, 1H), 4.18 (s, 2H), 4.27-4.06 (m, 0.5H), 4.03-3.76 (m, 1.5H), 3.71-3.56 (m, 1H), 3.52-3.26 (m, 1.5H), 3.12 (dd, J=13.4, 4.0 Hz, 0.5H), 2.95 (td, J=12.7, 4.1 Hz, 0.5H), 2.77-2.63 (m, 1H), 1.29 (d, J=6.7 Hz, 1.5H), 1.21 (d, J=6.7 Hz, 1.5H), 1.19 (d, J=6.8 Hz, 6H).

ESI-MS $C_{17}H_{23}N_5O_2S_2$: 393.1, found: 394.1 (M+H$^+$)$^+$, 416.0 (M+Na$^+$)$^+$.

Example 3: 6-(2-fluorobenzyl)-5-methyl-2-(1-(4-phenylpiperazin-1-yl)ethyl)-[1,2,4]triazolo[1,5-a]pyrimidin-7(4H)-one (Compound 3)

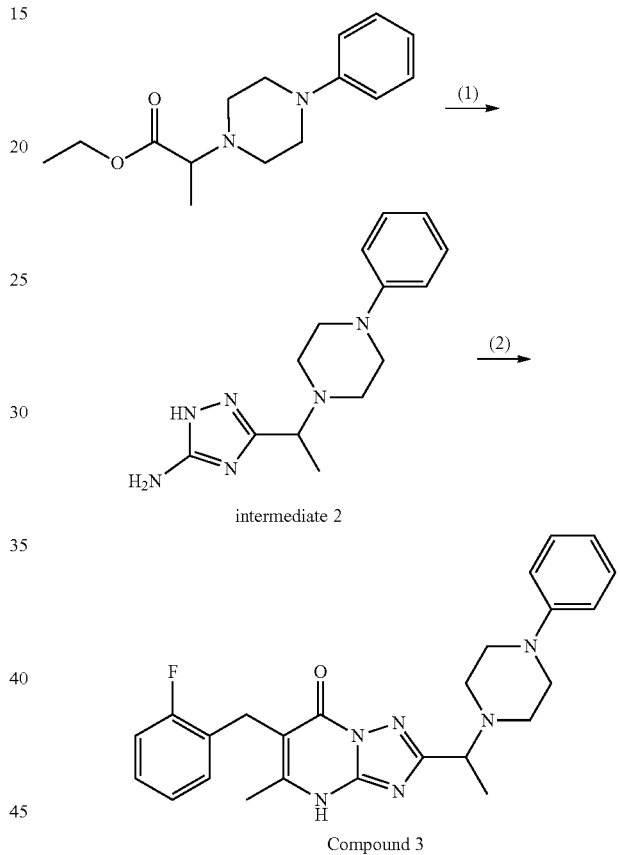

Compound 3

Reagents and conditions: (1) aminoguanidine bicarbonate, DMF, 140° C., 16 h, and yield 27% and (2) 2-(2-fluoro-benzyl)-3-oxo-butyric acid ethyl ester, toluene, reflux by Dean-Stark, 16 h, and yield and yield 34%.

Step 1

Aminoguanidine bicarbonate (2.2 g, 1.61 mmol) and 2-(4-phenyl-piperazin-1-yl)-propionic acid ethyl ester (2 g, 0.81 mmol) were dissolved in 6 mL DMF and heated at 140° C. for 16 hours. After removing the solvent, the reaction mixture was purified by column chromatography to obtain intermediate 2 as a white solid (600 mg, 27%).

$^1$H NMR (300 MHz, d$^6$-DMSO): δ 11.75 (s, 1H), 7.18 (t, J=9.0 Hz, 2H), 6.89 (d, J=9.0 Hz, 2H), 6.75 (t, J=9.0 Hz, 1H), 5.83 (s, 2H), 3.66-3.51 (m, 1H), 3.15-3.02 (m, 4H), 2.64-2.51 (m, 4H), 1.31 (d, J=6.9 Hz, 3H).

ESI-MS $C_{14}H_{20}N_6$: 272.2, found: 273.1 (M+H$^+$)$^+$, 295.1 (M+Na$^+$)$^+$.

Step 2

Intermediate 2 (150 mg, 0.55 mmol) and 2-(2-fluorobenzyl)-3-oxo-butyric acid ethyl ester (157.7 mg, 0.66 mmol) were dissolved in 3 mL toluene and heated at reflux by Dean-Stark for 16 hours. After the solvent was removed, the reaction mixture was purified by column chromatography to afford Compound 3 as a pale-yellow solid (82.8 mg, 34%).

$^1$H NMR (300 MHz, d$^6$-DMSO) δ 7.29-7.09 (m, 5H), 7.05 (t, J=7.5 Hz, 1H), 6.88 (d, J=7.2 Hz, 2H), 6.74 (t, J=7.2 Hz, 1H), 3.92 (q, J=6.9 Hz, 1H), 3.84 (s, 2H), 3.14-3.05 (m, 4H), 2.73-2.56 (m, 4H), 2.29 (s, 3H), 1.45 (d, J=6.9 Hz, 3H).

ESI-MS $C_{25}H_{27}FN_6O$: 446.2, found: 447.2 (M+H$^+$)$^+$, 469.2 (M+Na$^+$)$^+$.

Example 4: 6-benzyl-5-methyl-2-(1-(4-phenylpiperazin-1-yl)ethyl)-[1,2,4]triazolo[1,5-a]pyrimidin-7(4H)-one (Compound 4)

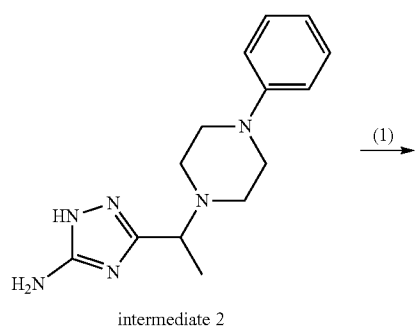

intermediate 2

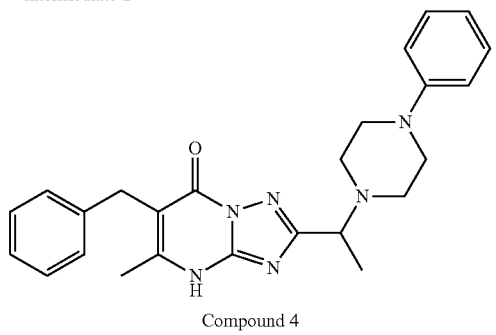

Compound 4

Reagents and conditions: 2-benzyl-3-oxo-butyric acid ethyl ester, toluene, reflux by Dean-Stark, 16 h, and yield and yield 19%.

Intermediate 2 (150 mg, 0.55 mmol) and 2-benzyl-3-oxo-butyric acid ethyl ester (145.8 mg, 0.66 mmol) were dissolved in 3 mL toluene and heated at reflux by Dean-Stark for 16 hours. After the solvent was removed, the reaction mixture was purified by column chromatography to afford Compound 4 as a pale-yellow solid (45.7 mg, 19%).

$^1$H NMR (300 MHz, d$^6$-DMSO) δ 7.30-7.10 (m, 7H), 6.88 (d, J=8.2 Hz, 2H), 6.74 (t, J=7.2 Hz, 1H), 3.91 (q, J=6.9 Hz, 1H), 3.85 (s, 2H), 3.20-2.99 (m, 4H), 2.75-2.53 (m, 4H), 2.30 (s, 3H), 1.44 (d, J=6.9 Hz, 3H).

ESI-MS $C_{25}H_{28}N_6O$: 428.2, found: 429.3 (M+H$^+$)$^+$, 451.2 (M+Na$^+$)$^+$.

Example 5: 6-(2-fluoro-4-methoxybenzyl)-5-methyl-2-(1-(4-phenylpiperazin-1-yl)ethyl)-[1,2,4]triazolo[1,5-a]pyrimidin-7(4H)-one (Compound 5)

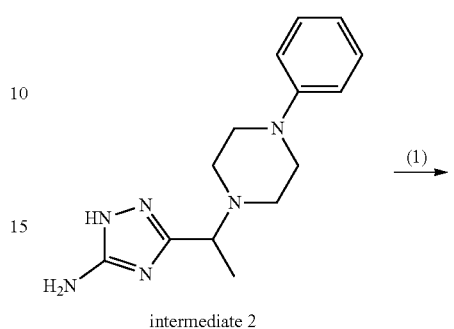

intermediate 2

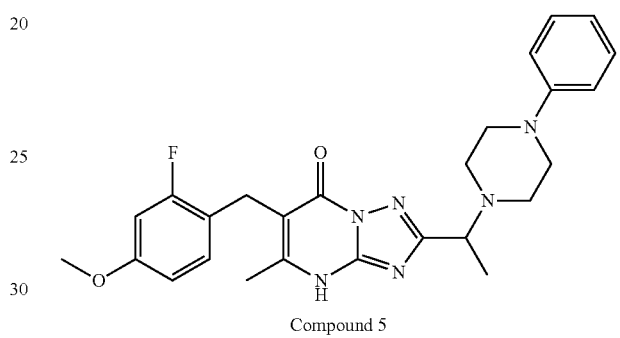

Compound 5

Reagents and conditions: (1) 2-(2-fluoro-4-methoxy-benzyl)-3-oxo-butyric acid ethyl ester, toluene, reflux by Dean-Stark, 16 h, and yield and 39%.

Intermediate 2 (200 mg, 0.74 mmol) and 2-(2-fluoro-4-methoxy-benzyl)-3-oxo-butyric acid ethyl ester (236.7 mg, 0.88 mmol) were dissolved in 3 mL toluene and heated at reflux by Dean-Stark for 16 hours. After the solvent was removed, the reaction mixture was purified by column chromatography to afford Compound 5 as a pale-yellow solid (138.2 mg, 39%).

$^1$H NMR (400 MHz, d$^6$-DMSO) δ 7.17 (t, J=7.3 Hz, 2H), 7.06 (t, J=8.9 Hz, 1H), 6.88 (d, J=7.3 Hz, 2H), 6.80-6.70 (m, 2H), 6.63 (dd, J=8.9, 2.5 Hz, 1H), 3.91 (q, J=7.0 Hz, 1H), 3.75 (s, 2H), 3.71 (s, 3H), 3.13-3.03 (m, 4H), 2.71-2.57 (m, 4H), 2.29 (s, 3H), 1.44 (d, J=7.0 Hz, 3H).

ESI-MS $C_{26}H_{29}FN_6O_2$: 476.2, found: 477.2 (M+H$^+$)$^+$, 499.3 (M+Na$^+$)$^+$.

Example 6: 6-(3-chloro-2-fluorobenzyl)-5-methyl-2-((4-phenylpiperazin-1-yl)methyl)-[1,2,4]triazolo[1,5-a]pyrimidin-7(3H)-one (Compound 6)

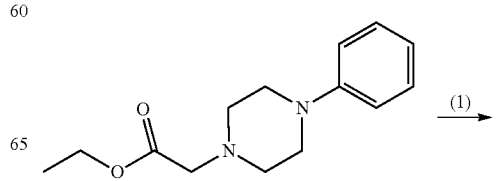

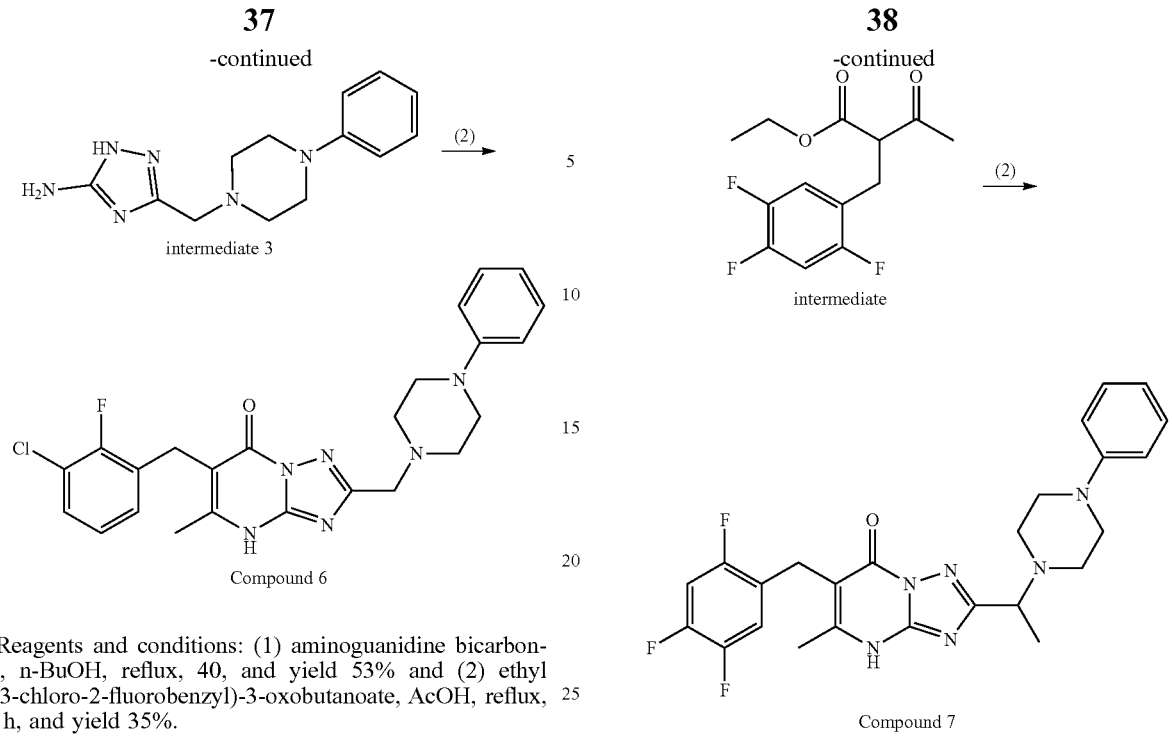

Reagents and conditions: (1) aminoguanidine bicarbonate, n-BuOH, reflux, 40, and yield 53% and (2) ethyl 2-(3-chloro-2-fluorobenzyl)-3-oxobutanoate, AcOH, reflux, 16 h, and yield 35%.

Step 1

Following the procedure for preparing intermediate 1, aminoguanidine bicarbonate (383.8 mg, 2.82 mmol) and ethyl 2-(4-phenylpiperazin-1-yl)acetate (700 mg, 2.82 mmol) were dissolved in 1.5 mL n-butanol and heated at reflux for 40 hours. Intermediate 3 was obtained as a yellow solid (387.9 mg, 53%).

$^1$H NMR (400 MHz, d$^6$-DMSO): δ 7.19 (d, J=6.6 Hz, 2H), 6.91 (d, J=6.6 Hz, 2H), 6.76 (t, J=6.6 Hz, 1H), 5.68 (s, 2H), 3.35 (s, 2H), 3.12-3.00 (m, 4H), 2.60-2.53 (m, 4H).

ESI-MS $C_{13}H_{18}N_6$: 258.2, found: 259.2 (M+H$^+$)$^+$, 281.1 (M+Na$^+$)$^+$.

Step 2

Following the procedure described in Example 1, intermediate 3 (100 mg, 0.39 mmol) and ethyl 2-(3-chloro-2-fluorobenzyl)-3-oxobutanoate (106.4 mg, 0.39 mmol) were dissolved in 1 mL acetic acid and heated at reflux for 16 hours. Compound 6 was obtained as a white solid (63.3 mg, 35%).

$^1$H NMR (400 MHz, CDCl$_3$): δ 7.30-7.15 (m, 3H), 6.98-6.81 (m, 5H), 4.00 (s, 2H), 3.79 (s, 2H), 3.49 (s, 1H), 3.17-3.11 (m, 4H), 2.74-2.67 (m, 4H), 2.61 (s, 3H).

ESI-MS $C_{24}H_{24}ClFN_6O$: 466.2, found: 467.2 (M+H$^+$)$^+$, 489.2 (M+Na$^+$)$^+$.

Example 7: 5-methyl-2-(1-(4-phenylpiperazin-1-yl)ethyl)-6-(2,4,5-trifluorobenzyl)-[1,2,4]triazolo[1,5-a]pyrimidin-7(4H)-one (Compound 7)

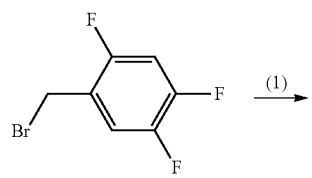

Reagents and conditions: (1) ethyl acetoacetate, DIPEA, LiCl, THF, reflux, 16 h, and yield 16% and (2) intermediate 2, AcOH, reflux, 16 h, and yield 62%.

Step 1

2,4,5-Trifluorobenzyl bromide (571 mg, 2.54 mmol), ethyl acetoacetate (300 mg, 2.30 mmol), LiCl (117 mg, 2.77 mmol) and DIPEA (0.48 mL, 2.77 mmol) were dissolved in 5 mL THF, and the mixture was refluxed for 16 hours. The reaction mixture was extracted with H$_2$O and CH$_2$Cl$_2$. The organic layer was collected, dried over MgSO$_4$, filtered, and concentrated to afford a crude, which was purified by column chromatography (16.7% EtOAc in hexane as eluent) to obtain intermediate 4 (104 mg, 16%).

ESI-MS $C_{13}H_{13}F_3O_3$: 274.1, found: 275.1 (M+H$^+$)$^+$, 297.0 (M+Na$^+$)$^+$.

Step 2

Intermediate 4 (104 mg, 0.38 mmol) and intermediate 2 (103 mg, 0.38 mmol) were dissolved in 1 mL acetic acid and heated at reflux for 16 hours. The residue was adjusted to pH>7 with saturated NaHCO$_{3(aq.)}$, then extracted with CH$_2$Cl$_2$. The organic layers were collected, dried over MgSO$_4$, filtered, and concentrated to afford a crude, which was purified by column chromatography (5% MeOH in CH$_2$Cl$_2$ as eluent) to obtain Compound 7 as a white solid (114 mg, 62%).

$^1$H NMR (400 MHz, CDCl$_3$): δ 7.34-7.21 (m, 3H), 6.91-6.77 (m, 4H), 4.00 (q, J=6.8 Hz, 1H), 3.89 (s, 2H), 3.20-3.13 (m, 4H), 2.84-2.76 (m, 2H), 2.74-2.65 (m, 2H), 2.56 (s, 3H), 1.55 (d, J=6.8 Hz, 3H).

ESI-MS $C_{25}H_{25}F_3N_6O$: 482.2, found: 483.2 (M+H$^+$)$^+$, 505.3 (M+Na$^+$)$^+$.

Example 8: 5-methyl-6-(3-methylbenzyl)-2-(1-(4-phenylpiperazin-1-yl)ethyl)-[1,2,4]triazolo[1,5-a]pyrimidin-7(4H)-one (Compound 8)

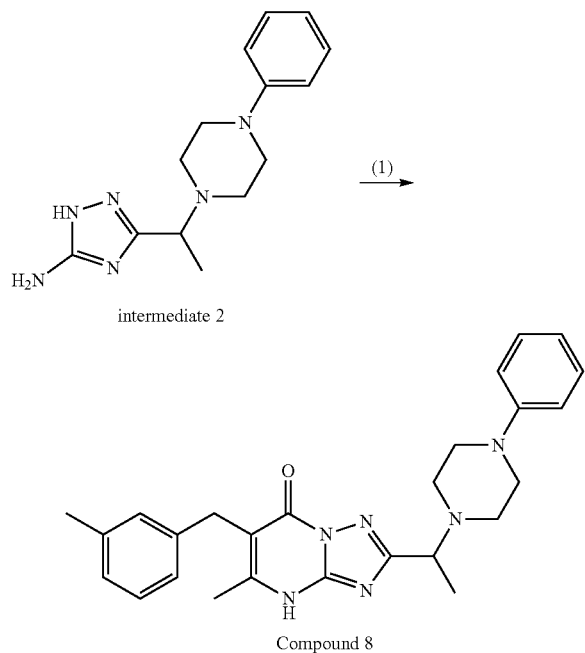

Reagents and conditions: 2-(3-methyl-benzyl)-3-oxo-butyric acid ethyl ester, toluene, reflux by Dean-Stark, 16 h, and yield and yield 20%.

Intermediate 2 (150 mg, 0.55 mmol) and 2-(3-methyl-benzyl)-3-oxo-butyric acid ethyl ester (129.2 mg, 0.55 mmol) were dissolved in 3 mL toluene and heated at reflux by Dean-Stark for 16 hours. After the solvent was removed, the reaction mixture was purified by column chromatography to afford Compound 8 as a pale-yellow solid (49.8 mg, 20%).

$^1$H-NMR (300 MHz, d$^6$-DMSO): δ 7.23-7.07 (m, 3H), 7.05-6.93 (m, 3H), 6.87 (d, J=7.2 Hz, 2H), 6.74 (t, J=7.2 Hz, 1H), 3.91 (q, J=6.9 Hz, 1H), 3.80 (s, 2H), 3.13-3.03 (m, 4H), 2.72-2.56 (m, 4H), 2.29 (s, 3H), 2.24 (s, 3H), 1.44 (d, J=6.9 Hz, 3H).

ESI-MS $C_{26}H_{30}N_6O$: 442.2, found: 443.1 (M+H$^+$)$^+$, 465.1 (M+Na$^+$)$^+$.

Example 9: 6-(3-methoxybenzyl)-5-methyl-2-(1-(4-phenylpiperazin-1-yl)ethyl)-[1,2,4]triazolo[1,5-a]pyrimidin-7(4H)-one (Compound 9)

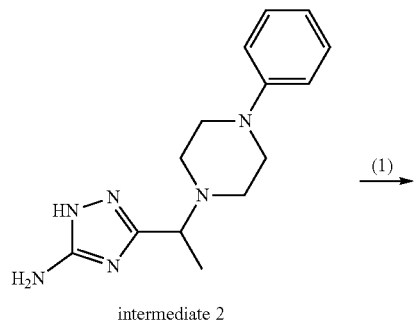

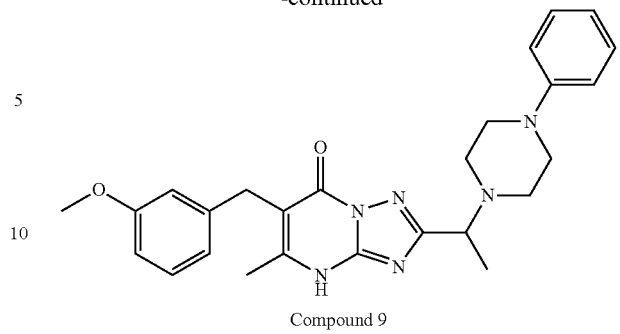

Reagents and conditions: 2-(3-methoxy-benzyl)-3-oxo-butyric acid ethyl ester, toluene, reflux by Dean-Stark, 16 h, and yield and yield 39%.

Intermediate 2 (150 mg, 0.55 mmol) and 2-(3-methoxy-benzyl)-3-oxo-butyric acid ethyl ester (165.6 mg, 0.66 mmol) were dissolved in 3 mL toluene and heated at reflux by Dean-Stark for 16 hours. After the solvent was removed, the reaction mixture was purified by column chromatography to afford Compound 9 as a pale-yellow solid (99.1 mg, 39%).

$^1$H NMR (300 MHz, d$^6$-DMSO) δ 7.21-7.10 (m, 3H), 6.88 (d, J=8.2 Hz, 2H), 6.83-6.69 (m, 4H), 3.91 (q, J=6.9 Hz, 1H), 3.82 (s, 2H), 3.70 (s, 3H), 3.12-3.03 (m, 4H), 2.71-2.56 (m, 4H), 2.30 (s, 3H), 1.44 (d, J=6.9 Hz, 3H).

ESI-MS $C_{26}H_{30}N_6O_2$: 458.2, found: 459.3 (M+H$^+$)$^+$, 481.2 (M+Na$^+$)$^+$.

Example 10: 6-(3-fluorobenzyl)-5-methyl-2-(1-(4-phenylpiperazin-1-yl)ethyl)-[1,2,4]triazolo[1,5-a]pyrimidin-7(4H)-one (Compound 10)

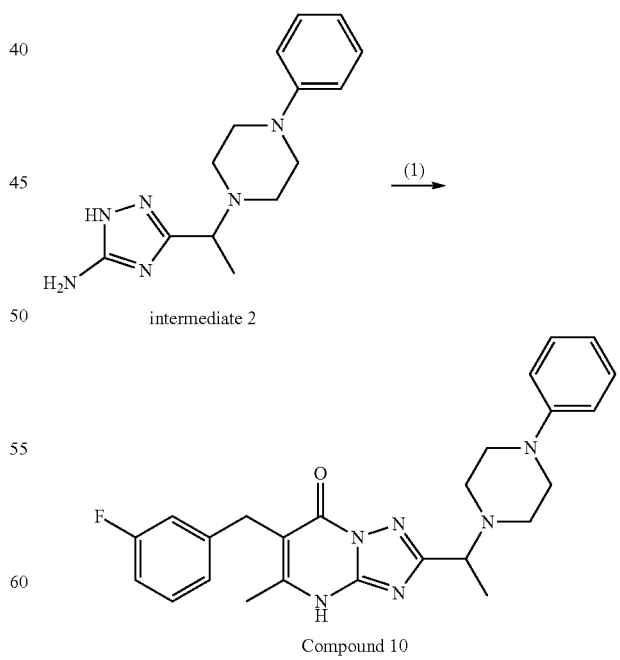

Reagents and conditions: 2-(3-fluoro-benzyl)-3-oxo-butyric acid ethyl ester, toluene, reflux by Dean-Stark, 16 h, and yield and yield 13%.

Intermediate 2 (150 mg, 0.55 mmol) and 2-(3-fluorobenzyl)-3-oxo-butyric acid ethyl ester (131.4 mg, 0.55 mmol) were dissolved in 3 mL toluene and heated at reflux by Dean-Stark for 16 hours. After the solvent was removed, the reaction mixture was purified by column chromatography to afford Compound 10 as a pale-yellow solid (32.1 mg, 13%).

$^1$H NMR (400 MHz, d$^6$-DMSO) δ 7.33-7.22 (m, 1H), 7.17 (t, J=7.2 Hz, 2H), 7.10-6.93 (m, 3H), 6.88 (d, J=7.2 Hz, 2H), 6.74 (t, J=7.2 Hz, 1H), 3.89 (q, J=6.9 Hz, 1H), 3.86 (s, 2H), 3.11-3.04 (m, 4H), 2.71-2.57 (m, 4H), 2.26 (s, 3H), 1.44 (d, J=6.9 Hz, 3H).

ESI-MS $C_{25}H_{27}FN_6O$: 446.2, found: 447.1 (M+H$^+$)$^+$, 469.1 (M+Na$^+$)$^+$.

Example 11: 6-(3-chlorobenzyl)-5-methyl-2-(1-(4-phenylpiperazin-1-yl)ethyl)-[1,2,4]triazolo[1,5-a]pyrimidin-7(3H)-one (Compound 11)

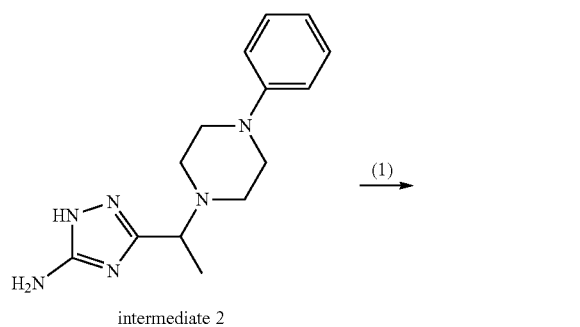

Reagents and conditions: 2-(3-chloro-benzyl)-3-oxo-butyric acid ethyl ester, toluene, reflux by Dean-Stark, 16 h, and yield and yield 10%.

Intermediate 2 (106.8 mg, 0.55 mmol) and 2-(3-chlorobenzyl)-3-oxo-butyric acid ethyl ester (100 mg, 0.55 mmol) were dissolved in 3 mL toluene and heated at reflux by Dean-Stark for 16 hours. After the solvent was removed, the reaction mixture was purified by column chromatography to afford Compound 11 as a pale-yellow solid (16.6 mg, 10%).

$^1$H NMR (300 MHz, DMSO): δ 7.33-7.12 (m, 6H), 6.88 (d, J=8.2 Hz, 2H), 6.74 (t, J=7.3 Hz, 1H), 3.91 (q, J=6.9 Hz, 1H), 3.85 (s, 2H), 3.16-3.05 (m, 4H), 2.75-2.56 (m, 4H), 2.30 (s, 3H), 1.44 (d, J=6.9 Hz, 3H).

E

SI-MS $C_{25}H_{27}ClN_6O$: 462.2, found: 463.1 (M+H$^+$)$^+$, 485.1 (M+Na$^+$)$^+$.

Example 12: 6-(3-chlorobenzyl)-5-methyl-2-((4-phenylpiperazin-1-yl)methyl)-[1,2,4]triazolo[1,5-a]pyrimidin-7(3H)-one (Compound 12)

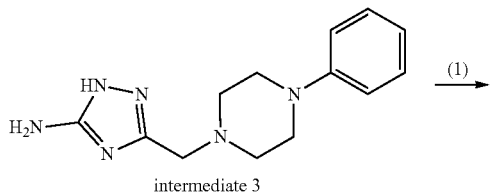

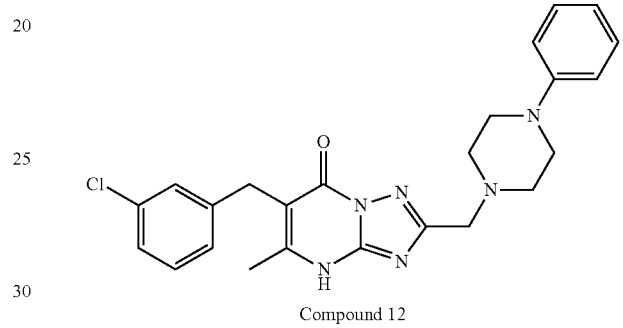

Reagents and conditions: ethyl 2-(3-chlorobenzyl)-3-oxobutanoate, AcOH, reflux, 16 h, and yield 32%

Following the procedure described in Example 1 above, intermediate 3 (100 mg, 0.39 mmol) and ethyl 2-(3-chlorobenzyl)-3-oxobutanoate (99.3 mg, 0.39 mmol) were dissolved in 1 mL acetic acid and heated at reflux for 16 hours. Compound 12 was obtained as a white solid (55.8 mg, 32%).

$^1$H NMR (300 MHz, CDCl$_3$): δ 7.31-7.19 (m, 3H), 7.17-7.09 (m, 3H), 6.94-6.81 (m, 3H), 3.96 (s, 2H), 3.80 (s, 2H), 3.25-3.10 (m, 4H), 2.76-2.67 (m, 4H), 2.53 (s, 3H).

ESI-MS $C_{24}H_{25}ClN_6O$: 448.2, found: 449.2 (M+H$^+$)$^+$, 471.2 (M+Na$^+$)$^+$.

Example 13: 5-methyl-2-(1-(4-phenylpiperazin-1-yl)ethyl)-6-(3-(trifluoromethyl)benzyl)-[1,2,4]triazolo[1,5-a]pyrimidin-7(4H)-one (Compound 13)

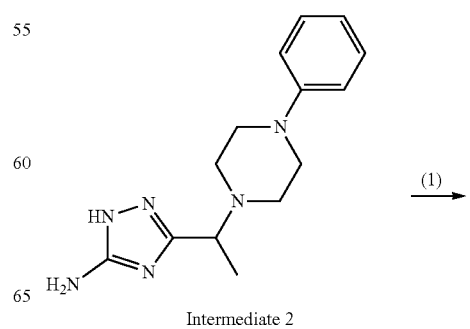

-continued

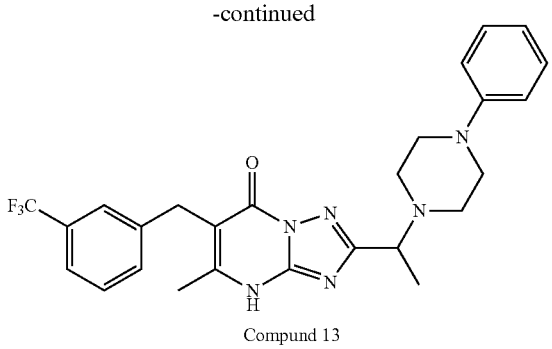

Compound 13

Reagents and conditions: (1) 3-oxo-2-(3-trifluoromethyl-benzyl)-butyric acid ethyl ester, toluene, reflux by Dean-Stark, 16 h, and yield 34%.

Intermediate 2 (150 mg, 0.55 mmol) and 3-oxo-2-(3-trifluoromethyl-benzyl)-butyric acid ethyl ester (190.8 mg, 0.66 mmol) were dissolved in 3 mL toluene and heated at reflux by Dean-Stark) for 16 hours. After the solvent was removed, the reaction mixture was purified by column chromatography to afford Compound 13 as a pale-yellow solid (93 mg, 34%).

$^1$H NMR (400 MHz, DMSO) δ 7.68-7.42 (m, 4H), 7.17 (d, J=8.2 Hz, 2H), 6.88 (d, J=8.2 Hz, 2H), 6.74 (t, J=8.2 Hz, 1H), 3.94 (s, 2H), 3.91-3.87 (m, 1H), 3.12-3.08 (m, 4H), 2.75-2.60 (m, 4H), 2.31 (s, 3H), 1.44 (d, J=7.5 Hz, 3H).

ESI-MS $C_{26}H_{27}F_3N_6O$: 496.2, found: 497.2 $(M+H^+)^+$, 519.2 $(M+Na^+)^+$.

Example 14: 6-(3,5-dimethylbenzyl)-5-methyl-2-(1-(4-phenylpiperazin-1-yl)ethyl)-[1,2,4]triazolo[1,5-a]pyrimidin-7(4H)-one (Compound 14)

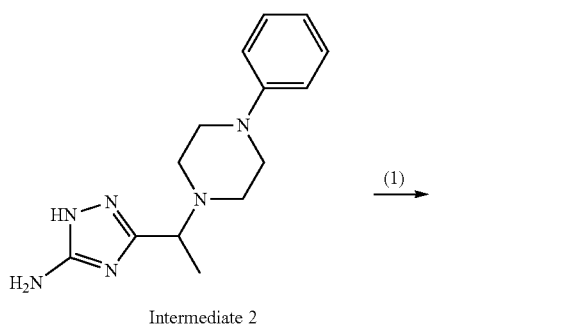

Intermediate 2

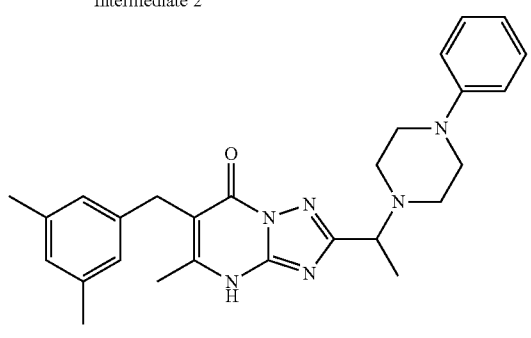

Compound 14

Reagents and conditions: 2-(3,5-dimethyl-benzyl)-3-oxo-butyric acid ethyl ester, toluene, reflux by Dean-Stark, 16 h, and yield 45%.

Intermediate 2 (150 mg, 0.55 mmol) and 2-(3,5-dimethyl-benzyl)-3-oxo-butyric acid ethyl ester (164.3 mg, 0.66 mmol) were dissolved in 3 mL toluene and heated at reflux by Dean-Stark for 16 hours. After the solvent was removed, the reaction mixture was purified by column chromatography to afford Compound 14 as a pale-yellow solid (113.8 mg, 45%).

$^1$H NMR (400 MHz, DMSO) δ 7.17 (d, J=8.0 Hz, 2H), 6.88 (d, J=8.0 Hz, 2H), 6.85-6.70 (m, 4H), 3.98-3.88 (m, 1H), 3.76 (s, 2H), 3.17-3.06 (m, 4H), 2.76-2.58 (m, 4H), 2.29 (s, 3H), 2.19 (s, 6H), 1.45 (d, J=7.2 Hz, 3H).

ESI-MS $C_{27}H_{32}N_6O$: 456.3, found: 457.3 $(M+H^+)^+$, 479.2 $(M+Na^+)^+$.

Example 15: 6-(3-fluoro-4-methoxybenzyl)-5-methyl-2-(1-(4-phenylpiperazin-1-yl)ethyl)-[1,2,4]triazolo[1,5-a]pyrimidin-7(4H)-one (Compound 15)

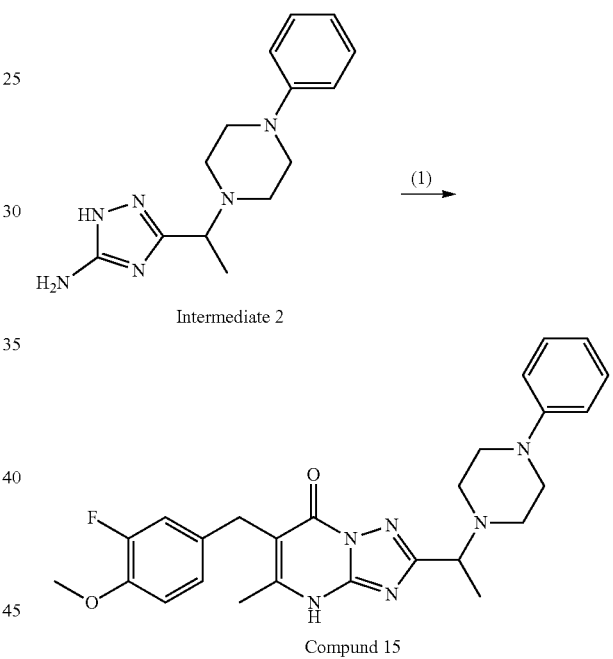

Compound 15

Reagents and conditions: (1) 2-(3-fluoro-4-methoxy-benzyl)-3-oxo-butyric acid ethyl ester, toluene, reflux by Dean-Stark, 16 h, and yield 9%.

Intermediate 2 (200 mg, 0.74 mmol) and 2-(3-fluoro-4-methoxy-benzyl)-3-oxo-butyric acid ethyl ester (394.5 mg, 1.47 mmol) were dissolved in 3 mL toluene and heated at reflux by Dean-Stark for 16 hours. After the solvent was removed, the reaction mixture was purified by column chromatography to afford Compound 15 as a pale-yellow solid (31.1 mg, 9%).

$^1$H NMR (400 MHz, DMSO) δ 7.17 (t, J=7.2 Hz, 2H), 7.10-6.94 (m, 3H), 6.88 (d, J=7.2 Hz, 2H), 6.74 (t, J=7.2 Hz, 1H), 3.90 (q, J=7.0 Hz, 1H), 3.77 (s, 3H), 3.77 (s, 2H), 3.17-2.98 (m, 4H), 2.72-2.54 (m, 4H), 2.29 (s, 3H), 1.44 (d, J=7.0 Hz, 3H).

ESI-MS $C_{26}H_{29}FN_6O_2$: 476.2, found: 477.2 $(M+H^+)^+$, 499.2 $(M+Na^+)^+$.

Example 16: 6-(3,4-difluorobenzyl)-5-methyl-2-(1-(4-phenylpiperazin-1-yl)ethyl)-[1,2,4]triazolo[1,5-a]pyrimidin-7(4H)-one (Compound 16)

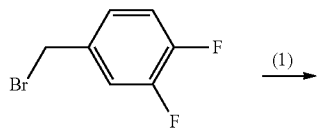

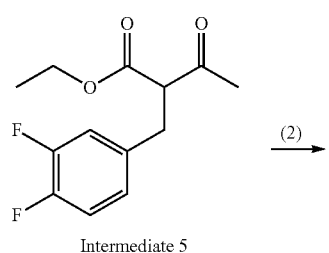

Intermediate 5

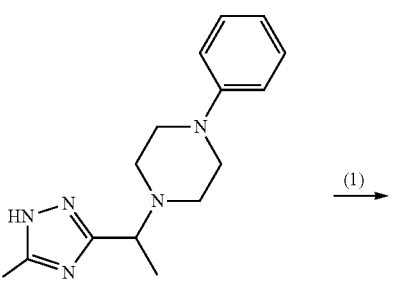

Compound 16

Reagents and conditions: (1) ethyl acetoacetate, DIPEA, LiCl, THF, 80° C., 16 h, and yield 44%, and (2) Intermediate 2, toluene, reflux by Dean-Stark, 16 h, and yield 32%.

4-Bromomethyl-1,2-difluoro-benzene (0.6 mL, 0.48 mmol), ethyl acetoacetate (1.2 mL, 0.94 mmol), LiCl (0.4 g, 0.94 mmol) and DIPEA (1.7 mL, 0.94 mmol) were dissolved in 20 mL THF, and then stirred at 80° C. for 16 hours. After the solvent was removed, the reaction mixture was diluted with EtOAc, washed sequentially with water and brine. The organic layer was collected, dried over MgSO$_4$, filtered, and concentrated to afford a crude, which was purified by column chromatography (gradient elution as 1% to 5% EtOAc in hexane) to give intermediate 5 as a colorless liquid (529.5 mg, 44%).

$^1$H NMR (400 MHz, DMSO) δ 7.38-7.27 (m, 2H), 7.10-7.01 (m, 1H), 4.15-3.98 (m, 3H), 3.11-2.89 (m, 2H), 2.18 (s, 3H), 1.09 (t, J=7.1 Hz, 3H).

ESI-MS C$_{13}$H$_{14}$F$_2$O$_3$: 256.1, found: 257.1 (M+H$^+$)$^+$, 279.1 (M+Na$^+$)$^+$.

Intermediate 5 (169.6 mg, 0.66 mmol) and Intermediate 2 (150 mg, 0.55 mmol) were dissolved in 3 mL toluene and heated at reflux by Dean-Stark for 16 hours. After the solvent was removed, the reaction mixture was purified by column chromatography to afford Compound 16 as a yellow oil (81.7 mg, 32%).

$^1$H NMR (400 MHz, DMSO) δ 7.35-7.24 (m, 2H), 7.18 (t, J=8.2 Hz, 2H), 7.09 (s, 1H), 6.88 (d, J=8.2 Hz, 2H), 6.74 (t, J=8.2 Hz, 1H), 3.97-3.88 (m, 1H), 3.84 (s, 2H), 3.13-3.08 (m, 4H), 2.71-2.60 (m, 4H), 2.30 (s, 3H), 1.45 (d, J=7.4 Hz, 3H).

ESI-MS C$_{25}$H$_{26}$F$_2$N$_6$O: 464.2, found: 465.2 (M+H$^+$)$^+$, 487.2 (M+Na$^+$)$^+$.

Example 17: 5-methyl-6-(4-methylbenzyl)-2-(1-(4-phenylpiperazin-1-yl)ethyl)-[1,2,4]triazolo[1,5-a]pyrimidin-7(4H)-one (Compound 17)

Intermediate 2

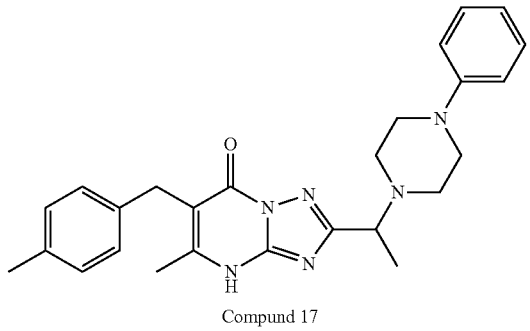

Compound 17

Reagents and conditions: 2-(4-methyl-benzyl)-3-oxo-butyric acid ethyl ester, toluene, reflux by Dean-Stark, 16 h, and yield 33%.

Intermediate 2 (232.2 mg, 0.85 mmol) and 2-(4-methylbenzyl)-3-oxo-butyric acid ethyl ester (200 mg, 0.85 mmol) were dissolved in 3 mL toluene and heated at reflux by Dean-Stark for 16 hours. After the solvent was removed, the reaction mixture was purified by column chromatography to afford Compound 17 as a pale-yellow solid (124.2 mg, 33%).

$^1$H NMR (300 MHz, DMSO) δ 7.18 (t, J=8.2 Hz, 2H), 7.10 (d, J=7.8 Hz, 2H), 7.04 (d, J=7.8 Hz, 2H), 6.88 (d, J=8.2 Hz, 2H), 6.74 (t, J=8.2 Hz, 1H), 3.91 (q, J=6.9 Hz, 1H), 3.79 (s, 2H), 3.17-2.98 (m, 4H), 2.78-2.54 (m, 4H), 2.28 (s, 3H), 2.23 (s, 3H), 1.44 (d, J=6.9 Hz, 3H).

ESI-MS C$_{26}$H$_{30}$N$_6$O: 442.2, found: 443.3 (M+H$^+$)$^+$, 465.3 (M+Na$^+$)$^+$.

Example 18: 6-(4-methoxybenzyl)-5-methyl-2-(1-(4-phenylpiperazin-1-yl)ethyl)-[1,2,4]triazolo[1,5-a]pyrimidin-7(4H)-one (Compound 18)

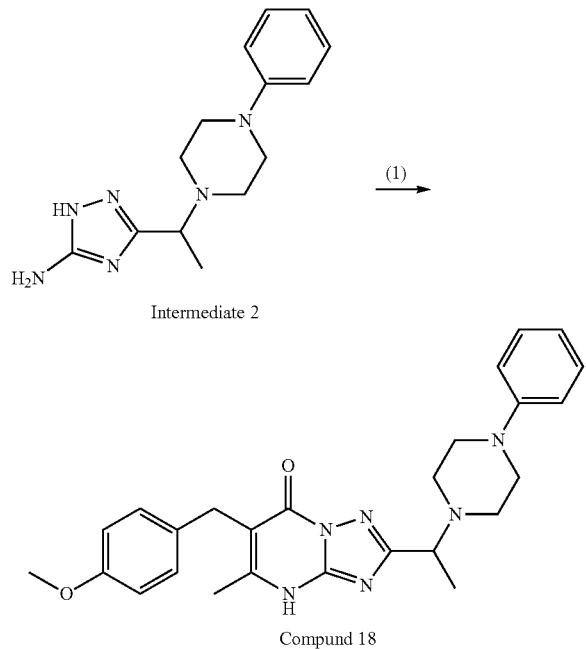

Reagents and conditions: 2-(4-methoxy-benzyl)-3-oxo-butyric acid ethyl ester, toluene, reflux by Dean-Stark, 16 h, and yield 39%.

Intermediate 2 (217.3 mg, 0.8 mmol) and 2-(4-methoxy-benzyl)-3-oxo-butyric acid ethyl ester (200 mg, 0.8 mmol) were dissolved in 3 mL toluene and heated at reflux by Dean-Stark for 16 hours. After the solvent was removed, the reaction mixture was purified by column chromatography to afford Compound 18 as a pale-yellow solid (144 mg, 39%).

$^1$H NMR (300 MHz, DMSO) δ 7.20 (d, J=7.2 Hz, 2H), 7.14 (d, J=8.5 Hz, 2H), 6.88 (d, J=7.2 Hz, 2H), 6.81 (d, J=8.5 Hz, 2H), 6.74 (t, J=7.2 Hz, 1H), 3.91 (q, J=6.9 Hz, 1H), 3.77 (s, 2H), 3.69 (s, 3H), 3.15-3.01 (m, 4H), 2.77-2.53 (m, 4H), 2.30 (s, 3H), 1.44 (d, J=6.9 Hz, 3H).

ESI-MS $C_{26}H_{30}N_6O_2$: 458.2, found: 459.2 (M+H$^+$)$^+$, 481.2 (M+Na$^+$)$^+$.

Example 19: 6-(4-fluorobenzyl)-5-methyl-2-(1-(4-phenylpiperazin-1-yl)ethyl)-[1,2,4]triazolo[1,5-a]pyrimidin-7(4H)-one (Compound 19)

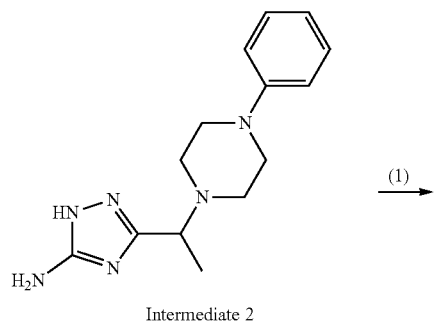

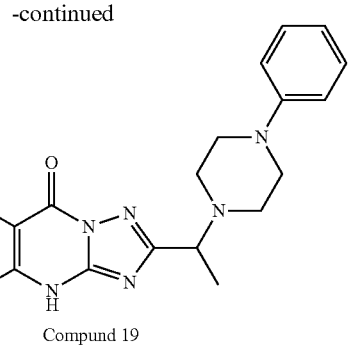

Reagents and conditions: 2-(4-fluoro-benzyl)-3-oxo-butyric acid ethyl ester, toluene, reflux by Dean-Stark, 16 h, and yield 19%.

Intermediate 2 (150 mg, 0.55 mmol) and 2-(4-fluoro-benzyl)-3-oxo-butyric acid ethyl ester (131.4 mg, 0.55 mmol) were dissolved in 3 mL toluene and heated at reflux by Dean-Stark for 16 hours. After the solvent was removed, the reaction mixture was purified by column chromatography to afford Compound 19 as a pale-yellow solid (46.8 mg, 19%).

$^1$H NMR (400 MHz, DMSO): δ 7.25 (t, J=7.2 Hz, 2H), 7.18 (dd, J=8.8, 7.2 Hz, 2H), 7.05 (dd, J=9.5, 8.8 Hz, 2H), 6.88 (d, J=7.2 Hz, 2H), 6.74 (t, J=7.2 Hz, 1H), 3.89 (q, J=7.2 Hz, 1H), 3.82 (s, 2H), 3.16-3.00 (m, 4H), 2.77-2.54 (m, 4H), 2.28 (s, 3H), 1.44 (d, J=7.2 Hz, 3H).

ESI-MS $C_{25}H_{27}FN_6O$: 446.2, found: 447.1 (M+H$^+$)$^+$, 469.1 (M+Na$^+$)$^+$.

Example 20: 6-(4-chlorobenzyl)-5-methyl-2-(1-(4-phenylpiperazin-1-yl)ethyl)-[1,2,4]triazolo[1,5-a]pyrimidin-7(4H)-one (Compound 20)

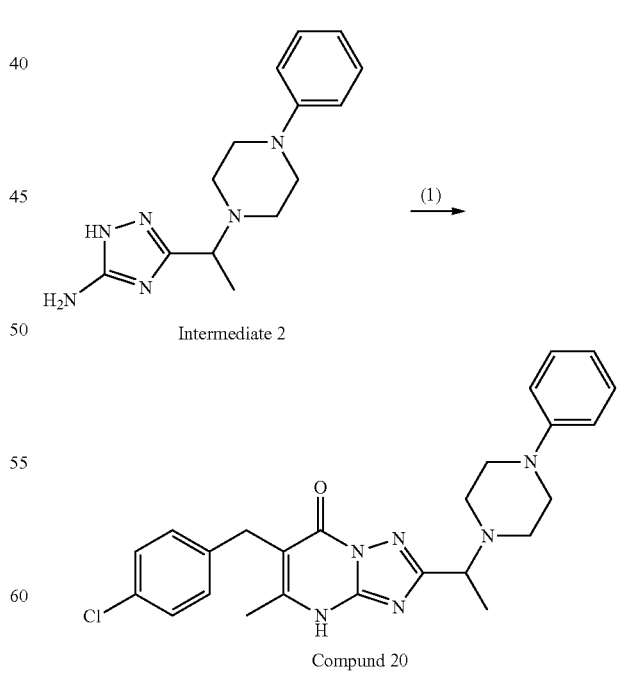

Reagents and conditions: 2-(4-chloro-benzyl)-3-oxo-butyric acid ethyl ester, toluene, reflux by Dean-Stark, 16 h, and yield 5%.

Intermediate 2 (214.2 mg, 0.78 mmol) and 2-(4-chlorobenzyl)-3-oxo-butyric acid ethyl ester (200 mg, 0.78 mmol) were dissolved in 3 mL toluene and heated at reflux by Dean-Stark for 16 hours. After the solvent was removed, the reaction mixture was purified by column chromatography to afford Compound 20 as a pale-yellow solid (21.4 mg, 5%).

$^1$H NMR (300 MHz, DMSO) δ 7.29 (d, J=8.6 Hz, 2H), 7.25 (d, J=8.6 Hz, 2H), 7.18 (t, J=7.8 Hz, 2H), 6.88 (d, J=7.8 Hz, 2H), 6.74 (t, J=7.8 Hz, 1H), 3.91 (q, J=7.0 Hz, 1H), 3.83 (s, 2H), 3.19-3.00 (m, 4H), 2.79-2.56 (m, 4H), 2.29 (s, 3H), 1.43 (d, J=7.0 Hz, 3H).

ESI-MS $C_{25}H_{27}ClN_6O$: 462.2, found: 463.2 $(M+H^+)^+$, 485.1 $(M+Na^+)^+$.

Example 21: 2,2'-((piperazine-1,4-diylbis(2-oxoethane-2,1-diyl))bis(sulfanediyl))bis(6-propylpyrimidin-4(3H)-one) (Compound 21)

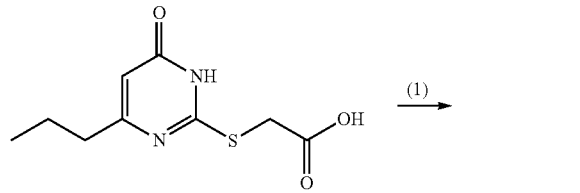

Compound 21

Reagents and conditions: piperazine, EDC, DMAP, DMF, r.t., 16 h, and yield 65%.

2-((6-Oxo-4-propyl-1,6-dihydropyrimidin-2-yl)thio)acetic acid (100 mg, 0.44 mmol), piperazine anhydride (20 mg, 0.21 mmol), EDC (80 mg, 0.42 mmol) and DMAP (10 mg, 0.08 mmol) were dissolved in 2 mL DMF, and then stirred at room temperature for 16 hours. The reaction mixture was extracted with H$_2$O and CH$_2$Cl$_2$. The organic layers were dried over MgSO$_4$, filtered and concentrated to afford a crude, which was purified by column chromatography (10% MeOH in CH$_2$Cl$_2$ as eluent) to obtain Compound 21 as a white solid (69 mg, 65%).

$^1$H NMR (400 MHz, DMSO) δ 5.95 (s, 2H), 4.20 (s, 2H), 4.18 (s, 2H), 3.69-3.40 (m, 8H), 2.36 (t, J=7.5 Hz, 4H), 1.58 (h, J=7.5 Hz, 4H), 0.86 (t, J=7.5 Hz, 6H).

ESI-MS $C_{22}H_{30}N_6O_4S_2$: 506.2, found: 507.2 $(M+H^+)^+$, 529.1 $(M+Na^+)^+$.

Example 22: 5-methyl-2-(1-(4-phenylpiperazin-1-yl)ethyl)-6-(4-(trifluoromethyl)benzyl)-[1,2,4]triazolo[1,5-a]pyrimidin-7(4H)-one (Compound 22)

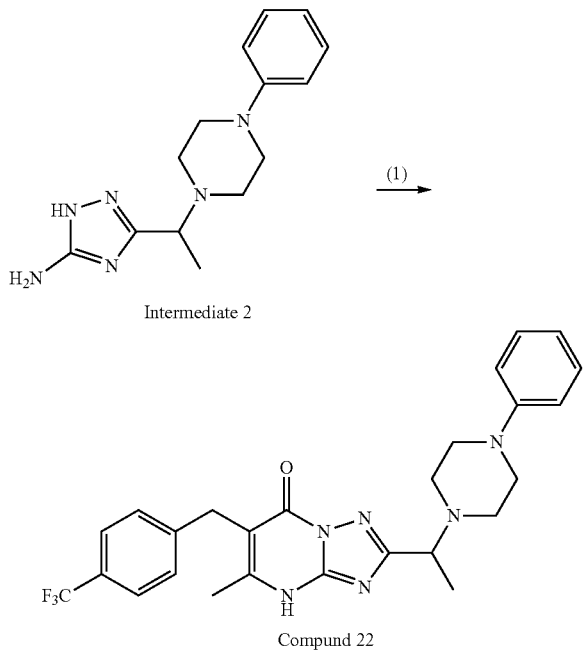

Reagents and conditions: 3-oxo-2-(4-trifluoromethyl-benzyl)-butyric acid ethyl ester, toluene, reflux by Dean-Stark, 16 h, and yield 14%.

Intermediate 2 (150 mg, 0.55 mmol) and 3-oxo-2-(4-trifluoromethyl-benzyl)-butyric acid ethyl ester (190.8 mg, 0.66 mmol) were dissolved in 3 mL toluene and heated at reflux by Dean-Stark for 16 hours. After the solvent was removed, the reaction mixture was purified by column chromatography to afford Compound 22 as a pale-yellow solid (38.5 mg, 14%).

$^1$H NMR (300 MHz, DMSO) δ 7.60 (d, J=8.2 Hz, 2H), 7.46 (d, J=8.2 Hz, 2H), 7.18 (d, J=7.7 Hz, 2H), 6.88 (d, J=7.7 Hz, 2H), 6.74 (d, J=7.7 Hz, 1H), 3.94 (s, 2H), 3.90 (q, J=7.0 Hz, 1H), 3.14-3.02 (m, 4H), 2.76-2.53 (m, 4H), 2.31 (s, 3H), 1.45 (d, J=7.0 Hz, 3H).

ESI-MS $C_{26}H_{27}F_3N_6O$: 496.2, found: 497.2 $(M+H^+)^+$, 519.2 $(M+Na^+)^+$.

Example 23: Benzyl 4-(2-((6-oxo-4-propyl-1,6-dihydropyrimidin-2-yl)thio)acetyl)piperazine-1-carboxylate (Compound 23)

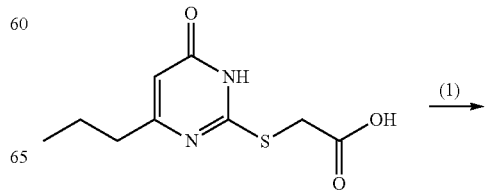

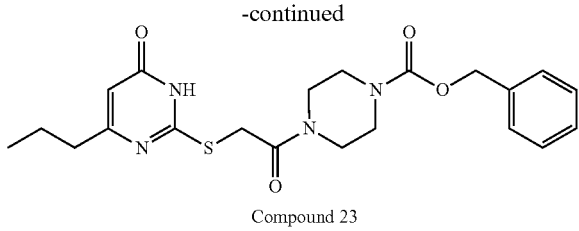

Compound 23

Reagents and conditions: benzyl-1-piperazine carboxylate, EDC, DMAP, DMF, r.t., 16 h, and yield 74%.

2-((6-Oxo-4-propyl-1,6-dihydropyrimidin-2-yl)thio)acetic acid (100 mg, 0.44 mmol), benzyl-1-piperazine carboxylate (0.1 mL, 0.48 mmol), EDC (101 mg, 0.53 mmol) and DMAP (11 mg, 0.09 mmol) were dissolved in 2 mL DMF and then stirred at room temperature for 16 hours. The reaction mixture was extracted with H$_2$O and CH$_2$Cl$_2$. The organic layers were dried over MgSO$_4$, filtered and concentrated to afford a crude, which was purified by column chromatography (10% MeOH in CH$_2$Cl$_2$ as eluent) to obtain Compound 23 as a white solid (139 mg, 74%).

$^1$H NMR (400 MHz, CDCl$_3$): δ 7.44-7.29 (m, 5H), 6.03 (d, J=0.8 Hz, 1H), 5.15 (s, 2H), 4.12 (s, 2H), 3.70-3.43 (m, 8H), 2.43 (t, J=7.4 Hz, 2H), 1.63 (sextet, J=7.4 Hz, 2H), 0.93 (t, J=7.4 Hz, 3H).

ESI-MS C$_{21}$H$_{26}$N$_4$O$_4$S: 430.2, found: 431.1 (M+H$^+$)$^+$, 453.1 (M+Na$^+$)$^+$.

Example 24: 2-((2-(4-(2-methoxyphenyl)piperazin-1-yl)-2-oxoethyl)thio)-5-propylpyrimidin-4(3H)-one (Compound 24)

(0.8 g, 5.78 mmol) were dissolved in 10 mL H$_2$O and then stirred at 100° C. for 20 minutes. The reaction mixture was cooled to 0° C. and acidified by 6N HCl$_{(aq)}$. The precipitate was formed, filtered to afford intermediate 6 as a white solid (1.2 g, 89%).

$^1$H NMR (300 MHz, DMSO) δ 5.95 (s, 1H), 3.88 (s, 2H), 2.36 (t, J=7.8 Hz, 2H), 1.59 (sextet, J=7.8 Hz, 2H), 0.86 (t, J=7.8 Hz, 3H).

Step 2

Intermediate 6 (100 mg, 0.44 mmol), 1-(2-methoxyphenyl)-piperazine (93 mg, 0.48 mmol), EDC (101 mg, 0.53 mmol) and DMAP (11 mg, 0.09 mmol) were dissolved in 2 mL DMF, and then stirred at room temperature for 16 hours. The reaction mixture was extracted with H$_2$O and CH$_2$Cl$_2$. The organic layer was dried over MgSO$_4$, filtered and concentrated to afford a crude, which was purified by column chromatography (10% MeOH in CH$_2$Cl$_2$ as eluent) to obtain Compound 24 as a white solid (154 mg, 87%).

$^1$H NMR (400 MHz, CDCl$_3$): δ 7.12-7.00 (m, 1H), 6.97-6.88 (m, 3H), 6.04 (s, 1H), 4.13 (s, 2H), 3.88 (s, 3H), 3.90-3.69 (m, 4H), 3.19-3.02 (m, 4H), 2.45 (d, J=7.4 Hz, 2H), 1.66 (sextet, J=7.4 Hz, 2H), 0.94 (t, J=7.4 Hz, 3H).

ESI-MS C$_{20}$H$_{26}$N$_4$O$_3$S: 402.2, found: 403.2 (M+H$^+$)$^+$, 425.1 (M+Na$^+$)$^+$.

Example 25: 6-((2-(4-(2-methoxyphenyl)piperazin-1-yl)-2-oxoethyl)thio)-1,5-dihydro-4H-pyrazolo[3,4-d] pyrimidin-4-one (Compound 25)

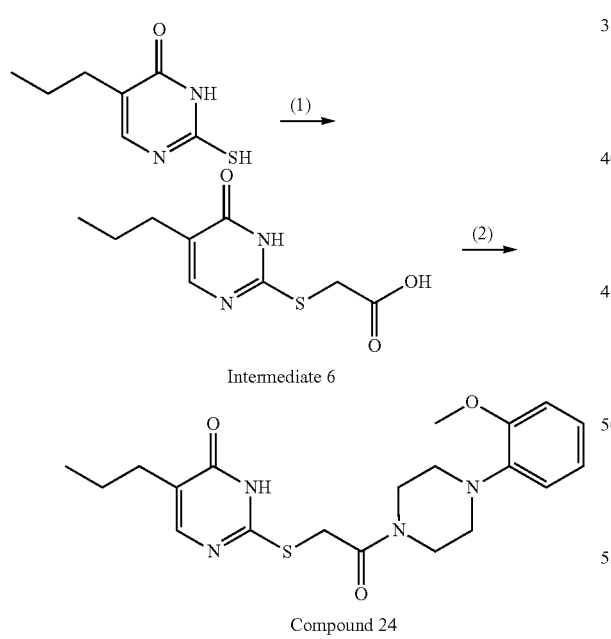

Intermediate 6

Compound 24

Reagents and conditions: (1) 2-bromoacetic acid, K$_2$CO$_3$, H$_2$O, 100° C., 20 min., and yield 89%, and (2) EDC, DMAP, DMF, r.t., 16 h, and yield 87%.

Step 1

2-Bromoacetic acid (1.1 g, 6.47 mmol), 2-mercapto-5-propylpyrimidin-4(3H)-one (1.0 g, 5.78 mmol) and K$_2$CO$_3$

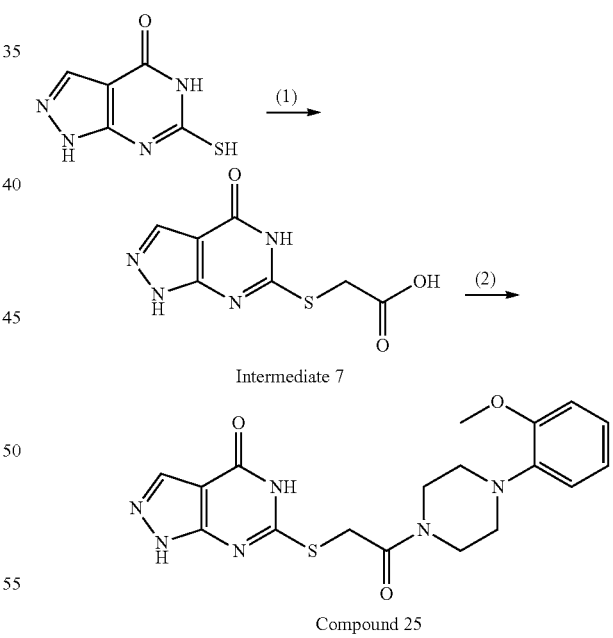

Intermediate 7

Compound 25

Reagents and conditions: (1) 2-bromoacetic acid, K$_2$CO$_3$, H$_2$O, 80° C., 10 min.- and (2) EDC, DMAP, DMF, r.t., 16 h, 27% over two steps.

Step 1

4-Hydroxy-6-mercaptopyrazolo[3,4-d]pyrimidine (200 mg, 1.19 mmol), 2-bromoacetic acid (182 mg, 1.31 mmol) and K$_2$CO$_3$ (181 mg, 1.31 mmol) were dissolved in 10 mL H₂O, and then stirred at 80° C. for 10 mins. The reaction was cooled to 0° C. and acidified by 1N HCl$_{(aq.)}$. The precipitate was formed, filtered and washed by H₂O to afford intermediate 7 as a white solid. It was used directly in the next step.

$^1$H NMR (400 MHz, DMSO) δ 12.36 (s, 1H), 8.03 (s, 1H), 4.01 (s, 2H).

ESI-MS C$_7$H$_6$N$_4$O$_3$S: 226.0, found: 227.0 (M+H$^+$)$^+$, 249.0 (M+Na$^+$)$^+$.

Step 2

Intermediate 7 (100 mg, 0.44 mmol), 1-(2-methoxyphenyl)-piperazine (93 mg, 0.49 mmol), EDC (102 mg, 0.53 mmol) and DMAP (11 mg, 0.09 mmol) were dissolved in 2 mL DMF, and then stirred at room temperature for 16 hours. The reaction mixture was extracted with H₂O and CH₂Cl₂. The organic layer was dried over MgSO₄, filtered and concentrated to afford a crude, which was purified by column chromatography (10% MeOH in CH₂Cl₂ as eluent) to obtain Compound 25 as a white solid (130 mg, 27% over two steps).

$^1$H NMR (400 MHz, DMSO): δ 12.40 (s, 1H), 7.95 (s, 1H), 7.04-6.83 (m, 4H), 4.32 (s, 2H), 3.80 (s, 3H), 3.75-3.58 (m, 4H), 3.09-2.85 (m, 4H).

ESI-MS C$_{18}$H$_{20}$N$_6$O$_3$S: 400.1, found: 401.1 (M+H$^+$)$^+$, 423.1 (M+Na$^+$)$^+$.

Example 26: 6-(3-chlorobenzyl)-5-methyl-2-((4-(thiazol-2-yl)piperazin-1-yl)methyl)-[1,2,4]triazolo[1,5-a] pyrimidin-7(3H)-one (Compound 26)

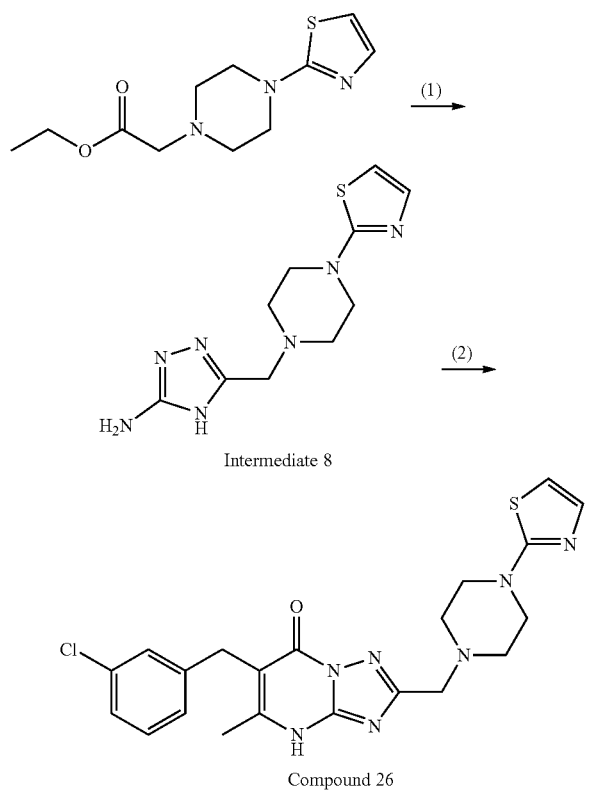

Compound 26

Reagents and conditions: (1) aminoguanidine bicarbonate, t-BuOH, 140° C., 40 h, and yield 30%, and (2) 2-(3-chloro-benzyl)-3-oxo-butyric acid ethyl ester, AcOH, reflux, 16 h, and yield 9%.

Step 1

Aminoguanidine bicarbonate (0.7 g, 0.54 mmol) and (4-thiazol-2-yl-piperazin-1-yl)-acetic acid ethyl ester (1.4 g, 0.54 mmol) were dissolved in 4 mL t-BuOH and heated at 140° C. for 40 hours. After the solvent was removed, the reaction mixture was purified by column chromatography to give intermediate 8 as a yellow solid (424.1 mg, 30%).

$^1$H NMR (400 MHz, DMSO) δ 11.78 (s, 1H), 7.14 (d, J=3.6 Hz, 1H), 6.83 (d, J=3.6 Hz, 1H), 5.82 (s, 2H), 3.40-3.33 (m, 4H), 3.33 (s, 2H), 2.63-2.50 (m, 4H).

ESI-MS C$_{10}$H$_{15}$N$_7$S: 265.1, found: 266.1 (M+H$^+$)$^+$, 288.1 (M+Na$^+$)$^+$.

Step 2

Intermediate 8 (104.1 mg, 0.39 mmol) and 2-(3-chlorobenzyl)-3-oxo-butyric acid ethyl ester (100 mg, 0.39 mmol) were dissolved in 1 mL acetic acid and heated at reflux for 16 hours. After the solvent was removed, the reaction mixture was neutralized by saturated sodium bicarbonate solution and extracted by dicholoromethane. The organic layers were collected, dried over MgSO₄, filtered and concentrated to afford a crude, which was purified by column chromatography to afford Compound 26 as a pale-yellow solid (16 mg, 9%).

$^1$H NMR (400 MHz, DMSO) δ 7.29-7.24 (m, 2H), 7.23-7.17 (m, 2H), 7.14 (d, J=3.6 Hz, 1H), 6.83 (d, J=3.6 Hz, 1H), 3.84 (s, 2H), 3.64 (s, 2H), 3.50 (s, 1H), 3.38 (t, J=5.2 Hz, 4H), 2.63 (t, J=5.2 Hz, 4H), 2.25 (s, 3H).

ESI-MS C$_{21}$H$_{22}$ClN$_7$OS: 455.1, found: 456.1 (M+H$^+$)$^+$, 478.0 (M+Na$^+$)$^+$.

Example 27: 2-((2-(4-(benzo[d]isothiazol-3-yl)piperazin-1-yl)-2-oxoethyl)thio)-6-propylpyrimidin-4(3H)-one (Compound 27)

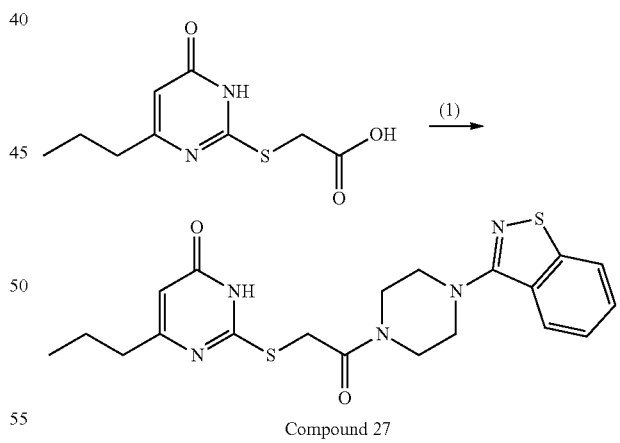

Compound 27

Reagents and conditions: EDC, DMAP, DMF, r.t., 16 h, and yield 90%.

2-((6-Oxo-4-propyl-1,6-dihydropyrimidin-2-yl)thio)acetic acid (100 mg, 0.44 mmol), 3-piperazin-1-yl-benzo[d]isothiazole (106 mg, 0.48 mmol), EDC (101 mg, 0.53 mmol) and DMAP (11 mg, 0.09 mmol) were dissolved in 2 mL DMF, and then stirred at room temperature for 16 hours. The reaction mixture was extracted with H₂O and CH₂Cl₂. The organic layers were dried over MgSO₄, filtered and concentrated to afford a crude, which was purified by column chromatography (10% MeOH in CH$_2$Cl$_2$ as eluent) to obtain Compound 27 as a white solid (169 mg, 90%).

$^1$H NMR (400 MHz, CDCl$_3$): δ 7.89 (dd, J=8.1, 1.0 Hz, 1H), 7.84 (dd, J=8.1, 1.0 Hz, 1H), 7.50 (ddd, J=8.1, 7.0, 1.0 Hz, 1H), 7.39 (ddd, J=8.1, 7.0, 1.0 Hz, 1H), 6.06 (s, 1H), 4.17 (s, 2H), 3.92-3.78 (m, 4H), 3.65-3.46 (m, 4H), 2.47 (d, J=7.4 Hz, 2H), 1.67 (sextet, J=7.4 Hz, 2H), 0.95 (t, J=7.4 Hz, 3H).

ESI-MS C$_{20}$H$_{23}$N$_5$O$_2$S$_2$: 429.1, found: 430.1 (M+H$^+$)$^+$, 452.1 (M+Na$^+$)$^+$.

Example 28: (S)-2-((2-(4-(2-methoxyphenyl)-3-methylpiperazin-1-yl)-2-oxoethyl)thio)-6-propylpyrimidin-4(3H)-one (Compound 28)

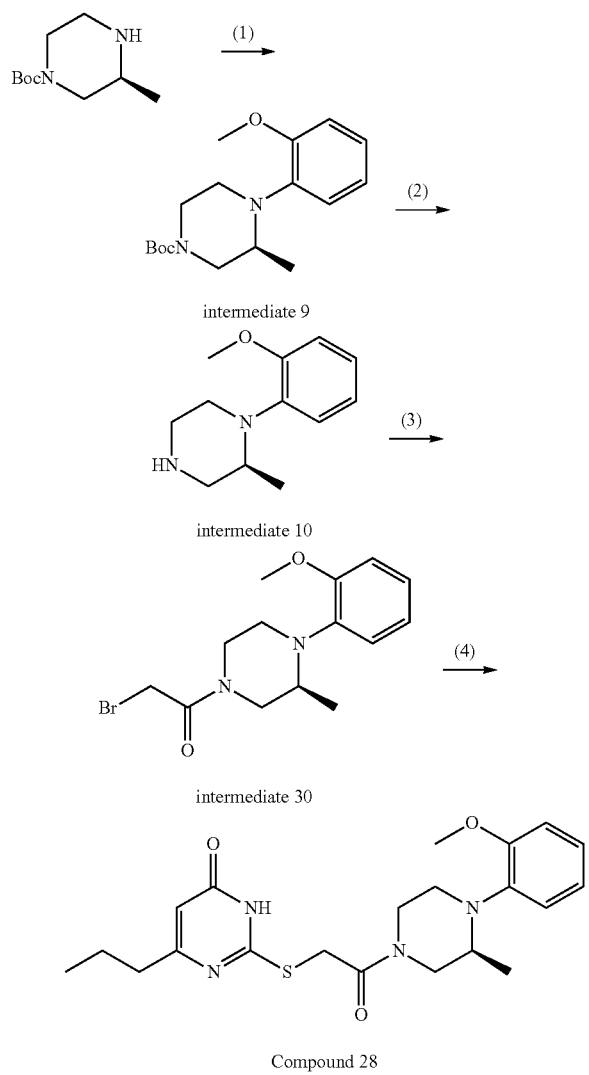

Compound 28

Reagents and conditions: (1) 2-bromoanisole, Pd$_2$(dba)$_3$, BINAP, t-BuONa, toluene, 50° C., 10 min.; 105° C., 16 h, and yield 37%; (2) TFA, CH$_2$Cl$_2$, 0° C.; r.t., 16 h; (3) 2-bromoacetic acid, EDC, DMAP, DMF, r.t., 16 h; and (4) 6-propyl-2-thiouracil, K$_2$CO$_3$, CH$_2$Cl$_2$, MeOH, 80° C., 4 h, 62% over three steps.

Step 1

Pd$_2$(dba)$_3$ (137 mg, 0.15 mmol) and BINAP (187 mg, 0.3 mmol) were dissolved in 10 mL toluene and stirred 10 minutes at 50° C. 2-Bromoanisole (0.2 mL, 1.65 mmol), tert-butyl (S)-3-methylpiperazine-1-carboxylate (300 mg, 1.5 mmol) and t-BuONa (288 mg, 3.00 mmol) were added to the reaction mixture, and then stirred at 105° C. for 16 h. The mixture was cooled to room temperature, filtered through celite, followed by washing with CH$_2$Cl$_2$. The solvent was evaporated under reduced pressure. The residue was purified by column chromatography (16% EA in hexane as eluent) to obtain intermediate 9 (170 mg, 37%).

$^1$H NMR (400 MHz, CDCl$_3$): δ 7.05 (td, J=6.2, 2.0 Hz, 1H), 6.96-6.81 (m, 3H), 3.85 (s, 3H), 3.70-3.10 (m, 6H), 2.82-2.70 (m, 1H), 1.48 (s, 9H), 0.89 (d, J=6.3 Hz, 3H).

ESI-MS C$_{17}$H$_{26}$N$_2$O$_3$: 306.2, found: 308.4 (M+H$^+$)$^+$, 329.4 (M+Na$^+$)$^+$.

Step 2

Intermediate 9 (170 mg, 0.55 mmol) was dissolved in 2 mL CH$_2$Cl$_2$, then the reaction was added 1 mL TFA slowly at 0° C. The reaction was stirred for 16 h at room temperature. The reaction mixture was quenched by 1N NaOH$_{(aq.)}$ to pH>7 and extracted by CH$_2$Cl$_2$. The organic layer was dried over MgSO$_4$, filtered and concentrated to afford intermediate 10, which was used directly in the next step.

ESI-MS C$_{12}$H$_{18}$N$_2$O: 206.1, found: 207.7 (M+H$^+$)$^+$, 229.4 (M+Na$^+$)$^+$.

Step 3

Intermediate 10, 2-bromoacetic acid (84 mg, 0.61 mmol), EDC (127 mg, 0.66 mmol) and DMAP (13 mg, 0.11 mmol) were dissolved in 2 mL DMF, and then stirred at room temperature for 16 hours. The reaction mixture was extracted with H$_2$O and CH$_2$Cl$_2$. The organic layer was dried over MgSO$_4$, filtered and concentrated to afford Intermediate 30 for use in the next step.

ESI-MS C$_{14}$H$_{19}$BrN$_2$O$_2$: 326.1, found: 327.2 (M+H$^+$)$^+$, 349.2 (M+Na$^+$)$^+$.

Step 4

Intermediate 30, 6-propyl-2-thiouracil (80 mg, 0.47 mmol) and K$_2$CO$_3$ (89 mg, 0.64 mmol) were dissolved in 4 mL CH$_2$Cl$_2$ and MeOH (1:1), and then stirred at 80° C. for 4 hours. After the reaction mixture was cooled off, the K$_2$CO$_3$ was filtered through filter paper. Filtrate was collected and concentrated to obtain crude. The crude was purified by column chromatography (10% MeOH in CH$_2$Cl$_2$ as eluent) to obtain Compound 28 as a white solid (143 mg, 62% over 3 steps).

$^1$H NMR (400 MHz, CDCl$_3$): δ 7.14-7.04 (m, 1H), 7.01-6.86 (m, 3H), 6.04 (s, 1H), 4.08 (s, 2H), 4.17-3.96 (m, 1H), 3.86 (s, 3H), 3.81-3.75 (m, 1H), 3.74-3.68 (m, 1H), 3.47-3.37 (m, 1H), 3.34-3.18 (m, 1H), 2.99-2.81 (m, 1H), 2.44 (t, J=7.5 Hz, 2H), 1.65 (sextet, J=7.5 Hz, 2H), 0.95 (t, J=7.5 Hz, 3H), 0.90 (d, J=6.4 Hz, 3H).

ESI-MS C$_{21}$H$_{28}$N$_4$O$_3$S: 416.2, found: 417.2 (M+H$^+$)$^+$, 439.2 (M+Na$^+$)$^+$.

Example 29: 2-((4-phenylpiperazin-1-yl)methyl)-5-propyl-[1,2,4]triazolo[1,5-a]pyrimidin-7(4H)-one (Compound 29)

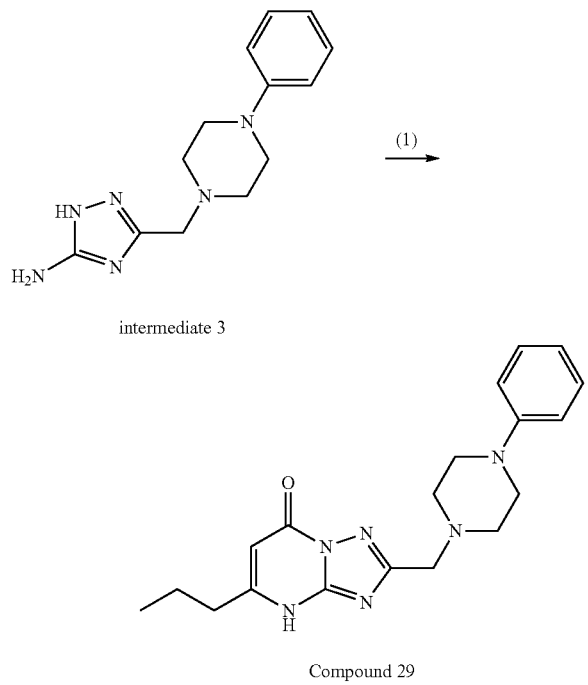

intermediate 3

Compound 29

Reagents and conditions: 3-oxo-hexanoic acid ethyl ester, AcOH, reflux, 16 h, and yield 40%.

Intermediate 3 (166 mg, 0.64 mmol) and 3-oxo-hexanoic acid ethyl ester (0.2 mL, 1.02 mmol) were dissolved in 1 mL acetic acid and heated at reflux for 16 hours. After the solvent was removed, the reaction mixture was neutralized by saturated sodium bicarbonate solution and extracted by dicholoromethane. The organic layers were collected, dried over MgSO$_4$, filtered and concentrated to afford a crude, which was purified by column chromatography to afford Compound 29 as a pale-yellow solid (91.1 mg, 40%).

$^1$H NMR (400 MHz, DMSO) δ 7.19 (t, J=7.2 Hz, 2H), 6.92 (d, J=7.2 Hz, 2H), 6.76 (t, J=7.2 Hz, 1H), 5.77 (s, 1H), 3.66 (s, 2H), 3.12 (t, J=5.1 Hz, 4H), 2.66 (t, J=5.1 Hz, 4H), 2.54 (t, J=7.6 Hz, 2H), 1.66 (sextet, J=7.4 Hz, 2H), 0.91 (t, J=7.4 Hz, 3H).

ESI-MS C$_{19}$H$_{24}$N$_6$O: 352.2, found: 353.2 (M+H$^+$)$^+$, 375.2 (M+Na$^+$)$^+$.

Example 30: 6-cyclopropyl-2-((2-(4-(2-methoxyphenyl)piperazin-1-yl)-2-oxoethyl)thio)pyrimidin-4(3H)-one (Compound 30)

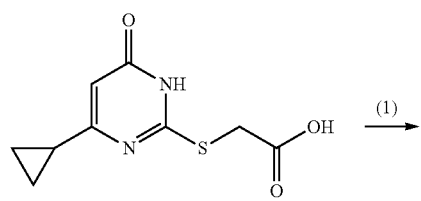

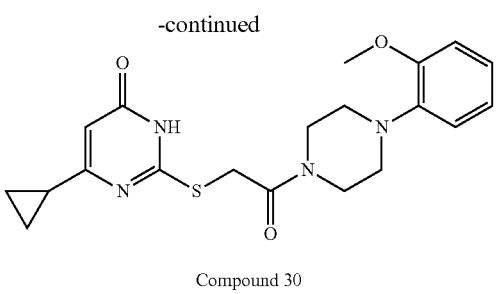

Compound 30

Reagents and conditions: 1-(2-methoxy-phenyl)-piperazine, EDC, DMAP, DMF, r.t., 48 h, and yield 64%.

(4-Cyclopropyl-6-oxo-1,6-dihydro-pyrimidin-2-ylsulfanyl)-acetic acid (100 mg, 0.44 mmol), 1-(2-methoxy-phenyl)-piperazine (102 mg, 0.53 mmol), EDC (101.7 mg, 0.53 mmol) and DMAP (16.2 mg, 0.13 mmol) were dissolved in 5 mL DMF, and then stirred at room temperature for 48 hours. After the solvent was removed, the reaction mixture was diluted with EtOAc, washed sequentially with water and brine. The organic layer was dried over MgSO$_4$, filtered and concentrated to afford a crude, which was purified by column chromatography (gradient elution: 5% to 10% MeOH in CH$_2$Cl$_2$) to give Compound 30 as a pale-yellow solid (112.6 mg, 64%).

$^1$H NMR (400 MHz, DMSO) δ 7.04-6.92 (m, 2H), 6.91-6.85 (m, 2H), 6.01 (s, 1H), 4.11 (s, 2H), 3.80 (s, 3H), 3.68 (t, J=5.0 Hz, 2H), 3.60 (t, J=5.0 Hz, 2H), 3.00 (t, J=5.0 Hz, 2H), 2.93 (t, J=5.0 Hz, 2H), 1.84-1.74 (m, 1H), 0.98-0.76 (m, 4H).

ESI-MS C$_{20}$H$_{24}$N$_4$O$_3$S: 400.2, found: 401.2 (M+H$^+$)$^+$, 423.2 (M+Na$^+$)$^+$.

Example 31: 5-isopropyl-2-((4-(2-methoxyphenyl)piperazin-1-yl)methyl)-[1,2,4]triazolo[1,5-a]pyrimidin-7(4H)-one (Compound 31)

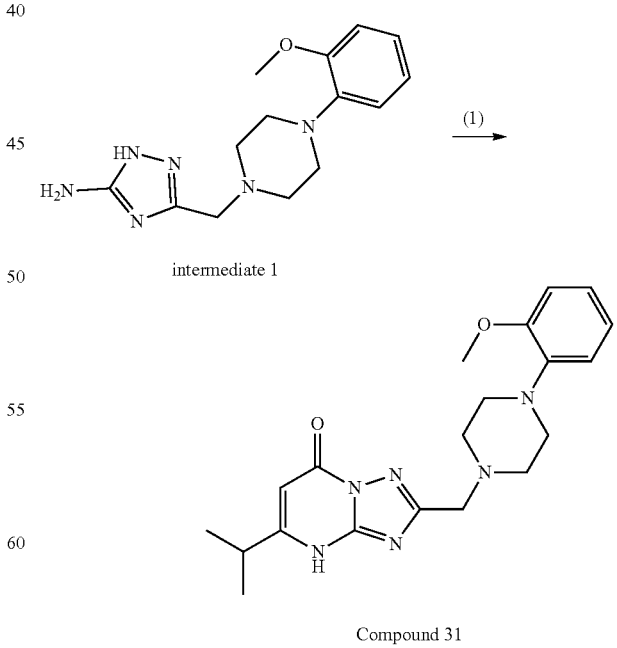

intermediate 1

Compound 31

Reagents and conditions: 4-methyl-3-oxo-pentanoic acid ethyl ester, AcOH, reflux, 16 h, and yield 17%.

Intermediate 1 (100 mg, 0.35 mmol) and 4-methyl-3-oxopentanoic acid ethyl ester (0.06 mL, 0.35 mmol) were dissolved in 1 mL acetic acid and heated at reflux for 16 hours. After the solvent was removed, the reaction mixture was neutralized by saturated sodium bicarbonate solution and extracted by dicholoromethane. The organic layers were collected, dried over MgSO$_4$, filtered and concentrated to afford a crude, which was purified by column chromatography to afford Compound 31 as a pale-yellow solid (22.6 mg, 17%).

$^1$H NMR (300 MHz, DMSO) δ 6.98-6.76 (m, 4H), 5.73 (s, 1H), 3.75 (s, 3H), 3.68 (s, 2H), 3.02-2.88 (m, 4H), 2.82 (septet, J=6.9 Hz, 1H), 2.73-2.62 (m, 4H), 1.23 (d, J=6.9 Hz, 6H).

ESI-MS C$_{20}$H$_{26}$N$_6$O$_2$: 382.2, found: 383.2 (M+H$^+$)$^+$, 405.2 (M+Na$^+$)$^+$.

Example 32: 6-(3-chlorobenzyl)-2-((4-(2-methoxyphenyl)piperazin-1-yl)methyl)-5-methyl-[1,2,4]triazolo[1,5-a]pyrimidin-7(3H)-one (Compound 32)

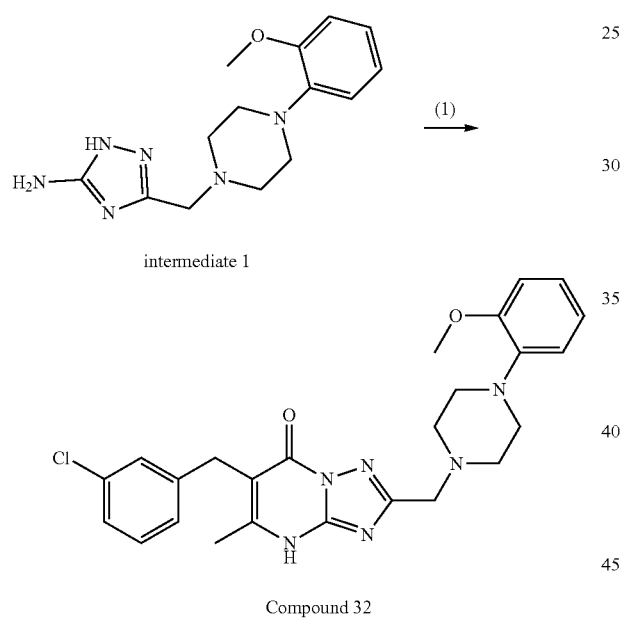

Compound 32

Reagents and conditions: 2-(3-chloro-benzyl)-3-oxo-butyric acid ethyl ester, AcOH, reflux, 16 h, and yield 14%.

Intermediate 1 (100 mg, 0.35 mmol) and 2-(3-chlorobenzyl)-3-oxo-butyric acid ethyl ester (88.3 mg, 0.35 mmol) were dissolved in 1 mL acetic acid and heated at reflux for 16 hours. After the solvent was removed, the reaction mixture was neutralized by saturated sodium bicarbonate solution and extracted by dicholoromethane. The organic layers were collected, dried over MgSO$_4$, filtered and concentrated to afford a crude, which was purified by column chromatography to afford Compound 32 as a pale-yellow solid (23.3 mg, 14%).

$^1$H NMR (400 MHz, DMSO) δ 7.30-7.25 (m, 2H), 7.24-7.18 (m, 2H), 6.97-6.80 (m, 4H), 3.85 (s, 2H), 3.75 (s, 3H), 3.66 (s, 2H), 3.00-2.90 (m, 4H), 2.70-2.62 (m, 4H), 2.28 (s, 3H).

ESI-MS C$_{25}$H$_{27}$ClN$_6$O$_2$: 478.2, found: 479.2 (M+H$^+$)$^+$, 501.2 (M+Na$^+$)$^+$.

Example 33: 6-(3-chlorobenzyl)-2-(1-(4-(2-methoxyphenyl)piperazin-1-yl)ethyl)-5-methyl-[1,2,4]triazolo [1,5-a]pyrimidin-7(3H)-one (Compound 33)

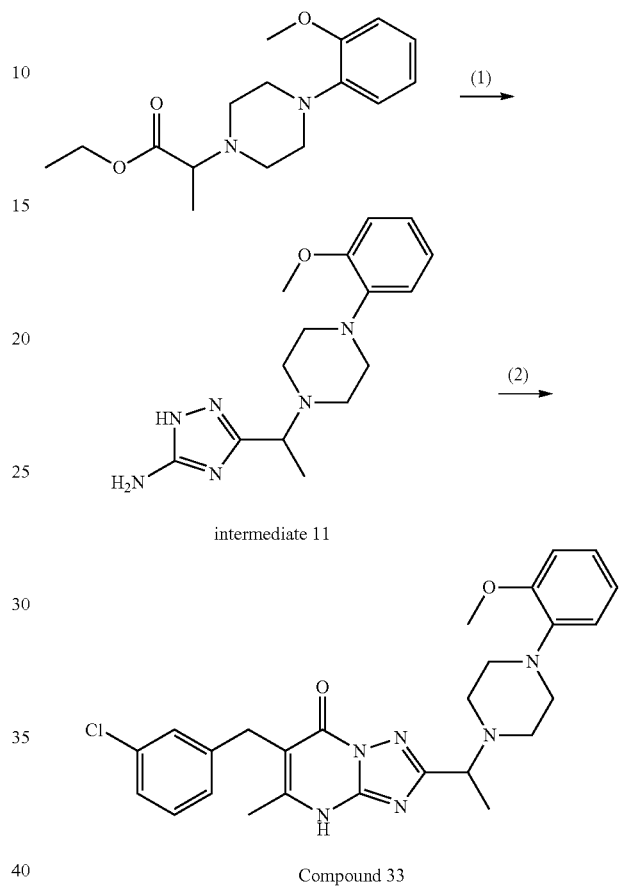

intermediate 11

Compound 33

Reagents and conditions: (1) aminoguanidine bicarbonate, DMSO, 140° C., 16 h, and yield 9%, and (2) 2-(3-chloro-benzyl)-3-oxo-butyric acid ethyl ester, toluene, reflux by Dean-Stark, 16 h, and yield 4%.

Step 1

Aminoguanidine bicarbonate (0.99 g, 0.72 mmol) and 2-[4-(2-methoxy-phenyl)-piperazin-1-yl]-propionic acid ethyl ester (1.01 g, 0.36 mmol) were dissolved in 5 mL DMSO and heated at 140° C. for 16 hours. After the solvent was removed, the reaction mixture was purified by column chromatography to give intermediate 11 as a yellow solid (100 mg, 9%).

$^1$H NMR (400 MHz, DMSO) δ 7.12-7.00 (m, 1H), 6.51-6.25 (m, 3H), 5.76 (s, 2H), 3.69 (s, 3H), 3.61-3.55 (m, 1H), 3.13-2.97 (m, 4H), 2.61-2.40 (m, 4H), 1.31 (d, J=7.0 Hz, 3H).

ESI-MS C$_{15}$H$_{22}$N$_6$O: 302.2, found: 303.1 (M+H$^+$)$^+$, 326.1 (M+Na$^+$)$^+$.

Step 2

Intermediate 11 (118.9 mg, 0.39 mmol) and 2-(3-chlorobenzyl)-3-oxo-butyric acid ethyl ester (100 mg, 0.39 mmol)

were dissolved in 3 mL toluene and heated at reflux by Dean-Stark for 16 hours. After the solvent was removed, the reaction mixture was purified by column chromatography to afford Compound 33 as a pale-yellow solid (8.4 mg, 4%).

$^1$H NMR (400 MHz, DMSO): δ 7.31-7.16 (m, 4H), 7.07 (t, J=8.2 Hz, 1H), 6.47 (dd, J=8.3, 2.2 Hz, 1H), 6.39 (t, J=1.8 Hz, 1H), 6.33 (dd, J=8.4, 1.9 Hz, 1H), 3.92-3.86 (m, 1H), 3.84 (s, 2H), 3.69 (s, 3H), 3.16-3.00 (m, 4H), 2.71-2.56 (m, 4H), 2.26 (s, 3H), 1.43 (d, J=6.9 Hz, 3H).

ESI-MS $C_{26}H_{29}ClN_6O_2$: 492.2, found: 493.1 (M+H$^+$)$^+$, 515.0 (M+Na$^+$)$^+$.

Example 34: 6-(3-chlorobenzyl)-5-methyl-2-((1-phenylpiperidin-4-ylidene)methyl)-[1,2,4]triazolo[1,5-a] pyrimidin-7(4H)-one (Compound 34)

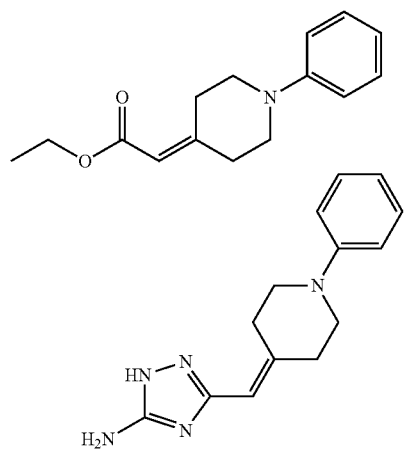

intermediate 12

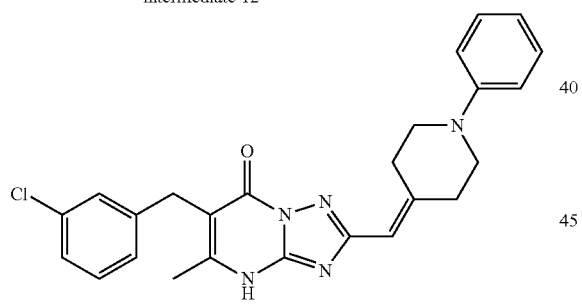

Compound 34

Reagents and conditions: (1) aminoguanidine bicarbonate, n-BuOH, 140° C., 16 h, and yield 31%, and (2) 2-(3-chloro-benzyl)-3-oxo-butyric acid ethyl ester, toluene, reflux by Dean-Stark, 16 h, and yield 15%.

Step 1

(1-Phenyl-piperidin-4-ylidene)-acetic acid ethyl ester (437.5 mg, 1.78 mmol) and aminoguanidine bicarbonate (485.9 mg, 3.56 mmol) were dissolved in 5 mL n-BuOH and heated at 140° C. for 16 hours. After the solvent was removed, the reaction mixture was purified by column chromatography to give intermediate 12 as a yellow solid (140 mg, 31%).

$^1$H NMR (400 MHz, DMSO) δ 11.65 (s, 1H), 7.19 (t, J=7.3 Hz, 2H), 6.90 (d, J=7.3 Hz, 2H), 6.71 (t, J=7.3 Hz, 1H), 5.77 (s, 2H), 5.55 (s, 1H), 3.64-3.56 (m, 2H), 3.28 (t, J=5.7 Hz, 2H), 3.18-3.09 (m, 2H), 2.19-2.12 (m, 2H).

ESI-MS $C_{14}H_{17}N_5$: 255.2, found: 256.1 (M+H$^+$)$^+$, 278.1 (M+Na$^+$)$^+$.

Step 2

Intermediate 12 (100 mg, 0.39 mmol) and 2-(3-chlorobenzyl)-3-oxo-butyric acid ethyl ester (99.5 mg, 0.39 mmol) were dissolved in 3 mL toluene and heated at reflux by Dean-Stark for 16 hours. After the solvent was removed, the reaction mixture was purified by column chromatography to afford Compound 34 as a pale-yellow solid (26.8 mg, 15%).

$^1$H NMR (400 MHz, DMSO) δ 7.33-7.13 (m, 6H), 6.90 (d, J=7.1 Hz, 2H), 6.71 (t, J=7.1 Hz, 1H), 5.65 (s, 1H), 3.84 (s, 2H), 3.65-3.57 (m, 2H), 3.47-3.40 (m, 2H), 3.30 (t, J=5.7 Hz, 2H), 2.29 (s, 3H), 2.26-2.19 (m, 2H).

ESI-MS $C_{25}H_{24}ClN_5O$: 445.2, found: 446.1 (M+H$^+$)$^+$, 468.1 (M+Na$^+$)$^+$.

Example 35: 6-(3-chlorobenzyl)-5-methyl-2-(6-phenyl-6-azaspiro[2.5]octan-1-yl)-[1,2,4]triazolo[1,5-a] pyrimidin-7(4H)-one (Compound 35)

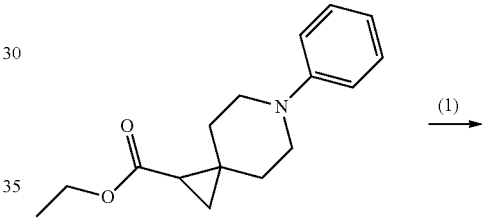

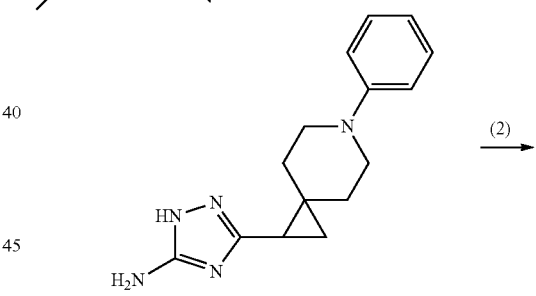

intermediate 13

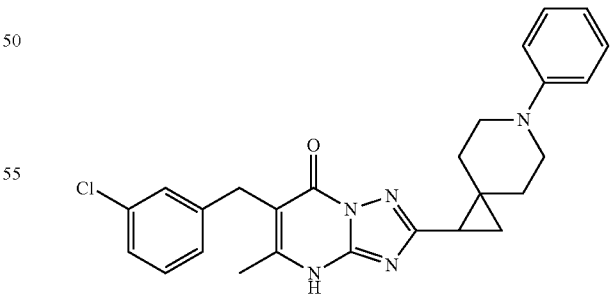

Compound 35

Reagents and conditions: (1) aminoguanidine bicarbonate, n-BuOH, 140° C., 16 h, and yield 4%, and (2) 2-(3-chloro-benzyl)-3-oxo-butyric acid ethyl ester, toluene, reflux by Dean-Stark, 16 h, and yield 5%.

Step 1

6-Phenyl-6-aza-spiro[2.5]octane-1-carboxylic acid ethyl ester (1.2 g, 0.45 mmol) and aminoguanidine bicarbonate (1.2 g, 0.9 mmol) were dissolved in 20 mL n-BuOH and heated at reflux for 16 hours. After the solvent was removed, the reaction mixture was purified by column chromatography to give intermediate 13 as a yellow solid (48 mg, 4%).

ESI-MS $C_{15}H_{19}N_5$: 269.2, found: 270.1 $(M+H^+)^+$, 292.1 $(M+Na^+)^+$.

Step 2

Intermediate 13 (48 mg, 0.18 mmol) and 2-(3-chlorobenzyl)-3-oxo-butyric acid ethyl ester (54.3 mg, 0.21 mmol) were dissolved in 5 mL toluene and heated at reflux by Dean-Stark for 16 hours. After the solvent was removed, the reaction mixture was purified by column chromatography to afford Compound 35 as a pale-yellow solid (4.4 mg, 5%).

$^1$H NMR (400 MHz, DMSO): δ 7.35-7.12 (m, 6H), 6.91 (d, J=7.4 Hz, 2H), 6.73 (t, J=7.4 Hz, 1H), 3.83 (s, 2H), 3.31-3.17 (m, 2H), 3.14-3.04 (m, 1H), 2.95-2.84 (m, 1H), 2.27 (s, 3H), 2.09-2.00 (m, 1H), 1.79-1.54 (m, 4H), 1.21-1.16 (m, 1H), 1.07-1.01 (m, 1H).

ESI-MS $C_{26}H_{26}ClN_5O$: 459.2, found: 460.2 $(M+H^+)^+$, 482.2 $(M+Na^+)^+$.

Example 36: 6-isopropyl-2-((2-(4-(thiazol-2-yl)piperazin-1-yl)ethyl)thio)pyrimidin-4(3H)-one (Compound 36)

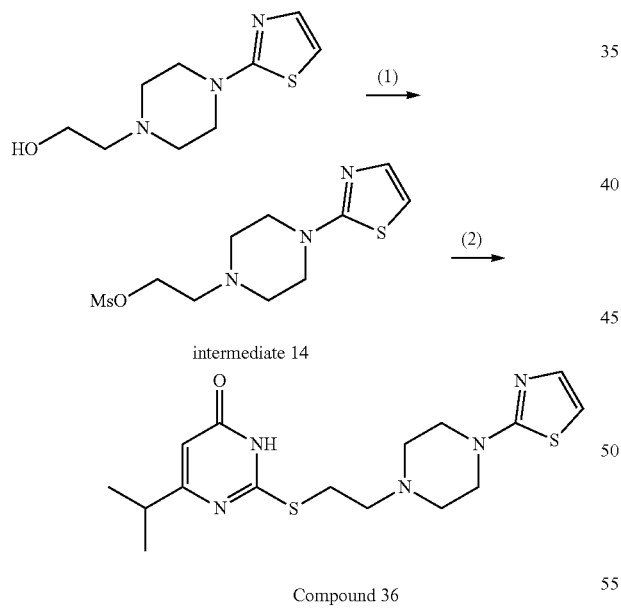

Reagents and conditions: (1) MsCl, Et$_3$N, THF, r.t., 4 h, and (2) 6-isopropyl-2-mercaptopyrimidin-4(3H)-one, KOH, EtOH, reflux, 16 h, 34% over 2 steps.

Step 1

2-(4-(Thiazol-2-yl)piperazin-1-yl)ethanol (120 mg, 0.56 mmol), mesyl chloride (0.05 mL, 0.68 mmol) and Et$_3$N (0.5 mL) were dissolved in 5 mL THF, and then stirred at room temperature for 4 hours. The reaction mixture was extracted with H$_2$O and CH$_2$Cl$_2$. The organic layer was dried over MgSO$_4$, filtered and concentrated to afford intermediate 14 for use directly in the next step.

Step 2

Intermediate 14, 6-isopropyl-2-mercaptopyrimidin-4 (3H)-one (76 mg, 0.45 mmol) and KOH (50 mg, 0.9 mmol) were dissolved in EtOH. The resultant mixture was stirred and refluxed for 16 h. After the reaction cooled off, the mixture was extracted with H$_2$O and CH$_2$Cl$_2$. The organic layer was dried over MgSO$_4$, filtered and concentrated to afford a crude, which was purified by flash column chromatography (10% MeOH in CH$_2$Cl$_2$ as eluent) to obtain Compound 36 (62 mg, 34% over 2 steps).

$^1$H NMR (400 MHz, CDCl$_3$): δ 7.20 (d, J=3.6 Hz, 1H), 6.58 (d, J=3.6 Hz, 1H), 6.03 (d, J=0.6 Hz, 1H), 3.66 (t, J=4.5 Hz, 4H), 3.27 (t, J=6.3 Hz, 2H), 2.85 (t, J=6.3 Hz, 2H), 2.73 (t, J=4.5 Hz, 4H), 2.71-2.65 (m, 1H), 1.20 (d, J=6.9 Hz, 6H).

ESI-MS $C_{16}H_{23}N_5OS_2$: 365.1, found: 366.2 $(M+H^+)^+$, 388.1 $(M+Na^+)^+$.

Example 37: 2-((2-(4-(2-methoxyphenyl)piperazin-1-yl)-2-oxoethyl)amino)-6-propylpyrimidin-4(3H)-one (Compound 37)

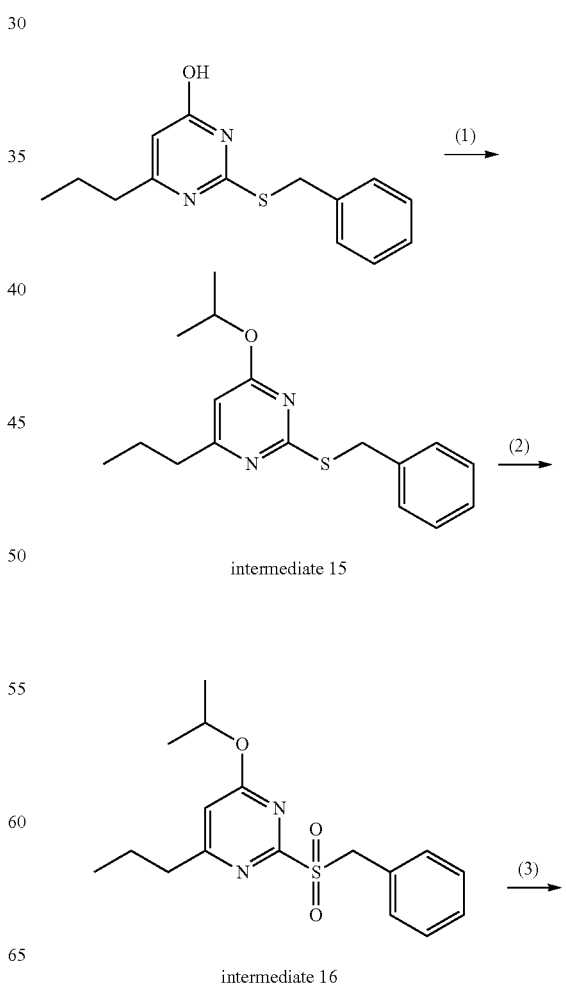

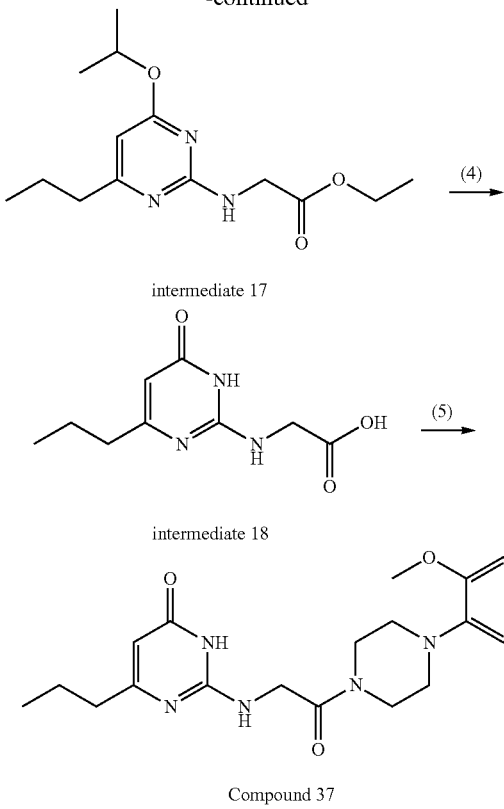

intermediate 17 intermediate 18

Compound 37

Reagents and conditions: (1) i-PrOH, PPh$_3$, DIAD, THF, r.t., 4 h, and yield 92%; (2) m-CPBA, CH$_2$Cl$_2$, 0° C., 1.5 h, and yield 99%; (3) glycine ethyl ester hydrochloride, DIPEA, dioxane, reflux, 40 h; (4) HCl, H$_2$O, 100° C., 16 h; and (5) 1-(2-methoxyphenyl)-piperazine, EDC, DMAP, DMF, r.t., 16 h, 60%, over 3 steps.

Step 1

2-(Benzylthio)-6-propylpyrimidin-4-ol (257.8 mg, 0.99 mmol), PPh$_3$ (312.1 mg, 1.19 mmol) and i-PrOH (71.5 mg, 1.19 mmol) were dissolved in 2 mL THF. A solution of DIAD (240.6 mg, 1.19 mmol) in 1 mL THF was added to the reaction mixture slowly at room temperature and stirred for 4 hours. Solvent was removed to afford a crude, which was purified by column chromatography to give intermediate 15 as a yellow oil (275.7 mg, 92%).

$^1$H NMR (300 MHz, DMSO) δ 7.41 (d, J=7.2 Hz, 2H), 7.36-7.18 (m, 3H), 6.39 (s, 1H), 5.33-5.20 (m, 1H), 4.37 (s, 2H), 2.52 (t, J=7.4 Hz, 2H), 1.63 (d, J=7.4 Hz, 2H), 1.26 (d, J=6.1 Hz, 6H), 0.88 (t, J=7.4 Hz, 3H).

ESI-MS C$_{17}$H$_{22}$N$_2$OS: 302.2, found: 303.1 (M+H$^+$)$^+$, 325.1 (M+Na$^+$)$^+$.

Step 2

Intermediate 15 (275.7 mg, 0.91 mmol) was dissolved in 4.5 mL CH$_2$Cl$_2$, followed by addition of m-CPBA (393.4 mg, 2.28 mmol) slowly at 0° C. The resultant reaction mixture was stirred for 1.5 hour, diluted with CH$_2$Cl$_2$, and washed by saturated NaHCO$_{3(aq.)}$ and brine. The organic layer was dried over MgSO$_4$, filtered and concentrated to afford intermediate 16 as a yellow oil without further purification (301 mg, 99%).

$^1$H NMR (400 MHz, DMSO) δ 7.34 (s, 5H), 7.01 (s, 1H), 5.33 (septet, J=6.2 Hz, 1H), 4.91 (s, 2H), 2.71 (t, J=7.4 Hz, 2H), 1.69 (sextet, J=7.4 Hz, 2H), 1.32 (d, J=6.2 Hz, 6H), 0.90 (t, J=7.4 Hz, 3H).

ESI-MS C$_{17}$H$_{22}$N$_2$O$_3$S: 334.1, found: 335.1 (M+H$^+$)$^+$, 357.1 (M+Na$^+$)$^+$.

Step 3

Intermediate 16 (100 mg, 0.3 mmol), glycine ethyl ester hydrochloride (250 mg, 1.79 mmol), DIPEA (0.3 mL, 1.79 mmol) were stirred in 2 mL dioxane and refluxed for 40 hours. The reaction mixture was extracted with H$_2$O and CH$_2$Cl$_2$. The organic layer was dried over MgSO$_4$, filtered and concentrated to afford a crude. The crude residue was purified by column chromatography (16% EA in hexane as eluent) to obtain intermediate 17 for use directly in the next step.

ESI-MS C$_{14}$H$_{23}$N$_3$O$_3$: 281.2, found: 282.2 (M+H$^+$)$^+$, 304.2 (M+Na$^+$)$^+$.

Step 4

Intermediate 17 (100 mg, 0.36 mmol) was dissolved in 6N HCl$_{(aq.)}$ and stirred at 100° C. for 16 hours. The solvent was removed to obtain intermediate 18, which was used directly in the next step.

ESI-MS C$_9$H$_{13}$N$_3$O$_3$: 211.1, found: 212.5 (M+H$^+$)$^+$, 234.1 (M+Na$^+$)$^+$.

Step 5

Intermediate 18, 1-(2-methoxyphenyl)-piperazine (74 mg, 0.39 mmol), EDC (80 mg, 0.42 mmol) and DMAP (8 mg, 0.07 mmol) were dissolved in 1 mL DMF, and then stirred at room temperature for 16 hours. The reaction mixture was extracted with H$_2$O and CH$_2$Cl$_2$. The organic layer was dried over MgSO$_4$, filtered and concentrated to afford a crude, which was purified by column chromatography (10% MeOH in CH$_2$Cl$_2$ as eluent) to obtain Compound 37 as a light-yellow solid (28 mg, 60% over 3 steps).

$^1$H NMR (400 MHz, CDCl$_3$): δ 7.10-6.99 (m, 1H), 6.98-6.84 (m, 3H), 5.70 (s, 1H), 4.30 (s, 2H), 3.94 (t, J=5.2 Hz, 2H), 3.88 (s, 3H), 3.70 (t, J=5.2 Hz, 2H), 3.64 (s, 1H), 3.15-3.03 (m, 4H), 2.37 (t, J=7.4 Hz, 2H), 1.65 (sextet, J=7.4 Hz, 2H), 0.94 (t, J=7.4 Hz, 3H).

ESI-MS C$_{20}$H$_{27}$N$_5$O$_3$: 385.2, found: 386.2 (M+H$^+$)$^+$, 408.2 (M+Na$^+$)$^+$.

Example 38: 6-isopropyl-2-((1-((S)-3-methyl-4-(thiazol-2-yl)piperazin-1-yl)-1-oxopropan-2-yl)thio)pyrimidin-4(3H)-one (Compound 38)

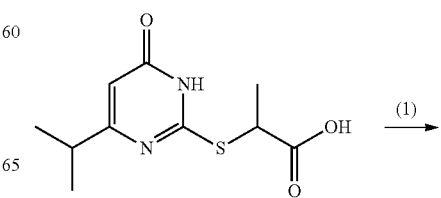

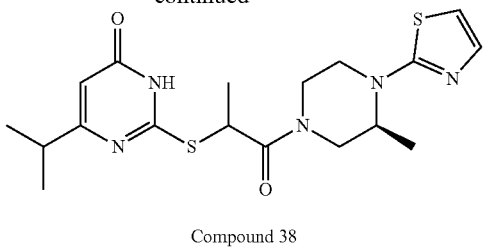

Compound 38

Reagents and conditions: (S)-2-(2-methylpiperazin-1-yl) thiazole, EDC, DMAP, DMF, r.t., 16 h, and yield 86%.

2-((4-Isopropyl-6-oxo-1,6-dihydropyrimidin-2-yl)thio) propanoic acid (57 mg, 0.23 mmol), (S)-2-(2-methylpiperazin-1-yl)thiazole (38.5 mg, 0.21 mmol), EDC (49 mg, 0.25 mmol) and DMAP (5 mg, 0.04 mmol) were dissolved in 2 mL DMF, and then stirred at room temperature for 16 hours. The reaction mixture was extracted with $H_2O$ and $CH_2Cl_2$. The organic layer was dried over $MgSO_4$, filtered and concentrated to afford a crude, which was purified by column chromatography (10% MeOH in $CH_2Cl_2$ as eluent) to obtain Compound 38 as a light-yellow solid (74 mg, 86%).

$^1$H NMR (400 MHz, $CDCl_3$): δ 7.22-7.16 (m, 1H), 6.63-6.58 (m, 1H), 6.11-6.05 (m, 1H), 5.16-4.95 (m, 1H), 4.69-4.30 (m, 1.5H), 4.23-3.74 (m, 2.5H), 3.71-3.23 (m, 3H), 3.16-2.86 (m, 1H), 2.72 (septet, J=6.7 Hz, 1H), 1.64 (d, J=6.7 Hz, 3H), 1.28 (d, J=7.6 Hz, 3H), 1.21 (d, J=6.7 Hz, 6H).

ESI-MS $C_{18}H_{25}N_5O_2S_2$: 407.1, found: 408.1 $(M+H^+)^+$, 430.0 $(M+Na^+)^+$.

Example 39: 2-((1-(4-(2-methoxyphenyl)piperazin-1-yl)-1-oxopropan-2-yl)thio)-6-propylpyrimidin-4(3H)-one (Compound 39)

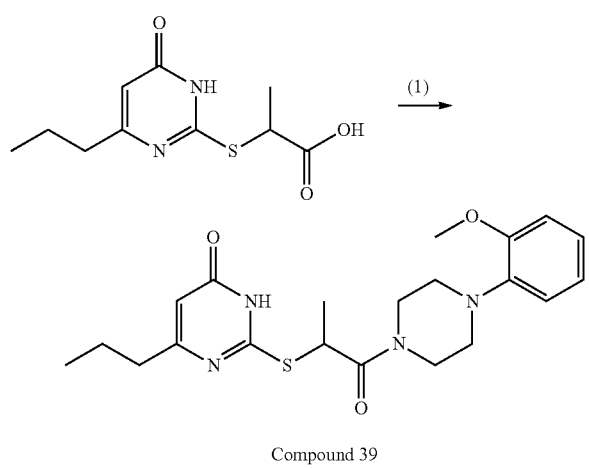

Compound 39

Reagents and conditions: 1-(2-methoxylphenyl) piperazine, EDC, DMAP, DMF, r.t., 16 h, and yield 95%.

2-((6-Oxo-4-propyl-1,6-dihydropyrimidin-2-yl)thio)propanoic acid (100 mg, 0.41 mmol), 1-(2-methoxylphenyl) piperazine (87 mg, 0.45 mmol), EDC (96 mg, 0.5 mmol) and DMAP (10 mg, 0.08 mmol) were dissolved in 2 mL DMF, and then stirred at room temperature for 16 hours. The reaction mixture was extracted with $H_2O$ and $CH_2Cl_2$. The organic layer was dried over $MgSO_4$, filtered and concentrated to afford a crude, which was purified by column chromatography (10% MeOH in $CH_2Cl_2$ as eluent) to obtain Compound 39 as a white solid (163 mg, 95%).

$^1$H NMR (400 MHz, $CDCl_3$): δ 7.13-7.01 (m, 1H), 6.99-6.83 (m, 3H), 6.04 (s, 1H), 5.00 (q, J=7.0 Hz, 1H), 3.88 (s, 3H), 3.92-3.70 (m, 4H), 3.21-2.96 (m, 4H), 2.46 (t, J=6.7 Hz, 2H), 1.74-1.63 (m, 2H), 1.64 (d, J=7.0 Hz, 3H), 0.95 (t, J=6.7 Hz, 3H).

ESI-MS $C_{21}H_{28}N_4O_3S$: 416.2, found: 417.2 $(M+H^+)^+$, 439.1 $(M+Na^+)^+$.

Example 40: 2-((1-(4-(2-methoxyphenyl)piperazin-1-yl)-3-methyl-1-oxobutan-2-yl)thio)-6-propylpyrimidin-4(3H)-one (Compound 40)

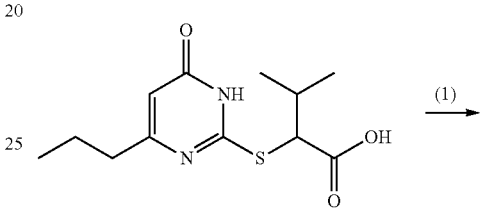

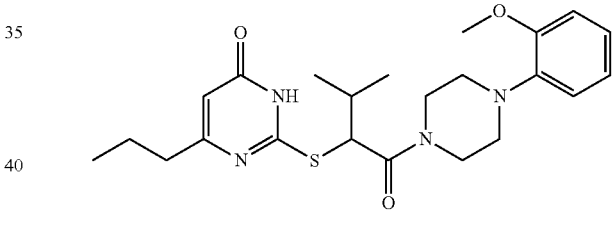

Compound 40

Reagents and conditions: 1-(2-methoxylphenyl) piperazine, EDC, DMAP, DMF, r.t., 16 h, and yield 50%.

3-Methyl-2-((6-oxo-4-propyl-1,6-dihydropyrimidin-2-yl) thio)butanoic acid (100 mg, 0.37 mmol), 1-(2-methoxylphenyl) piperazine (78 mg, 0.41 mmol), EDC (85 mg, 0.44 mmol) and DMAP (9 mg, 0.07 mmol) were dissolved in 2 mL DMF, and then stirred at room temperature for 16 hours. The reaction mixture was extracted with $H_2O$ and $CH_2Cl_2$. The organic layer was dried over $MgSO_4$, filtered and concentrated to afford a crude, which was purified by column chromatography (10% MeOH in $CH_2Cl_2$ as eluent) to obtain Compound 40 as a white solid (83 mg, 50%).

$^1$H NMR (400 MHz, $CDCl_3$): δ 7.11-7.00 (m, 1H), 6.97-6.83 (m, 3H), 6.03 (s, 1H), 4.79 (d, J=8.7 Hz, 1H), 3.88 (s, 3H), 3.95-3.75 (m, 4H), 3.16-2.94 (m, 4H), 2.44 (t, J=7.4 Hz, 2H), 2.39-2.30 (m, 1H), 1.72-1.60 (m, 2H), 1.11 (d, J=6.7 Hz, 3H), 1.07 (d, J=6.7 Hz, 3H), 0.94 (t, J=7.4 Hz, 3H).

ESI-MS $C_{23}H_{32}N_4O_3S$: 444.2, found: 445.2 $(M+H^+)^+$, 467.1 $(M+Na^+)^+$.

Example 41: 2-((1-oxo-1-(4-phenylpiperazin-1-yl)pentan-2-yl)thio)-6-propylpyrimidin-4(3H)-one (Compound 41)

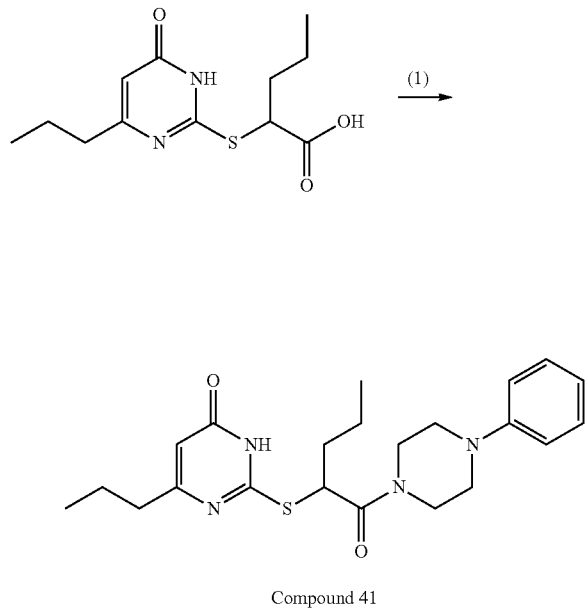

Compound 41

Reagents and conditions: 1-phenyl piperazine, EDC, DMAP, DMF, r.t., 16 h, and yield 73%.

2-((6-Oxo-4-propyl-1,6-dihydropyrimidin-2-yl)thio)pentanoic acid (100 mg, 0.37 mmol), 1-phenyl piperazine (78 mg, 0.41 mmol), EDC (85 mg, 0.44 mmol) and DMAP (9 mg, 0.07 mmol) were dissolved in 2 mL DMF, and then stirred at room temperature for 16 hours. The reaction mixture was extracted with $H_2O$ and $CH_2Cl_2$. The organic layer was dried over $MgSO_4$, filtered and concentrated to afford a crude, which was purified by column chromatography (10% MeOH in $CH_2Cl_2$ as eluent) to obtain Compound 41 as a white solid (112 mg, 73%).

$^1$H NMR (400 MHz, CDCl$_3$): δ 7.29 (t, J=7.7 Hz, 2H), 7.03-6.82 (m, 3H), 6.04 (s, 1H), 4.97 (t, J=7.5 Hz, 1H), 3.91-3.68 (m, 4H), 3.31-3.08 (m, 4H), 2.45 (t, J=7.5 Hz, 2H), 2.17-1.98 (m, 1H), 1.92-1.78 (m, 1H), 1.76-1.59 (m, 4H), 1.53-1.34 (m, 2H), 1.02-0.76 (m, 6H).

ESI-MS $C_{22}H_{30}N_4O_2S$: 414.2, found: 415.2 (M+H$^+$)$^+$, 437.2 (M+Na$^+$)$^+$.

Example 42: 2-((1-(4-(2-methoxyphenyl)piperazin-1-yl)-1-oxopentan-2-yl)thio)-6-propylpyrimidin-4(3H)-one (Compound 42)

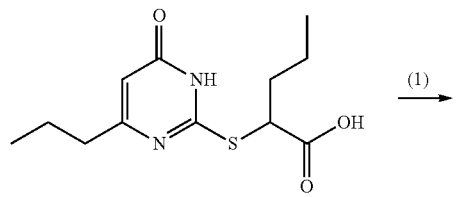

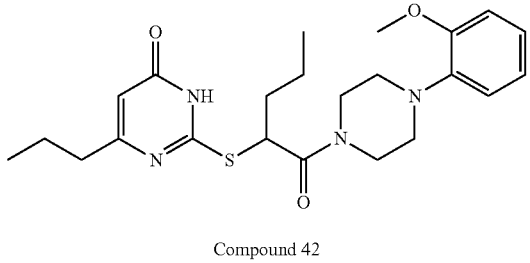

Compound 42

Reagents and conditions: 1-(2-methoxylphenyl) piperazine, EDC, DMAP, DMF, r.t., 16 h, and yield 80%.

2-((6-Oxo-4-propyl-1,6-dihydropyrimidin-2-yl)thio)pentanoic acid (100 mg, 0.37 mmol), 1-(2-methoxylphenyl) piperazine (78 mg, 0.41 mmol), EDC (85 mg, 0.44 mmol) and DMAP (9 mg, 0.07 mmol) were dissolved in 2 mL DMF, and then stirred at room temperature for 16 hours. The reaction mixture was extracted with $H_2O$ and $CH_2Cl_2$. The organic layer was dried over $MgSO_4$, filtered and concentrated to afford a crude, which was purified by column chromatography (10% MeOH in $CH_2Cl_2$ as eluent) to obtain Compound 42 as light-yellow solid (131 mg, 80%).

$^1$H NMR (400 MHz, CDCl$_3$): δ 7.11-6.99 (m, 1H), 6.98-6.86 (m, 3H), 6.04 (s, 1H), 4.95 (t, J=7.3 Hz, 1H), 3.88 (s, 3H), 3.91-3.71 (m, 4H), 3.15-2.94 (m, 4H), 2.45 (t, J=7.3 Hz, 2H), 2.13-2.01 (m, 1H), 1.94-1.80 (m, 1H), 1.74-1.58 (m, 4H), 1.53-1.37 (m, 2H), 0.95 (t, J=7.3 Hz, 3H), 0.92 (t, J=7.3 Hz, 3H).

ESI-MS $C_{23}H_{32}N_4O_3S$: 444.2, found: 445.2 (M+H$^+$)$^+$, 467.2 (M+Na$^+$)$^+$.

Example 43: N-(1-benzylpiperidin-4-yl)-2-((6-oxo-4-propyl-1,6-dihydropyrimidin-2-yl)thio)acetamide (Compound 43)

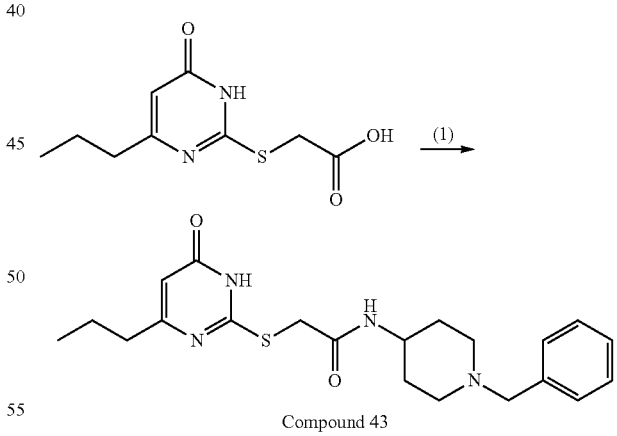

Compound 43

Reagents and conditions: 1-benzylpiperidin-4-amine, EDC, DMAP, DMF, r.t., 16 h, and yield 80%.

2-((6-Oxo-4-propyl-1,6-dihydropyrimidin-2-yl)thio)acetic acid (100 mg, 0.44 mmol), 1-benzylpiperidin-4-amine (92 mg, 0.48 mmol), EDC (101 mg, 0.53 mmol) and DMAP (11 mg, 0.09 mmol) were dissolved in 2 mL DMF, and then stirred at room temperature for 16 hours. The reaction mixture was extracted with $H_2O$ and $CH_2Cl_2$. The organic layer was dried over $MgSO_4$, filtered and concentrated to afford a crude, which was purified by column chromatography (10% MeOH in CH$_2$Cl$_2$ as eluent) to obtain Compound 43 as a white solid (141 mg, 80%).

$^1$H NMR (400 MHz, DMSO) δ 12.48 (s, 1H), 8.08 (d, J=7.6 Hz, 1H), 7.42-7.10 (m, 5H), 5.94 (s, 1H), 3.80 (s, 2H), 3.58-3.46 (m, 1H), 3.43 (s, 2H), 2.77-2.62 (m, 2H), 2.35 (t, J=7.4 Hz, 2H), 2.07-1.92 (m, 2H), 1.76-1.64 (m, 2H), 1.59 (sextet, J=7.4 Hz, 2H), 1.47-1.30 (m, 2H), 0.86 (t, J=7.4 Hz, 3H).

ESI-MS C$_{13}$H$_{15}$ClO$_3$: 400.2, found: 401.2 (M+H$^+$)$^+$, 423.1 (M+Na$^+$)$^+$.

Example 44: 2-((3-oxo-3-(4-phenylpiperazin-1-yl)propyl)thio)-6-propylpyrimidin-4(3H)-one (Compound 44)

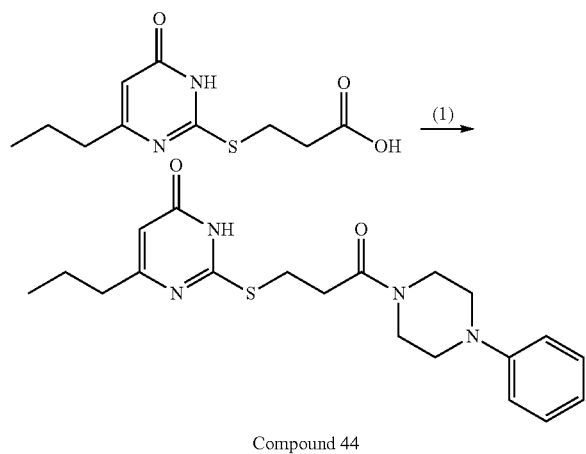

Compound 44

Reagents and conditions: (1) 1-phenylpiperazine, EDC, DMAP, DMF, r.t., 16 h, and yield 89%.

3-((6-Oxo-4-propyl-1,6-dihydropyrimidin-2-yl)thio)propanoic acid (100 mg, 0.41 mmol), 1-phenylpiperazine (70 mg, 0.45 mmol), EDC (96 mg, 0.5 mmol) and DMAP (10 mg, 0.08 mmol) were dissolved in 2 mL DMF, and then stirred at room temperature for 16 hours. The reaction mixture was extracted with H$_2$O and CH$_2$Cl$_2$. The organic layer was dried over MgSO$_4$, filtered and concentrated to afford a crude, which was purified by column chromatography (10% MeOH in CH$_2$Cl$_2$ as eluent) to obtain Compound 44 as a white solid (142 mg, 89%).

$^1$H NMR (400 MHz, CDCl$_3$): δ 9.73 (s, 1H), 7.34-7.23 (m, 2H), 7.06-6.86 (m, 3H), 5.77 (d, J=2.1 Hz, 1H), 4.68 (t, J=8.1 Hz, 2H), 3.87-3.61 (m, 4H), 3.29-3.09 (m, 4H), 2.86 (t, J=8.1 Hz, 2H), 2.36 (t, J=7.4 Hz, 2H), 1.75-1.57 (m, 2H), 1.01 (t, J=7.4 Hz, 3H).

ESI-MS C$_{20}$H$_{26}$N$_4$O$_2$S: 386.2, found: 387.2 (M+H$^+$)$^+$, 409.2 (M+Na$^+$)$^+$.

Example 45: 2-((3-(4-(2-methoxyphenyl)piperazin-1-yl)-2,2-dimethyl-3-oxopropyl)thio)-6-propylpyrimidin-4(3H)-one (Compound 45)

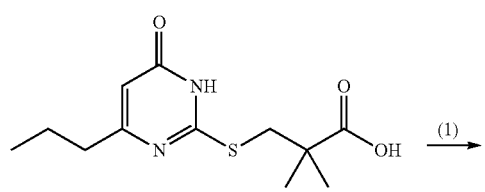

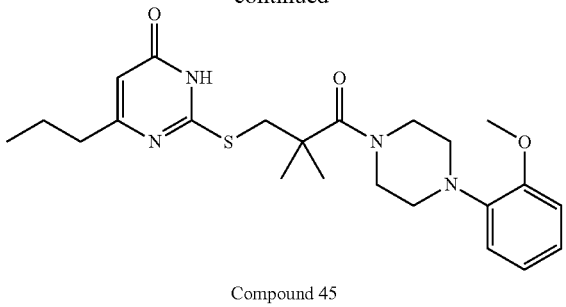

Compound 45

Reagents and conditions: 1-(2-methoxylphenyl)piperazine, EDC, DMAP, DMF, r.t., 16 h, and yield 53%.

2,2-Dimethyl-3-((6-oxo-4-propyl-1,6-dihydropyrimidin-2-yl)thio)propanoic acid (100 mg, 0.37 mmol), 1-(2-methoxyl-phenyl) piperazine (78 mg, 0.41 mmol), EDC (85 mg, 0.44 mmol) and DMAP (9 mg, 0.07 mmol) were dissolved in 2 mL DMF, and then stirred at room temperature for 16 hours. The reaction mixture was extracted with H$_2$O and CH$_2$Cl$_2$. The organic layer was dried over MgSO$_4$, filtered and concentrated to afford a crude, which was purified by column chromatography (10% MeOH in CH$_2$Cl$_2$ as eluent) to obtain Compound 45 as a white solid (87 mg, 53%).

$^1$H NMR (400 MHz, CDCl$_3$): δ 7.11-7.00 (m, 1H), 6.96-6.85 (m, 3H), 5.99 (d, J=0.8 Hz, 1H), 3.88 (s, 3H), 3.96-3.80 (m, 4H), 3.59 (s, 2H), 3.17-2.93 (m, 4H), 2.44 (t, J=7.4 Hz, 2H), 1.66 (sextet, J=7.4 Hz, 2H), 1.44 (s, 6H), 0.95 (t, J=7.4 Hz, 2H).

ESI-MS C$_{23}$H$_{32}$N$_4$O$_3$S: 444.2, found: 445.2 (M+H$^+$)$^+$, 467.2 (M+Na$^+$)$^+$.

Example 46: 2-((2-oxo-2-(4-(thiazol-2-yl)piperazin-1-yl)ethyl)thio)-6-propylpyrimidin-4(3H)-one (Compound 46)

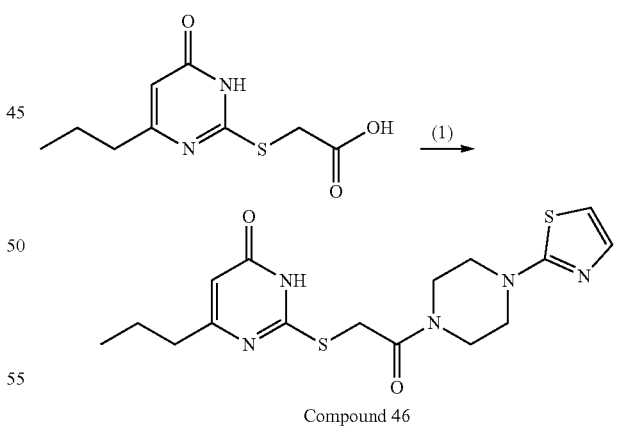

Compound 46

Reagents and conditions: 1-thiazol-2-yl-piperazine, EDC, DMAP, DMF, r.t., 16 h, and yield 86%.

2-((6-Oxo-4-propyl-1,6-dihydropyrimidin-2-yl)thio)acetic acid (100 mg, 0.44 mmol), 1-thiazol-2-yl-piperazine (82 mg, 0.48 mmol), EDC (101 mg, 0.53 mmol) and DMAP (11 mg, 0.09 mmol) were dissolved in 2 mL DMF, and then stirred at room temperature for 16 hours. The reaction mixture was extracted with H$_2$O and CH$_2$Cl$_2$. The organic layer was dried over MgSO$_4$, filtered and concentrated to afford a crude, which was purified by column chromatography (10% MeOH in $CH_2Cl_2$ as eluent) to obtain Compound 46 as a white solid (137 mg, 86%).

$^1$H NMR (400 MHz, $CDCl_3$): δ 7.22 (d, J=3.6 Hz, 1H), 6.64 (d, J=3.6 Hz, 1H), 6.04 (s, 1H), 4.14 (s, 2H), 3.84-3.79 (m, 2H), 3.77-3.71 (m, 2H), 3.67-3.62 (m, 2H), 3.53-3.46 (m, 2H), 2.44 (d, J=7.4 Hz, 2H), 1.65 (sextet, J=7.4 Hz, 2H), 0.93 (t, J=7.4 Hz, 3H).

ESI-MS $C_{16}H_{21}N_5O_2S_2$: 379.1, found: 380.1 $(M+H^+)^+$, 402.1 $(M+Na^+)^+$.

Example 47: 6-(3-chlorobenzyl)-5-methyl-2-((1-phenylpiperidin-4-yl)methyl)-[1,2,4]triazolo[1,5-a]pyrimidin-7(4H)-one (Compound 47)

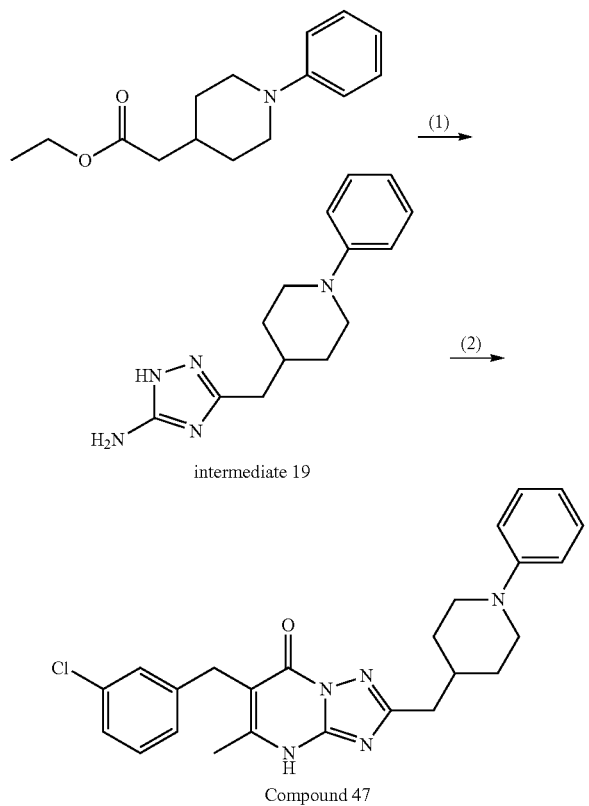

Reagents and conditions: (1) aminoguanidine bicarbonate, n-BuOH, 140° C., 16 h, and yield 31%; and (2) 2-(3-chloro-benzyl)-3-oxo-butyric acid ethyl ester, toluene, reflux by Dean-Stark, 16 h, and yield 38%.

Step 1

(1-Phenyl-piperidin-4-yl)-acetic acid ethyl ester (641 mg, 2.59 mmol) and aminoguanidine bicarbonate (705.5 mg, 5.18 mmol) were dissolved in 5 mL n-BuOH and then heated at 140° C. for 16 hours. After the solvent was removed, the reaction mixture was purified by column chromatography to give intermediate 19 as a white solid (210 mg, 31%).

$^1$H NMR (400 MHz, DMSO) δ 7.17 (t, J=7.3 Hz, 2H), 6.90 (d, J=7.3 Hz, 2H), 6.72 (t, J=7.3 Hz, 1H), 5.77 (s, 1H), 3.64 (d, J=12.1 Hz, 2H), 2.59 (dt, J=12.1, 2.4 Hz, 2H), 2.42-2.28 (m, 2H), 1.85-1.64 (m, 3H), 1.34-1.18 (m, 2H).

ESI-MS $C_{14}H_{19}N_5$: 257.2, found: 258.2 $(M+H^+)^+$, 280.2 $(M+Na^+)^+$.

Step 2

Intermediate 19 (150 mg, 0.58 mmol) and 2-(3-chlorobenzyl)-3-oxo-butyric acid ethyl ester (148.1 mg, 0.58 mmol) were dissolved in 5 mL toluene and then heated at reflux by Dean-Stark for 16 hours. After the solvent was removed, the reaction mixture was purified by column chromatography to afford Compound 47 as a pale-yellow solid (97.8 mg, 38%).

$^1$H NMR (400 MHz, DMSO) δ 7.34-7.12 (m, 6H), 6.91 (d, J=7.2 Hz, 2H), 6.73 (t, J=7.2 Hz, 1H), 3.85 (s, 2H), 3.66 (d, J=12.5 Hz, 2H), 2.70-2.55 (m, 4H), 2.31 (s, 3H), 1.98-1.85 (m, 1H), 1.81-1.72 (m, 2H), 1.44-1.27 (m, 2H).

ESI-MS $C_{25}H_{26}ClN_5O$: 447.2, found: 448.2 $(M+H^+)^+$.

Example 48: 6-isopropyl-2-((2-oxo-2-(4-(thiazol-2-yl)piperazin-1-yl)ethyl)thio)pyrimidin-4(3H)-one (Compound 48)

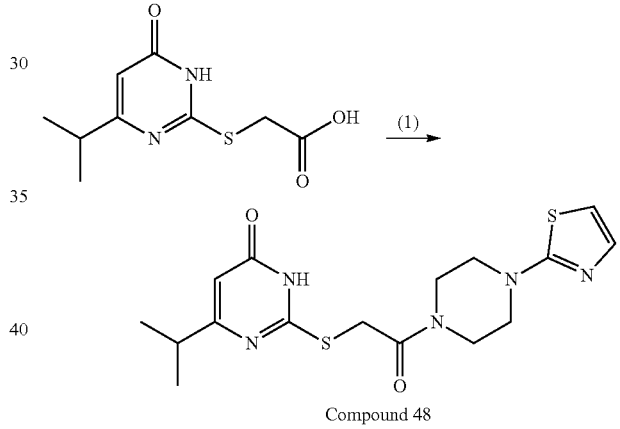

Reagents and conditions: 1-Thiazol-2-yl-piperazine, EDC, DMAP, DMF, r.t., 16 h, and yield 63%

(4-Isopropyl-6-oxo-1,6-dihydro-pyrimidin-2-ylsulfanyl)-acetic acid (100 mg, 0.44 mmol), 1-thiazol-2-yl-piperazine (81.6 mg, 0.48 mmol), EDC (100.8 mg, 0.53 mmol) and DMAP (16.1 mg, 0.13 mmol) were dissolved in 4 mL DMF, and then stirred at room temperature for 16 hours. After the solvent was removed, the reaction mixture was diluted with EtOAc, washed sequentially with water and brine. The organic layer was dried over $MgSO_4$, filtered and concentrated to afford a crude, which was purified by column chromatography with gradient elution (5% to 10% MeOH in $CH_2Cl_2$) to give Compound 48 as a yellow solid (104.1 mg, 63%).

$^1$H NMR (400 MHz, DMSO) δ 7.19 (d, J=3.6 Hz, 1H), 6.90 (d, J=3.6 Hz, 1H), 5.89 (s, 1H), 4.20 (s, 2H), 3.75-3.68 (m, 2H), 3.63-3.57 (m, 2H), 3.52-3.45 (m, 2H), 3.42-3.33 (m, 2H), 2.68-2.53 (m, 1H), 1.09 (d, J=6.8 Hz, 6H).

ESI-MS $C_{16}H_{21}N_5O_2S_2$: 379.1, found: 380.1 $(M+H^+)^+$, 402.1 $(M+Na^+)^+$.

Example 49: 6-(4-fluorobenzyl)-5-methyl-2-(1-((1S,4S)-5-phenyl-2,5-diazabicyclo[2.2.1]heptan-2-yl)ethyl)-[1,2,4]triazolo[1,5-a]pyrimidin-7(4H)-one (Compound 49)

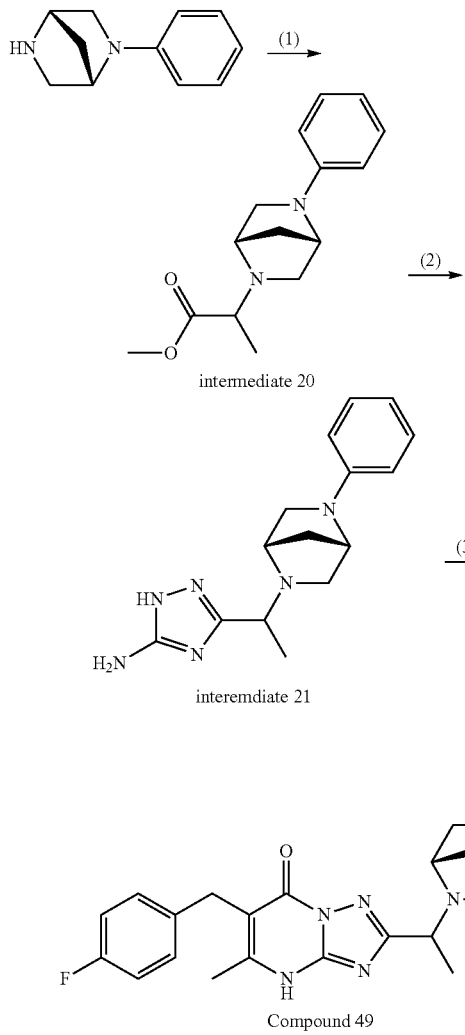

Reagents and conditions: (1) 2-bromo-propionic acid methyl ester, TEA, K$_2$CO$_3$, DMF, 60° C., 4 h, and yield 24%; (2) aminoguanidine bicarbonate, DMF, 140° C., 16 h, and yield 9%; and (3) 2-(4-fluoro-benzyl)-3-oxo-butyric acid ethyl ester, toluene, reflux by Dean-Stark, 16 h, and yield 2%.

Step 1

2-Phenyl-2,5-diaza-bicyclo[2.2.1]heptane (3 g, 1.71 mmol) and 2-bromo-propionic acid methyl ester (3.8 mL, 3.42 mmol), triethyl amine (4.8 mL, 3.42 mmol) and K$_2$CO$_3$ (4.7 g, 3.42 mmol) were dissolved in 10 mL DMF and heated at 60° C. for 4 hours. After the solvent was removed, the reaction mixture was diluted with EtOAc, washed sequentially with water and brine. The organic layer was dried over MgSO$_4$, filtered and concentrated to afford a crude, which was purified by column chromatography with gradient elution (1% to 5% EtOAc in hexane) to give intermediate 20 as a yellow oil (1.07 g, 24%).

$^1$H NMR (400 MHz, DMSO) δ 7.13 (t, J=7.7 Hz, 2H), 6.58 (t, J=7.7 Hz, 1H), 6.53 (d, J=7.7 Hz, 2H), 4.28-4.22 (m, 1H), 3.68-3.62 (m, 1H), 3.56 (s, 3H), 3.30 (dd, J=9.3, 2.2 Hz, 1H), 3.12 (q, J=6.8 Hz, 1H), 3.06 (d, J=9.3 Hz, 1H), 2.96 (dd, J=9.3, 2.2 Hz, 1H), 2.40 (d, J=9.3 Hz, 1H), 1.79 (s, 2H), 1.18 (d, J=6.8 Hz, 3H).

ESI-MS C$_{15}$H$_{20}$N$_2$O$_2$: 260.2, found: 261.2 (M+H$^+$)$^+$.

Step 2

Intermediate 20 (1.1 g, 0.41 mmol) and aminoguanidine bicarbonate (1.1 g, 0.82 mmol) were dissolved in 5 mL DMF and heated at 140° C. for 16 hours. After the solvent was removed, the reaction mixture was purified by column chromatography to give intermediate 21 as a white solid (104 mg, 9%).

ESI-MS C$_{15}$H$_{20}$N$_6$: 284.2, found: 285.2 (M+H$^+$)$^+$, 307.2 (M+Na$^+$)$^+$.

Step 3

Intermediate 21 (231 mg, 0.81 mmol) and 2-(4-fluorobenzyl)-3-oxo-butyric acid ethyl ester (232 mg, 0.97 mmol) were dissolved in 3 mL toluene and heated at reflux by Dean-Stark for 16 hours. After the solvent was removed, the reaction mixture was purified by column chromatography to afford Compound 49 as a pale-yellow solid (9 mg, 2%).

$^1$H NMR (300 MHz, DMSO) δ 7.32-7.21 (m, 2H), 7.19-6.99 (m, 4H), 6.65-6.50 (m, 3H), 4.35-4.20 (m, 1H), 3.94-3.70 (m, 1H), 3.82 (s, 2H), 3.13 (d, J=7.2 Hz, 1H), 2.79-2.57 (m, 1H), 2.36-2.25 (m, 1H), 2.29 (s, 3H), 1.84-1.52 (m, 2H), 1.35 (d, J=7.3 Hz, 3H), 1.27-1.20 (m, 1H).

ESI-MS C$_{26}$H$_{27}$FN$_6$O: 458.2, found: 459.2 (M+H$^+$)$^+$, 481.3 (M+Na$^+$)$^+$.

Example 50: 2-((2-((1S,4S)-5-(2-methoxyphenyl)-2,5-diazabicyclo[2.2.1]heptan-2-yl)-2-oxoethyl)thio)-6-propylpyrimidin-4(3H)-one (Compound 50)

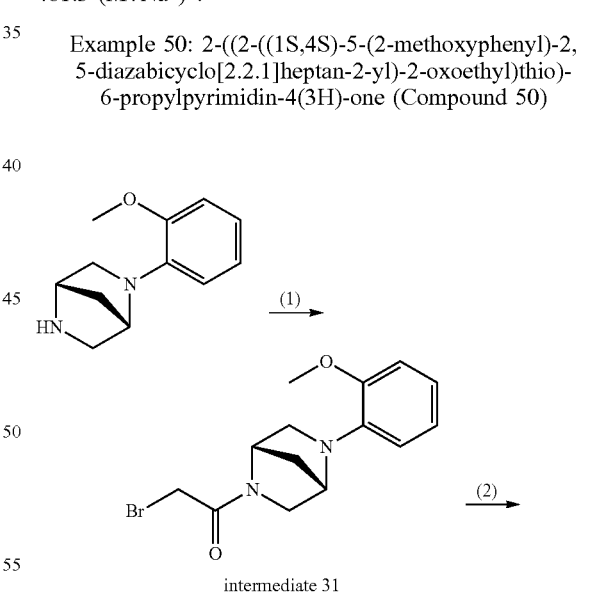

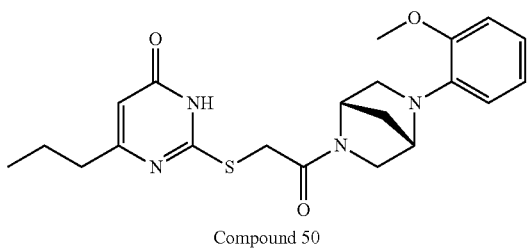

Reagents and conditions: (1) bromoacetic acid, EDC, DMAP, DMF, r.t., 16 h; and (2) 6-propyl-2-thiouracil, K₂CO₃, CH₂Cl₂/MeOH (1:1), 80° C., 4 h, 40% over 2 steps.

Step 1

(1S,4S)-2-(2-Methoxyphenyl)-2,5-diazabicyclo[2.2.1]heptane (100 mg, 0.49 mmol), bromoacetic acid (75 mg, 0.54 mmol), EDC (113 mg, 0.59 mmol) and DMAP (12 mg, 0.11 mmol) were dissolved in 2 mL DMF, and then stirred at room temperature for 16 hours. The reaction mixture was extracted with H₂O and CH₂Cl₂. The organic layer was dried over MgSO₄, filtered and concentrated to afford intermediate 31 for direct use in the next step.

ESI-MS C₁₄H₁₇BrN₂O₂: 324.1, found: 325.3 (M+H⁺)⁺, 347.2 (M+Na⁺)⁺.

Step 2

Intermediate 31, 6-propyl-2-thiouracil (45 mg, 0.26 mmol) and K₂CO₃ (50 mg, 0.36 mmol) were dissolved in 2 mL (CH₂Cl₂: MeOH/1:1), and then stirred at 80° C. for 4 h. After the starting materials were consumed, the K₂CO₃ was filtered through filter paper, filtrate was collected and concentrated. The crude was purified by column chromatography (10% MeOH in CH₂Cl₂ as eluent) to obtain Compound 50 as a white solid (82 mg, 40% over 2 steps).

¹H NMR (400 MHz, DMSO) δ 6.89 (dd, J=7.9, 1.5 Hz, 1H), 6.82-6.76 (m, 1H), 6.72 (dd, J=7.9, 1.5 Hz, 1H), 6.69-6.63 (m, 1H), 5.89 (s, 0.5H), 4.76 (s, 0.5H), 4.69 (s, 0.5H), 4.60 (s, 0.5H), 4.43 (s, 0.5H), 4.18-4.01 (m, 1H), 3.77 (dd, J=9.8, 2.1 Hz, 0.5H), 3.72 (s, 2H), 3.71 (s, 3H), 3.67 (dd, J=9.8, 2.1 Hz, 0.5H), 3.48 (d, J=11.2 Hz, 0.5H), 3.32 (d, J=11.2 Hz, 2H), 3.15 (d, J=9.6 Hz, 0.5H), 3.00 (d, J=9.6 Hz, 0.5H), 1.97 (d, J=9.6 Hz, 0.5H), 1.87 (d, J=9.6 Hz, 1H), 1.76 (d, J=9.6 Hz, 0.5H), 1.55-1.40 (m, 2H), 0.86 (t, J=7.3 Hz, 2H), 0.77 (t, J=7.3 Hz, 3H).

ESI-MS C₂₁H₂₆N₄O₃S: 414.2, found: 415.2 (M+H⁺)⁺, 437.1 (M+Na⁺)⁺.

Example 51: (R)-6-isopropyl-2-((2-(4-(2-methoxyphenyl)-2-methylpiperazin-1-yl)-2-oxoethyl)thio)pyrimidin-4(3H)-one (Compound 51)

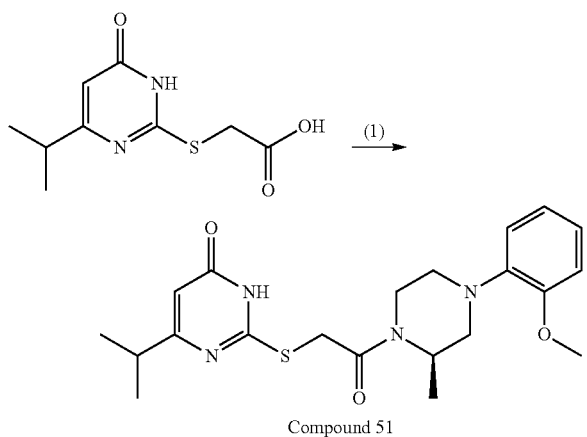

Compound 51

Reagents and conditions: 1-(2-methoxy-phenyl)-3-methyl-piperazine, EDCI, DMAP, DMF, r.t., 16 h, and yield 62%.

(4-Isopropyl-6-oxo-1,6-dihydro-pyrimidin-2-ylsulfanyl)-acetic acid (100 mg, 0.44 mmol), 1-(2-methoxy-phenyl)-3-methyl-piperazine (108.5 mg, 0.53 mmol), EDCI (100.8 mg, 0.53 mmol) and DMAP (16.1 mg, 0.13 mmol) were dissolved in 4 mL DMF, and then stirred at room temperature for 16 hours. After the solvent was removed, the reaction mixture was diluted with EtOAc, washed sequentially with water and brine. The organic layer was dried over MgSO₄, filtered and concentrated to afford a crude, which was purified by column chromatography (gradient elution: 5% to 10% MeOH in CH₂Cl₂) to give Compound 51 as a yellow solid (112.2 mg, 62%).

¹H NMR (400 MHz, CDCl₃) δ 7.06-6.99 (m, 1H), 6.93 (td, J=7.5, 1.5 Hz, 1H), 6.90-6.84 (m, 2H), 6.06 (s, 1H), 4.86-4.76 (m, 0.5H), 4.52 (d, J=13.4 Hz, 0.5H), 4.23-4.15 (m, 0.5H), 4.13 (s, 2H), 3.86 (s, 3H), 3.82-3.65 (m, 1H), 3.49-3.16 (m, 2.5H), 2.85-2.63 (m, 3H), 1.59 (d, J=6.8 Hz, 1.5H), 1.42 (d, J=6.8 Hz, 1.5H), 1.20 (d, J=6.9 Hz, 6H).

ESI-MS C₂₁H₂₈N₄O₃S: 416.2, found: 417.2 (M+H⁺)⁺, 439.2 (M+Na⁺)⁺.

Example 52: (S)-6-isopropyl-2-((2-(4-(2-methoxyphenyl)-2-methylpiperazin-1-yl)-2-oxoethyl)thio)pyrimidin-4(3H)-one (Compound 52)

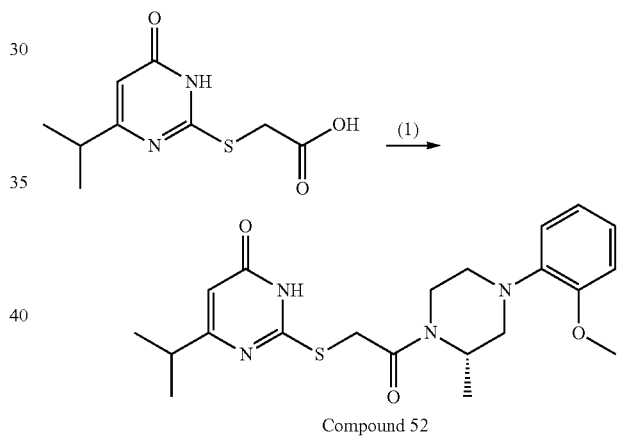

Compound 52

Reagents and conditions: 1-(2-methoxy-phenyl)-3-methyl-piperazine, EDCI, DMAP, DMF, r.t., 16 h, and yield 80%.

(4-Isopropyl-6-oxo-1,6-dihydro-pyrimidin-2-ylsulfanyl)-acetic acid (100 mg, 0.44 mmol), 1-(2-methoxy-phenyl)-3-methyl-piperazine (108.5 mg, 0.53 mmol), EDCI (100.8 mg, 0.53 mmol) and DMAP (16.1 mg, 0.13 mmol) were dissolved in 4 mL DMF, and then stirred at room temperature for 16 hours. After the solvent was removed, the reaction mixture was diluted with EtOAc, washed sequentially with water and brine. The organic layer was dried over MgSO₄, filtered and concentrated to afford a crude, which was purified by column chromatography (gradient elution: 5% to 10% MeOH in CH₂Cl₂) to give Compound 52 as a yellow solid (145.1 mg, 80%).

¹H NMR (400 MHz, CDCl₃): δ 7.08-6.98 (m, 1H), 6.96-6.84 (m, 3H), 6.06 (s, 1H), 4.88-4.76 (m, 0.5H), 4.52 (s, 0.5H), 4.22-4.06 (m, 0.5H), 4.13 (s, 2H), 3.87 (s, 3H), 3.82-3.66 (m, 1H), 3.51-3.16 (m, 2.5H), 2.86-2.62 (m, 3H), 1.59 (d, J=6.8 Hz, 1.5H), 1.42 (d, J=6.8 Hz, 1.5H), 1.20 (d, J=6.9 Hz, 6H).

ESI-MS $C_{21}H_{26}N_4O_3S$: 416.2, found: 417.2 $(M+H^+)^+$, 439.1 $(M+Na^+)^+$.

Example 53: (R)-6-isopropyl-2-((2-(4-(2-methoxyphenyl)-3-methylpiperazin-1-yl)-2-oxoethyl)thio)pyrimidin-4(3H)-one (Compound 53)

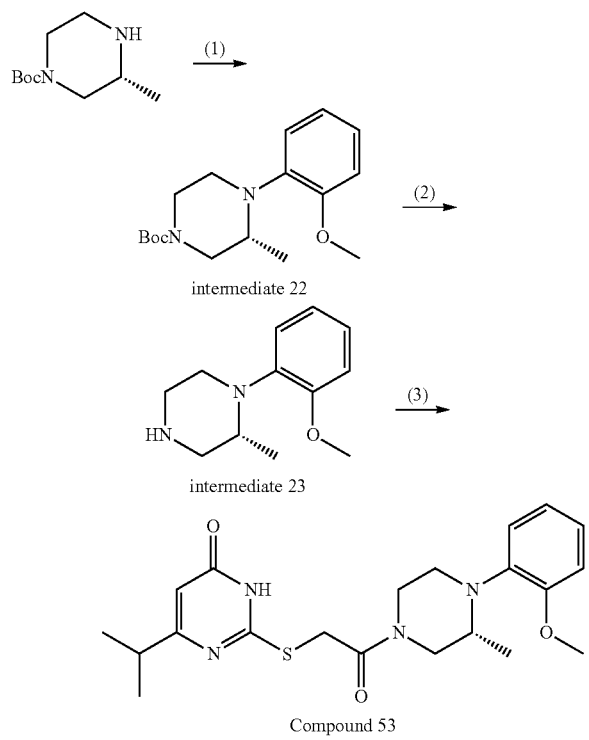

Reagents and conditions: (1) 1-bromo-2-methoxy-benzene, $Pd_2(dba)_3$, BINAP, t-BuOK, toluene, 105° C., 16 h, and yield 21%; (2) TFA, $CH_2Cl_2$, 0° C.; r.t., 2.5 h, and yield 99%; and (3) (4-isopropyl-6-oxo-1,6-dihydro-pyrimidin-2-ylsulfanyl)-acetic acid, EDCI, DMAP, DMF, r.t., 16 h, and yield 60%.

Step 1

Tris(dibenzylideneacetone)dipalladium (0.46 g, 0.05 mmol) and (+/−)-2,2'-bis(diphenylphosphino)-1,1'-binaphthyl (0.62 g, 0.10 mmol) were dissolved in 10 mL toluene, and then stirred at 50° C. for 10 minutes. (R)-4-N-Boc-2-methylpiperazine (1 g, 0.5 mmol), 1-bromo-2-methoxy-benzene (0.7 mL, 0.55 mmol) and t-BuOK (1.1 g, 1 mmol) were added, and then stirred at 105° C. for 16 hours. The solvent was removed to obtain the crude, which was purified by column chromatography (gradient elution: 1% to 5% EtOAc in hexane) to give intermediate 22 as a colorless liquid (317 mg, 21%).

$^1$H NMR (400 MHz, DMSO) δ 7.07-6.81 (m, 4H), 3.76 (s, 3H), 3.56-3.44 (m, 3H), 3.42-2.98 (m, 3H), 2.72-2.63 (m, 1H), 1.41 (s, 9H), 0.76 (d, J=6.2 Hz, 3H).

ESI-MS $C_{17}H_{26}N_2O_3$: 306.2, found: 307.2 $(M+H^+)^+$, 329.2 $(M+Na^+)^+$.

Step 2

Intermediate 22 (317 mg, 1.03 mmol) was dissolved in 25 mL dicholoromethane at 0° C., and trifluoroacetic acid (4 mL, 51.7 mmol) was added slowly, and the reaction was stirred for 2.5 hours at room temperature. The reaction mixture was neutralized by 6N $NaOH_{(aq)}$ and extracted by dicholoromethane. The organic layers were collected, dried over $MgSO_4$, filtered and concentrated to afford intermediate 23 as a yellow oil (217 mg, 99%).

ESI-MS $C_{12}H_{18}N_2O$: 206.1, found: 207.2 $(M+H^+)^+$.

Step 3

(4-Isopropyl-6-oxo-1,6-dihydro-pyrimidin-2-ylsulfanyl)-acetic acid (100 mg, 0.44 mmol), 1-(2-methoxy-phenyl)-2-methyl-piperazine (108.5 mg, 0.53 mmol), EDCI (100.8 mg, 0.53 mmol) and DMAP (16.1 mg, 0.13 mmol) were dissolved in 4 mL DMF, and then stirred at room temperature for 16 hours. After the solvent was removed, the reaction mixture was diluted with EtOAc, washed sequentially with water and brine. The organic layer was dried over $MgSO_4$, filtered and concentrated to afford a crude, which was purified by column chromatography (gradient elution: 5% to 10% MeOH in $CH_2Cl_2$) to give Compound 53 as a pale-yellow solid (108 mg, 60%).

$^1$H NMR (300 MHz, DMSO) δ 7.10-6.80 (m, 4H), 5.90 (s, 1H), 4.28-4.08 (m, 2H), 3.77 (s, 3H), 3.83-3.02 (m, 7H), 2.69-2.57 (m, 1H), 1.12 (d, J=6.8 Hz, 6H), 0.83 (d, J=6.2 Hz, 1.5H), 0.77 (d, J=6.3 Hz, 1.5H).

ESI-MS $C_{21}H_{28}N_4O_3S$: 416.2, found: 417.2 $(M+H^+)^+$, 439.2 $(M+Na^+)^+$.

Example 54: 6-(4-fluorobenzyl)-5-methyl-2-(1-((R)-3-methyl-4-phenylpiperazin-1-yl)ethyl)-[1,2,4]triazolo[1,5-a]pyrimidin-7(4H)-one (Compound 54)

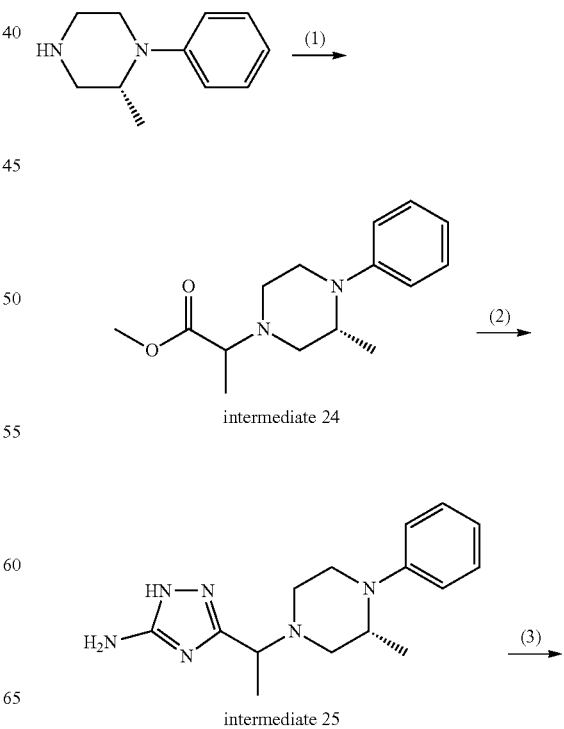

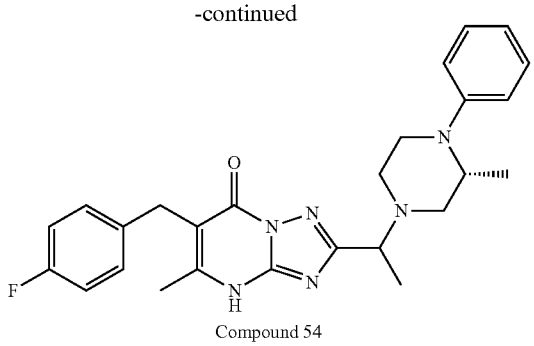

Compound 54

Reagents and conditions: (1) 2-bromo-propionic acid methyl ester, Et$_3$N, K$_2$CO$_3$, DMF, 60° C., 4 h, and yield 83%; (2) aminoguanidine bicarbonate, DMF, reflux, 16 h, and yield 15%; and (3) 2-(4-fluoro-benzyl)-3-oxo-butyric acid ethyl ester, toluene, reflux by Dean-Stark, 16 h, and yield 39%.

Step 1

1-(2-Methoxy-phenyl)-2-methyl-piperazine (3.1 g, 1.74 mmol), 2-bromo-propionic acid methyl ester (3.9 mL, 3.48 mmol), triethyl amine (4.8 mL, 3.42 mmol) and K$_2$CO$_3$ (9.6 g, 6.9 mmol) were dissolved in 10 mL DMF and heated at 60° C. for 4 hours. After the solvent was removed, the reaction mixture was diluted with EtOAc, washed sequentially with water and brine. The organic layer was dried over MgSO$_4$, filtered and concentrated to afford a crude, which was purified by column chromatography (gradient elution: 1% to 5% EtOAc in hexane) to give intermediate 24 as a yellow oil (3.76 g, 83%).

$^1$H NMR (400 MHz, DMSO) δ 7.20 (t, J=7.2 Hz, 2H), 6.87 (d, J=7.2 Hz, 2H), 6.73 (t, J=7.2 Hz, 1H), 3.99-3.87 (m, 1H), 3.64 (s, 3H), 3.45-3.34 (m, 1H), 3.27-3.16 (m, 1H), 2.99-2.79 (m, 2H), 2.72-2.60 (m, 1.5H), 2.57-2.47 (m, 1H), 2.44-2.29 (m, 0.5H), 1.22 (d, J=3.9 Hz, 1.5H), 1.20 (d, J=3.9 Hz, 1.5H), 0.98 (d, J=6.0 Hz, 1.5H), 0.95 (d, J=6.0 Hz, 1.5H).
ESI-MS C$_{15}$H$_{22}$N$_2$O$_2$: 262.2, found: 263.2 (M+H$^+$)$^+$.

Step 2

Intermediate 24 (2 g, 0.76 mmol) and aminoguanidine bicarbonate (2.1 g, 1.52 mmol) were dissolved in 5 mL DMF and heated at reflux for 16 hours. After the solvent was removed, the reaction mixture was purified by column chromatography to give intermediate 25 as a white solid (290 mg, 15%).

$^1$H NMR (400 MHz, DMSO) δ 7.15 (t, J=7.5 Hz, 2H), 6.84 (d, J=7.5 Hz, 2H), 6.71 (t, J=7.5 Hz, 1H), 5.77 (s, 1H), 4.09 (q, J=5.3 Hz, 1H), 3.95-3.82 (m, 1H), 3.24-3.15 (m, 2H), 3.17 (d, J=4.7 Hz, 2H), 2.98-2.71 (m, 2.5H), 2.69-2.55 (m, 1H), 2.42-2.30 (m, 1H), 2.26-2.13 (m, 0.5H), 1.31 (d, J=6.6 Hz, 1.5H), 1.29 (d, J=6.6 Hz, 1.5H), 0.96 (d, J=5.3 Hz, 1.5H), 0.94 (d, J=5.3 Hz, 1.5H).
ESI-MS C$_{15}$H$_{22}$N$_6$: 286.2, found: 287.2 (M+H$^+$)$^+$, 309.2 (M+Na$^+$)$^+$.

Step 3

Intermediate 25 (150 mg, 0.55 mmol) and 2-(4-fluoro-benzyl)-3-oxo-butyric acid ethyl ester (157.5 mg, 0.66 mmol) were dissolved in 3 mL toluene and heated at reflux by Dean-Stark for 16 hours. After the solvent was removed, the reaction mixture was purified by column chromatography to afford Compound 54 as a pale-yellow solid (98.9 mg, 39%).

$^1$H NMR (400 MHz, DMSO) δ 7.26 (t, J=8.9 Hz, 2H), 7.17 (t, J=8.1 Hz, 2H), 7.06 (t, J=8.9 Hz, 2H), 6.84 (d, J=8.1 Hz, 2H), 6.72 (t, J=8.1 Hz, 1H), 3.96-3.84 (m, 2H), 3.82 (s, 2H), 3.24-3.15 (m, 1H), 3.00-2.79 (m, 2H), 2.76-2.55 (m, 2H), 2.45-2.35 (m, 1H), 2.30 (s, 3H), 1.45 (d, J=6.8 Hz, 1.5H), 1.42 (d, J=6.8 Hz, 1.5H), 0.97 (d, J=6.7 Hz, 1.5H), 0.96 (d, J=6.7 Hz, 1.5H).
ESI-MS C$_{26}$H$_{29}$FN$_6$O: 460.2, found: 461.3 (M+H$^+$)$^+$.

Example 55: 2-((2-oxo-2-(4-(5-(trifluoromethyl)pyridin-2-yl)piperazin-1-yl)ethyl)thio)-6-propylpyrimidin-4(3H)-one (Compound 55)

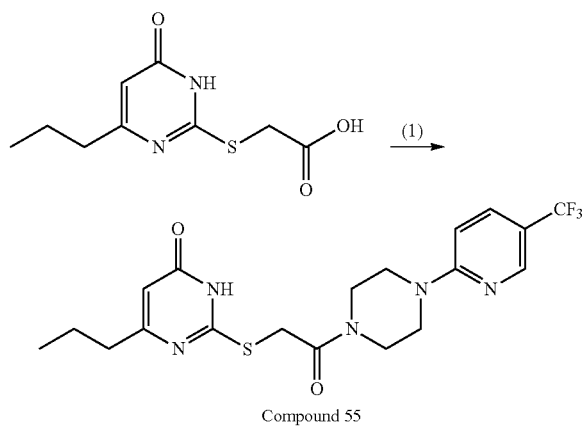

Compound 55

Reagents and conditions: 1-[5-(trifloromethyl)pyrid-2-yl]piperazine, EDC, DMAP, DMF, r.t., 16 h, and yield 90%.

2-((6-Oxo-4-propyl-1,6-dihydropyrimidin-2-yl)thio)acetic acid (100 mg, 0.44 mmol), 1-[5-(trifloromethyl)pyrid-2-yl]piperazine (111 mg, 0.48 mmol), EDC (101 mg, 0.53 mmol) and DMAP (11 mg, 0.09 mmol) were dissolved in 2 mL DMF, and then stirred at room temperature for 16 hours. The reaction mixture was extracted with H$_2$O and CH$_2$Cl$_2$. The organic layer was dried over MgSO$_4$, filtered and concentrated to afford a crude, which was purified by column chromatography (10% MeOH in CH$_2$Cl$_2$ as eluent) to obtain Compound 55 as a white solid (175 mg, 90%).

$^1$H NMR (400 MHz, CDCl$_3$): δ 8.42 (d, J=2.5 Hz, 1H), 7.69 (dd, J=9.0, 2.5 Hz, 1H), 6.67 (d, J=9.0 Hz, 1H), 6.04 (s, 1H), 4.15 (s, 2H), 3.88-3.60 (m, 8H), 2.44 (t, J=7.4 Hz, 2H), 1.65 (sextet, J=7.4 Hz, 2H), 0.93 (t, J=7.4 Hz, 3H).
ESI-MS C$_{19}$H$_{22}$F$_3$N$_5$O$_2$S: 441.1, found: 442.1 (M+H$^+$)$^+$, 464.1 (M+Na$^+$)$^+$.

Example 56: 2-((2-oxo-2-(4-(pyridin-2-ylmethyl)piperazin-1-yl)ethyl)thio)-6-propylpyrimidin-4(3H)-one (Compound 56)

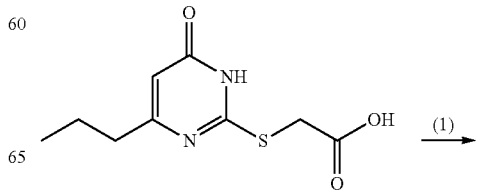

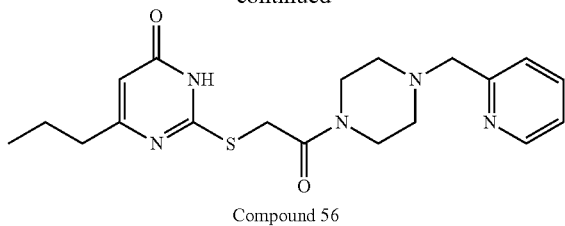

Compound 56

Reagents and conditions: 1-(2-pyridylmethyl)piperazine, EDC, DMAP, DMF, r.t., 16 h, and yield 85%.

2-((6-Oxo-4-propyl-1,6-dihydropyrimidin-2-yl)thio)acetic acid (100 mg, 0.44 mmol), 1-(2-pyridylmethyl)piperazine (0.08 ml, 0.48 mmol), EDC (101 mg, 0.53 mmol) and DMAP (11 mg, 0.09 mmol) were dissolved in 2 mL DMF, and then stirred at room temperature for 16 hours. The reaction mixture was extracted with $H_2O$ and $CH_2Cl_2$. The organic layer was dried over $MgSO_4$, filtered and concentrated to afford a crude, which was purified by column chromatography (10% MeOH in $CH_2Cl_2$ as eluent) to obtain Compound 56 as a brown solid (144 mg, 85%).

$^1$H NMR (400 MHz, CDCl$_3$): δ 8.58 (d, J=7.7 Hz, 1H), 7.67 (t, J=7.7 Hz, 1H), 7.39 (d, J=7.7 Hz, 1H), 7.19 (t, J=7.7 Hz, 1H), 6.01 (s, 1H), 4.08 (s, 2H), 3.71 (s, 2H), 3.74-3.54 (m, 4H), 2.62-2.49 (m, 4H), 2.42 (t, J=7.4 Hz, 2H), 1.64 (sextet, J=7.4 Hz, 2H), 0.93 (t, J=7.3 Hz, 3H).

ESI-MS $C_{19}H_{25}N_5O_2S$: 387.2, found: 388.2 (M+H$^+$)$^+$, 410.1 (M+Na$^+$)$^+$.

Example 57: 2-((2-(4-(benzo[d][1,3]dioxol-5-ylmethyl)piperazin-1-yl)-2-oxoethyl)thio)-6-propylpyrimidin-4(3H)-one (Compound 57)

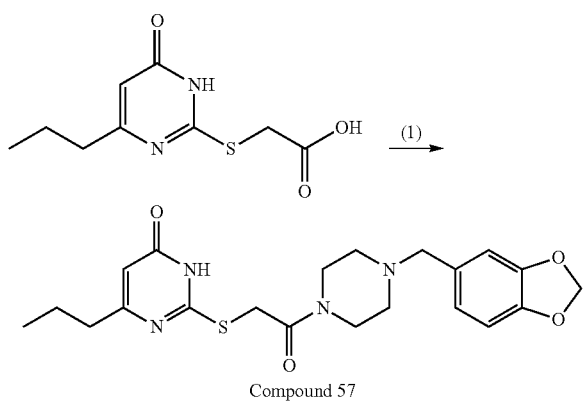

Compound 57

Reagents and conditions: (1) 1-piperonylpiperazine, EDC, DMAP, DMF, r.t., 16 h, and yield 84%.

2-((6-Oxo-4-propyl-1,6-dihydropyrimidin-2-yl)thio)acetic acid (100 mg, 0.44 mmol), 1-piperonylpiperazine (106 mg, 0.48 mmol), EDC (101 mg, 0.53 mmol) and DMAP (11 mg, 0.09 mmol) were dissolved in 2 mL DMF, and then stirred at room temperature for 16 hours. The reaction mixture was extracted with $H_2O$ and $CH_2Cl_2$. The organic layer was dried over $MgSO_4$, filtered and concentrated to afford a crude, which was purified by column chromatography (10% MeOH in $CH_2Cl_2$ as eluent) to obtain Compound 57 as a white solid (158 mg, 84%).

$^1$H NMR (400 MHz, CDCl$_3$): δ 6.85 (s, 1H), 6.78-6.69 (m, 2H), 6.02 (s, 1H), 5.95 (s, 2H), 4.06 (s, 2H), 3.71-3.50 (m, 4H), 3.45 (s, 2H), 2.47 (t, J=7.4 Hz, 2H), 2.45-2.40 (m, 4H), 1.64 (sextet, J=7.4 Hz, 2H), 0.94 (t, J=7.4 Hz, 3H).

ESI-MS $C_{21}H_{26}N_4O_4S$: 430.2, found: 431.1 (M+H$^+$)$^+$, 453.1 (M+Na$^+$)$^+$.

Example 58: 2-((2-(4-((4,6-dimethoxypyrimidin-2-yl)methyl)piperazin-1-yl)-2-oxoethyl)thio)-6-propyl pyrimidin-4(3H)-one (Compound 58)

Compound 58

Reagents and conditions: 1-[(4,6-dimethoxyprimidin-2-yl)methyl]piperazine, EDC, DMAP, DMF, r.t., 16 h, and yield 24%.

2-((6-Oxo-4-propyl-1,6-dihydropyrimidin-2-yl)thio)acetic acid (100 mg, 0.44 mmol), 1-[(4,6-dimethoxyprimidin-2-yl)methyl]piperazine (115 mg, 0.48 mmol), EDC (101 mg, 0.53 mmol) and DMAP (11 mg, 0.09 mmol) were dissolved in 2 mL DMF, and then stirred at room temperature for 16 hours. The reaction mixture was extracted with $H_2O$ and $CH_2Cl_2$. The organic layer was dried over $MgSO_4$, filtered and concentrated to afford a crude, which was purified by column chromatography (10% MeOH in $CH_2Cl_2$ as eluent) to obtain Compound 58 as light yellow solid (48 mg, 24%).

$^1$H NMR (400 MHz, CDCl$_3$): δ 6.02 (s, 1H), 5.92 (s, 1H), 4.07 (s, 2H), 3.92 (s, 6H), 3.74 (s, 2H), 3.81-3.61 (m, 4H), 2.84-2.68 (m, 4H), 2.43 (t, J=7.4 Hz, 2H), 1.64 (sextet, J=7.4 Hz, 2H), 0.93 (t, J=7.4 Hz, 3H).

ESI-MS $C_{20}H_{28}N_6O_4S$: 448.2, found: 449.2 (M+H$^+$)$^+$, 471.1 (M+Na$^+$)$^+$.

Example 59: 2-((2-(4-(2-methoxyethyl)piperazin-1-yl)-2-oxoethyl)thio)-6-propylpyrimidin-4(3H)-one (Compound 59)

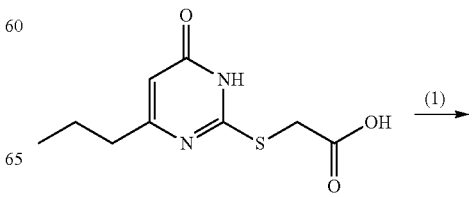

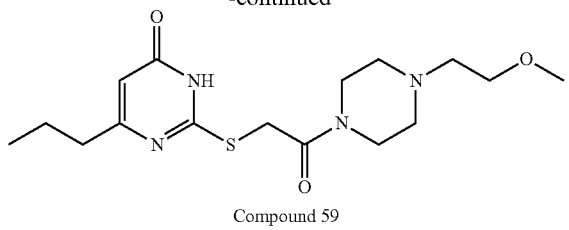

Compound 59

Reagents and conditions: 1-(2-methoxyethyl)piperazine, EDC, DMAP, DMF, r.t., 16 h, and yield 87%.

2-((6-Oxo-4-propyl-1,6-dihydropyrimidin-2-yl)thio)acetic acid (100 mg, 0.44 mmol), 1-(2-methoxyethyl)piperazine (0.07 ml, 0.48 mmol), EDC (101 mg, 0.53 mmol) and DMAP (11 mg, 0.09 mmol) were dissolved in 2 mL DMF, and then stirred at room temperature for 16 hours. The reaction mixture was extracted with $H_2O$ and $CH_2Cl_2$. The organic layer was dried over $MgSO_4$, filtered and concentrated to afford a crude, which was purified by column chromatography (10% MeOH in $CH_2Cl_2$ as eluent) to obtain Compound 59 as a light-yellow solid (135 mg, 87%).

$^1$H NMR (400 MHz, CDCl$_3$): δ 6.02 (s, 1H), 4.06 (s, 2H), 3.75-3.57 (m, 4H), 3.53 (t, J=6.8 Hz, 2H), 3.35 (s, 3H), 2.63 (t, J=6.8 Hz, 2H), 2.66-2.48 (m, 4H), 2.43 (t, J=7.4 Hz, 2H), 1.65 (h, J=7.4 Hz, 2H), 0.94 (t, J=7.4 Hz, 3H).

ESI-MS $C_{16}H_{26}N_4O_3S$: 354.2, found: 355.1 (M+H$^+$)$^+$, 377.1 (M+Na$^+$)$^+$.

Example 60: 2-((2-oxo-2-(4-phenethylpiperazin-1-yl)ethyl)thio)-6-propylpyrimidin-4(3H)-one (Compound 60)

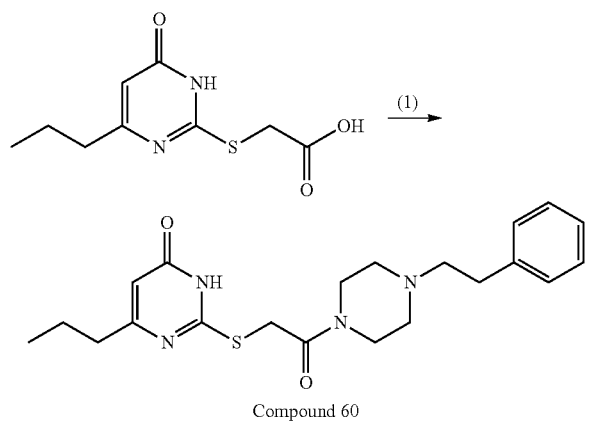

Compound 60

Reagents and conditions: 1-(2-phenylethyl)piperazine, EDC, DMAP, DMF, r.t., 16 h, and yield 90%.

2-((6-Oxo-4-propyl-1,6-dihydropyrimidin-2-yl)thio)acetic acid (100 mg, 0.44 mmol), 1-(2-methoxyethyl)piperazine (0.09 ml, 0.48 mmol), EDC (101 mg, 0.53 mmol) and DMAP (11 mg, 0.09 mmol) were dissolved in 2 mL DMF, and then stirred at room temperature for 16 hours. The reaction mixture was extracted with $H_2O$ and $CH_2Cl_2$. The organic layer was dried over $MgSO_4$, filtered and concentrated to afford a crude, which was purified by column chromatography (10% MeOH in $CH_2Cl_2$ as eluent) to obtain Compound 60 as a white solid (158 mg, 90%).

$^1$H NMR (400 MHz, CDCl$_3$): δ 7.29 (t, J=7.7 Hz, 2H), 7.23 (t, J=7.7 Hz, 1H), 7.20 (d, J=7.7 Hz, 2H), 6.03 (s, 1H), 4.08 (s, 2H), 3.81-3.48 (m, 4H), 2.91-2.48 (m, 8H), 2.43 (t, J=7.4 Hz, 2H), 1.65 (sextet, J=7.4 Hz, 2H), 0.94 (t, J=7.4 Hz, 3H).

ESI-MS $C_{21}H_{28}N_4O_2S$: 400.2, found: 401.2 (M+H$^+$)$^+$, 423.1 (M+Na$^+$)$^+$.

Example 61: 2-((2-(4-cyclohexylpiperazin-1-yl)-2-oxoethyl)thio)-6-propylpyrimidin-4(3H)-one (Compound 61)

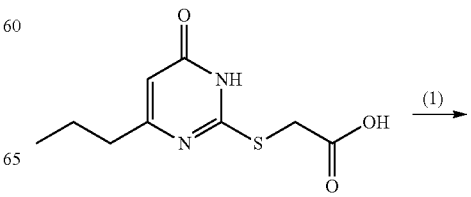

Compound 61

Reagents and conditions: 1-cyclohexylpiperazine, EDC, DMAP, DMF, r.t., 16 h, and yield 75%.

2-((6-Oxo-4-propyl-1,6-dihydropyrimidin-2-yl)thio)acetic acid (100 mg, 0.44 mmol), 1-cyclohexylpiperazine (81 mg, 0.48 mmol), EDC (101 mg, 0.53 mmol) and DMAP (11 mg, 0.09 mmol) were dissolved in 2 mL DMF, and then stirred at room temperature for 16 hours. The reaction mixture was extracted with $H_2O$ and $CH_2Cl_2$. The organic layer was dried over $MgSO_4$, filtered and concentrated to afford a crude, which was purified by column chromatography (10% MeOH in $CH_2Cl_2$ as eluent) to obtain Compound 61 as a yellow solid (124 mg, 75%).

$^1$H NMR (400 MHz, CDCl$_3$): δ 6.02 (s, 1H), 4.06 (s, 2H), 3.72-3.52 (m, 4H), 2.69-2.49 (m, 4H), 2.43 (t, J=7.4 Hz, 2H), 2.38-2.25 (m, 1H), 1.91-1.72 (m, 4H), 1.72-1.55 (m, 3H), 1.34-1.01 (m, 5H), 0.94 (t, J=7.4 Hz, 3H).

ESI-MS $C_{19}H_{30}N_4O_2S$: 378.2, found: 379.2 (M+H$^+$)$^+$, 401.2 (M+Na$^+$)$^+$.

Example 62: 2-((2-oxo-2-(4-(pyridin-4-yl)piperazin-1-yl)ethyl)thio)-6-propylpyrimidin-4(3H)-one (Compound 62)

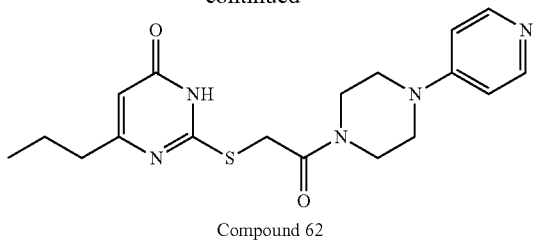

Compound 62

Reagents and conditions: 1-(4-pyridyl)piperazine, EDC, DMAP, DMF, r.t., 16 h, and yield 21%.

2-((6-Oxo-4-propyl-1,6-dihydropyrimidin-2-yl)thio)acetic acid (100 mg, 0.44 mmol), 1-(4-pyridyl)piperazine (79 mg, 0.48 mmol), EDC (101 mg, 0.53 mmol) and DMAP (11 mg, 0.09 mmol) were dissolved in 2 mL DMF, and then stirred at room temperature for 16 hours. The reaction mixture was extracted with $H_2O$ and $CH_2Cl_2$. The organic layer was dried over $MgSO_4$, filtered and concentrated to afford a crude, which was purified by column chromatography (16% MeOH in $CH_2Cl_2$ as eluent) to obtain Compound 62 as a white solid (35 mg, 21%).

$^1$H NMR (400 MHz, DMSO) δ 8.18 (d, J=6.5 Hz, 2H), 6.84 (d, J=6.5 Hz, 2H), 5.93 (s, 1H), 4.20 (s, 2H), 3.70 (t, J=5.3 Hz, 2H), 3.59 (t, J=5.3 Hz, 2H), 3.44 (t, J=5.3 Hz, 2H), 3.34 (t, J=5.3 Hz, 2H), 2.34 (t, J=7.4 Hz, 2H), 1.55 (sextet, J=7.4 Hz, 2H), 0.82 (t, J=7.4 Hz, 3H).

ESI-MS $C_{18}H_{23}N_5O_2S$: 373.2, found: 374.2 $(M+H^+)^+$, 396.1 $(M+Na^+)^+$.

Example 63: 2-((2-(4-(2-ethoxyphenyl)piperazin-1-yl)-2-oxoethyl)thio)-6-isopropylpyrimidin-4(3H)-one (Compound 63)

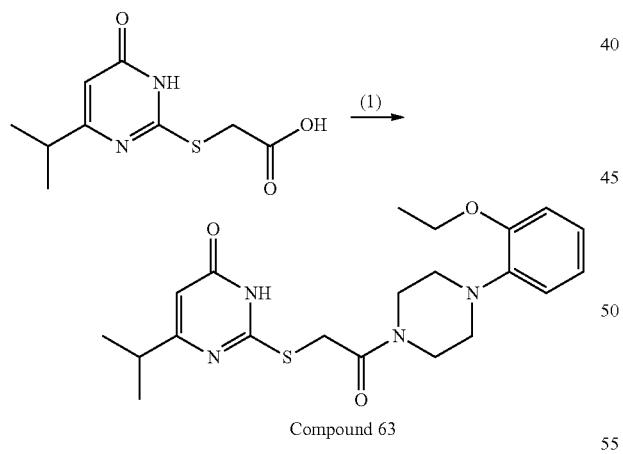

Compound 63

Reagents and conditions: 1-(2-ethoxy-phenyl)-piperazine, EDCI, DMAP, DMF, r.t., 16 h, and yield 59%.

(4-Isopropyl-6-oxo-1,6-dihydro-pyrimidin-2-ylsulfanyl)-acetic acid (100 mg, 0.44 mmol), 1-(2-ethoxy-phenyl)-piperazine (108.3 mg, 0.53 mmol), EDCI (100.8 mg, 0.53 mmol) and DMAP (16.1 mg, 0.13 mmol) were dissolved in 4 mL DMF, and then stirred at room temperature for 16 hours. After the solvent was removed, the reaction mixture was diluted with EtOAc, washed sequentially with water and brine. The organic layer was dried over $MgSO_4$, filtered and concentrated to afford a crude, which was purified by column chromatography (gradient elution: 5% to 10% MeOH in $CH_2Cl_2$) to give Compound 63 as a pale-yellow solid (107.3 mg, 59%).

$^1$H NMR (400 MHz, DMSO) δ 6.99-6.82 (m, 4H), 5.89 (s, 1H), 4.19 (s, 2H), 4.02 (q, J=7.0 Hz, 2H), 3.70 (t, J=5.1 Hz, 2H), 3.59 (t, J=5.1 Hz, 2H), 3.03 (t, J=5.1 Hz, 2H), 2.93 (t, J=5.1 Hz, 2H), 2.63 (septet, J=6.9 Hz, 1H), 1.35 (t, J=7.0 Hz, 3H), 1.11 (d, J=6.9 Hz, 6H).

ESI-MS $C_{21}H_{28}N_4O_3S$: 416.2, found: 417.1 $(M+H^+)^+$, 439.1 $(M+Na^+)^+$.

Example 64: 6-(3-chlorobenzyl)-2-(1-(4-(2,3-dimethylphenyl)piperazin-1-yl)ethyl)-5-methyl-[1,2,4]triazolo [1,5-a]pyrimidin-7(4H)-one (Compound 64)

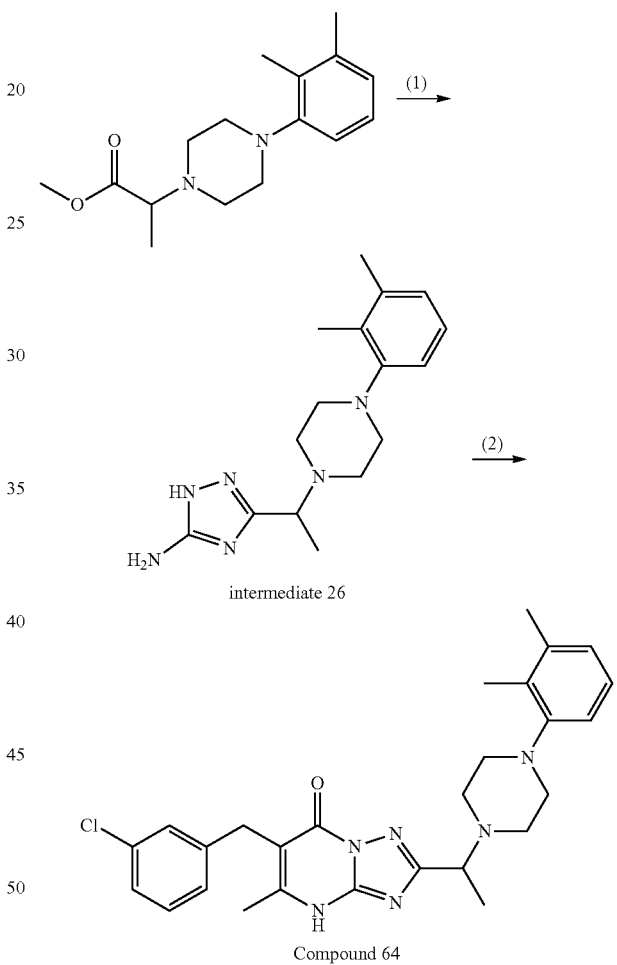

Compound 64

Reagents and conditions: (1) aminoguanidine bicarbonate, DMF, reflux, 16 h, and yield 7%; and (2) 2-(3-chlorobenzyl)-3-oxo-butyric acid ethyl ester, toluene, reflux by Dean-Stark, 16 h, and yield 38%.

Step 1

2-[4-(2,3-Dimethyl-phenyl)-piperazin-1-yl]-propionic acid methyl ester (1.6 g, 0.56 mmol), aminoguanidine bicarbonate (1.5 g, 1.12 mmol) were dissolved in 5 mL DMF and heated at reflux for 16 hours. After the solvent was removed, the reaction mixture was purified by column chromatography to give intermediate 26 as a white solid (120 mg, 7%).

$^1$H NMR (400 MHz, DMSO) δ 7.09-6.95 (m, 1H), 6.93-6.78 (m, 2H), 5.82 (s, 1H), 3.69-3.51 (m, 1H), 2.85-2.67 (m, 4H), 2.66-2.50 (m, 4H), 2.18 (s, 3H), 2.10 (s, 3H), 1.31 (d, J=6.1 Hz, 3H).

ESI-MS $C_{16}H_{24}N_6$: 300.2, found: 301.1 (M+H$^+$)$^+$, 323.1 (M+Na$^+$)$^+$.

Step 2

Intermediate 26 (120 mg, 0.39 mmol) and 2-(3-chlorobenzyl)-3-oxo-butyric acid ethyl ester (101.5 mg, 0.39 mmol) were dissolved in 5 mL toluene and heated at reflux by Dean-Stark for 16 hours. After the solvent was removed, the reaction mixture was purified by column chromatography to afford Compound 64 as a pale-yellow solid (74.3 mg, 38%).

$^1$H NMR (400 MHz, DMSO) δ 7.33-7.17 (m, 4H), 7.01 (t, J=7.7 Hz, 1H), 6.89-6.78 (m, 2H), 3.92 (q, J=7.0 Hz, 1H), 3.86 (s, 2H), 2.89-2.56 (m, 8H), 2.31 (s, 3H), 2.17 (s, 3H), 2.08 (s, 3H), 1.44 (d, J=7.0 Hz, 3H).

ESI-MS $C_{27}H_{31}ClN_6O$: 490.2, found: 491.1 (M+H$^+$)$^+$, 513.1 (M+Na$^+$)$^+$.

Example 65: 2-((2-(4-(3-methoxyphenyl)piperazin-1-yl)-2-oxoethyl)thio)-6-propylpyrimidin-4(3H)-one (Compound 65)

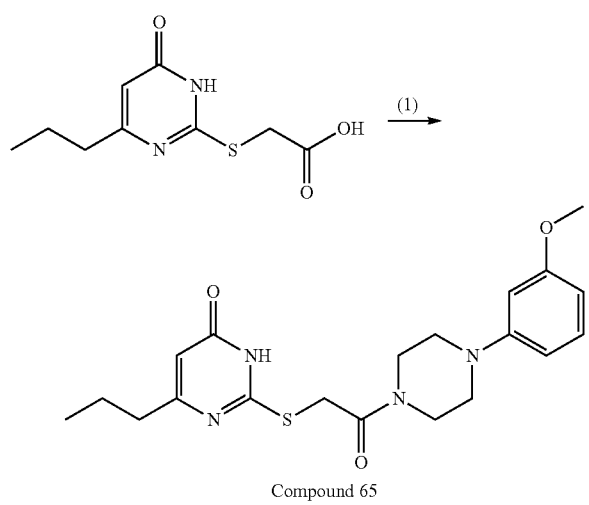

Compound 65

Reagents and conditions: 1-(3-methoxyl-phenyl)piperazine dihydrochloride, Et$_3$N, EDC, DMAP, DMF, r.t., 16 h, and yield 90%.

2-((6-Oxo-4-propyl-1,6-dihydropyrimidin-2-yl)thio)acetic acid (100 mg, 0.44 mmol), 1-(3-methoxyl-phenyl)piperazine dihydrochloride (128 mg, 0.48 mmol), Et$_3$N (0.01 ml), EDC (101 mg, 0.53 mmol) and DMAP (11 mg, 0.09 mmol) were dissolved in 2 mL DMF, and then stirred at room temperature for 16 hours. The reaction mixture was extracted with H$_2$O and CH$_2$Cl$_2$. The organic layer was dried over MgSO$_4$, filtered and concentrated to afford a crude, which was purified by column chromatography (10% MeOH in CH$_2$Cl$_2$ as eluent) to obtain Compound 65 as a white solid (158 mg, 90%).

$^1$H NMR (400 MHz, CDCl$_3$): δ 7.20 (t, J=8.5 Hz, 1H), 6.55 (d, J=8.5 Hz, 1H), 6.51-6.44 (m, 2H), 6.04 (s, 1H), 4.13 (s, 2H), 3.88-3.69 (m, 4H), 3.79 (s, 3H), 3.28-3.13 (m, 4H), 2.44 (t, J=7.4 Hz, 2H), 1.65 (sextet, J=7.4 Hz, 2H), 0.93 (t, J=7.4 Hz, 3H).

ESI-MS $C_{20}H_{26}N_4O_3S$: 402.2, found: 403.2 (M+H$^+$)$^+$, 425.1 (M+Na$^+$)$^+$.

Example 66: 2-((2-oxo-2-(4-(3-(trifluoromethyl)phenyl)piperazin-1-yl)ethyl)thio)-6-propylpyrimidin-4(3H)-one (Compound 66)

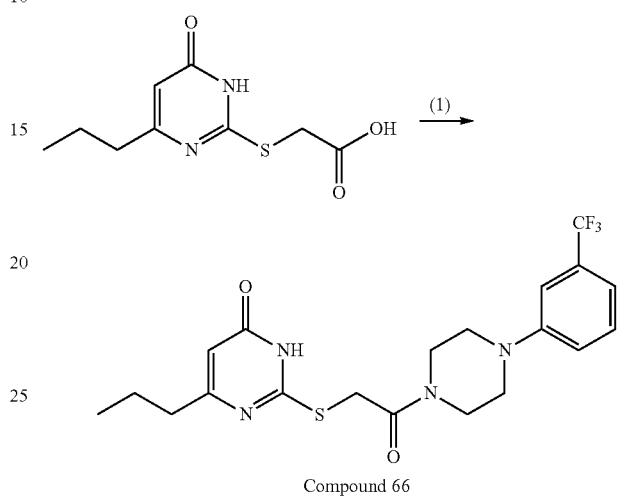

Compound 66

Reagents and conditions: 1-(3-trifloromethylphenyl)piperazine, EDC, DMAP, DMF, r.t., 16 h, and yield 89%.

2-((6-Oxo-4-propyl-1,6-dihydropyrimidin-2-yl)thio)acetic acid (100 mg, 0.44 mmol), 1-(3-trifloromethylphenyl)piperazine (0.09 ml, 0.48 mmol), EDC (101 mg, 0.53 mmol) and DMAP (11 mg, 0.09 mmol) were dissolved in 2 mL DMF, and then stirred at room temperature for 16 hours. The reaction mixture was extracted with H$_2$O and CH$_2$Cl$_2$. The organic layer was dried over MgSO$_4$, filtered and concentrated to afford a crude, which was purified by column chromatography (16% MeOH in CH$_2$Cl$_2$ as eluent) to obtain Compound 66 as a white solid (171 mg, 89%).

$^1$H NMR (400 MHz, CDCl$_3$): δ 7.38 (t, J=8.0 Hz, 1H), 7.18-7.10 (m, 2H), 7.10-7.04 (m, 1H), 6.04 (s, 1H), 4.14 (s, 2H), 3.83 (t, J=5.3 Hz, 2H), 3.76 (t, J=5.3 Hz, 2H), 3.29 (t, J=5.3 Hz, 2H), 3.24 (t, J=5.3 Hz, 2H), 2.44 (t, J=7.4 Hz, 2H), 1.65 (sextet, J=7.4 Hz, 2H), 0.93 (t, J=7.4 Hz, 3H).

ESI-MS $C_{20}H_{23}F_3N_4O_2S$: 440.2, found: 441.1 (M+H$^+$)$^+$, 463.1 (M+Na$^+$)$^+$.

Example 67: 2-((2-oxo-2-(4-(4-(trifluoromethyl)pyrimidin-2-yl)piperazin-1-yl)ethyl)thio)-6-propylpyrimidin-4(3H)-one (Compound 67)

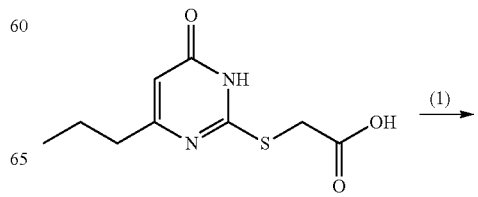

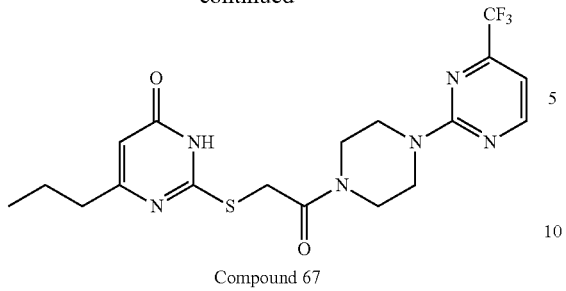

Compound 67

Reagents and conditions: 1-[4-(trifloromethyl)pyrimidin-2-yl]piperazine, EDC, DMAP, DMF, r.t., 16 h, yield 88%.

2-((6-Oxo-4-propyl-1,6-dihydropyrimidin-2-yl)thio)acetic acid (100 mg, 0.44 mmol), 1-[4-(trifloromethyl)pyrimidin-2-yl]piperazine (112 mg, 0.48 mmol), EDC (101 mg, 0.53 mmol) and DMAP (11 mg, 0.09 mmol) were dissolved in 2 mL DMF, and then stirred at room temperature for 16 hours. The reaction mixture was extracted with H$_2$O and CH$_2$Cl$_2$. The organic layer was dried over MgSO$_4$, filtered and concentrated to afford a crude, which was purified by column chromatography (10% MeOH in CH$_2$Cl$_2$ as eluent) to obtain Compound 67 as a white solid (171 mg, 88%).

$^1$H NMR (400 MHz, CDCl$_3$): δ 8.53 (d, J=4.8 Hz, 1H), 6.83 (d, J=4.8 Hz, 1H), 6.05 (d, J=0.7 Hz, 1H), 4.17 (s, 2H), 3.97 (t, J=5.4 Hz, 2H), 3.90 (t, J=5.4 Hz, 2H), 3.75 (t, J=5.4 Hz, 2H), 3.68 (t, J=5.4 Hz, 2H), 2.45 (t, J=7.4 Hz, 2H), 1.66 (sextet, J=7.4 Hz, 2H), 0.94 (t, J=7.4 Hz, 3H).

ESI-MS C$_{18}$H$_{21}$F$_3$N$_6$O$_2$S: 442.1, found: 443.1 (M+H$^+$)$^+$, 465.1 (M+Na$^+$)$^+$.

Example 68: 6-(3-chlorobenzyl)-5-methyl-2-(1-(4-(3-(trifluoromethyl)phenyl)-piperazin-1-yl)ethyl)-[1,2,4] triazolo[1,5-a]pyrimidin-7(4H)-one (Compound 68)

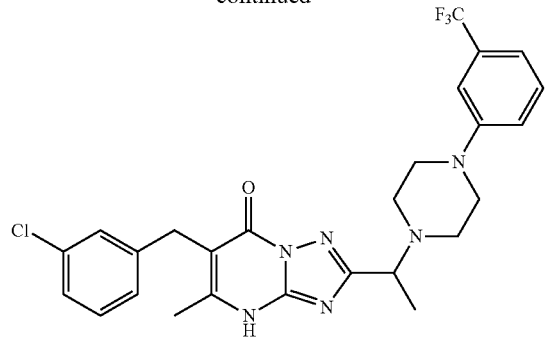

Compound 68

Reagents and conditions: (1) aminoguanidine bicarbonate, n-BuOH, reflux, 16 h, and yield 16%; and (2) 2-(3-chloro-benzyl)-3-oxo-butyric acid ethyl ester, AcOH, reflux, 16 h, and yield 8%.

2-[4-(3-Trifluoromethyl-phenyl)-piperazin-1-yl]-propionic acid methyl ester (800 mg, 2.53 mmol) and aminoguanidine bicarbonate (516.4 mg, 3.79 mmol) were dissolved in 5 mL n-BuOH and heated at reflux for 16 hours. After the solvent was removed, the reaction mixture was purified by column chromatography to give intermediate 27 as a white solid (135 mg, 16%).

$^1$H NMR (400 MHz, DMSO) δ 11.73 (s, 1H), 7.39 (t, J=8.1 Hz, 1H), 7.18 (d, J=8.1 Hz, 1H), 7.11 (s, 1H), 7.04 (d, J=8.1 Hz, 1H), 5.76 (s, 2H), 3.69-3.51 (m, 1H), 3.25-3.09 (m, 4H), 2.65-2.40 (m, 4H), 1.31 (d, J=7.0 Hz, 3H).

ESI-MS C$_{15}$H$_{19}$F$_3$N$_6$: 340.2, found: 341.1 (M+H$^+$)$^+$, 363.1 (M+Na$^+$)$^+$.

Step 2

Intermediate 27 (135 mg, 0.39 mmol) and 2-(3-chlorobenzyl)-3-oxo-butyric acid ethyl ester (100.7 mg, 0.39 mmol) were dissolved in 3 mL acetic acid and heated at reflux for 16 hours. After the solvent was removed, the reaction mixture was neutralized by saturated sodium bicarbonate solution and extracted by dicholoromethane. The organic layers were collected, dried over MgSO$_4$, filtered and concentrated to afford a crude, which was purified by column chromatography to afford Compound 68 as a pale-yellow solid (18.1 mg, 8%).

$^1$H NMR (400 MHz, DMSO) δ 7.38 (t, J=8.0 Hz, 1H), 7.30-7.14 (m, 5H), 7.10 (s, 1H), 7.03 (d, J=7.6 Hz, 1H), 3.91 (q, J=7.0 Hz, 1H), 3.85 (s, 2H), 3.23-3.12 (m, 4H), 2.73-2.55 (m, 4H), 2.29 (s, 3H), 1.44 (d, J=7.0 Hz, 3H).

ESI-MS C$_{26}$H$_{26}$ClF$_3$N$_6$O: 530.2, found: 531.1 (M+H$^+$)$^+$, 553.1 (M+Na$^+$)$^+$.

Example 69: 6-(3-chlorobenzyl)-2-(1-(4-(3,4-dichlorophenyl)piperazin-1-yl)ethyl)-5-methyl-[1,2,4]triazolo [1,5-a]pyrimidin-7(4H)-one (Compound 69)

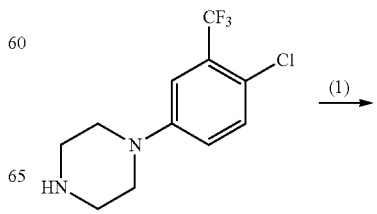

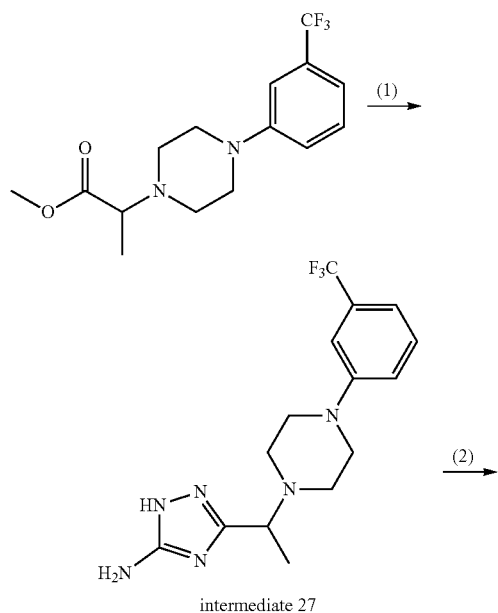

intermediate 27

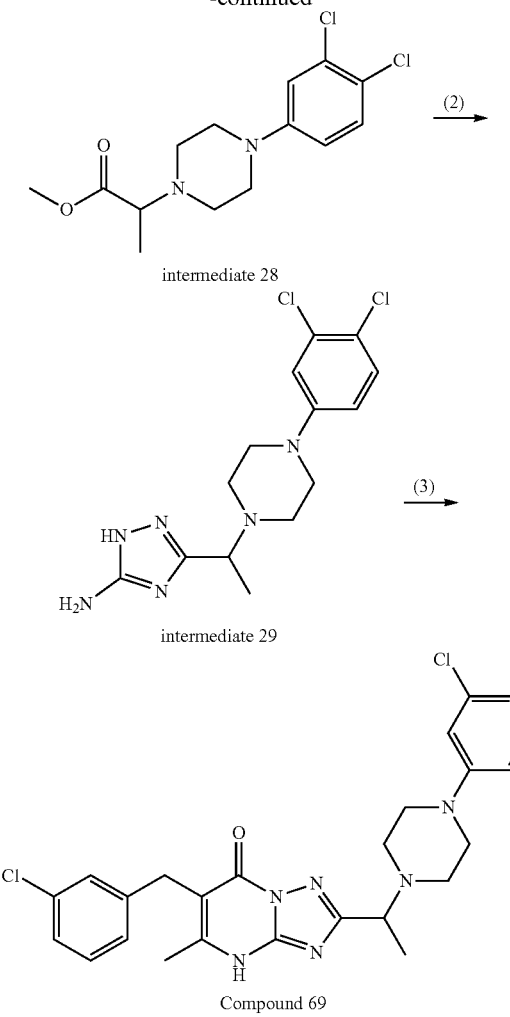

Reagents and conditions: (1) 2-bromo-propionic acid methyl ester, Et₃N, K₂CO₃, DMF, 60° C., 4 h, and yield 79%; (2) aminoguanidine bicarbonate, n-BuOH, reflux, 16 h, and yield 16%; and (3) 2-(3-chloro-benzyl)-3-oxo-butyric acid ethyl ester, AcOH, reflux, 16 h, and yield 13%.

Step 1

1-(3,4-Dichlorophenyl)piperazine (1 g, 0.43 mmol), 2-bromo-propionic acid methyl ester (1 mL, 0.86 mmol), triethyl amine (1.2 mL, 0.86 mmol) and K₂CO₃ (4.8 g, 3.47 mmol) were dissolved in 10 mL DMF and heated at 60° C. for 4 hours. After the solvent was removed, the reaction mixture was diluted with EtOAc, washed sequentially with water and brine. The organic layer was dried over MgSO₄, filtered and concentrated to afford a crude, which was purified by column chromatography (gradient elution: 1% to 5% EtOAc in hexane) to give intermediate 28 as a yellow oil (1.1 g, 79%).

$^1$H NMR (400 MHz, DMSO) δ 7.38 (d, J=9.0 Hz, 1H), 7.10 (d, J=2.9 Hz, 1H), 6.91 (dd, J=9.0, 2.9 Hz, 1H), 3.63 (s, 3H), 3.40 (q, J=7.0 Hz, 1H), 3.22-3.08 (m, 4H), 2.72-2.54 (m, 4H), 1.21 (d, J=7.0 Hz, 3H).

ESI-MS $C_{14}H_{18}Cl_2N_2O_2$: 316.1, found: 317.1 (M+H⁺)⁺.

Step 2

Intermediate 28 (1.1 g, 0.34 mmol) and aminoguanidine bicarbonate (0.7 g, 0.51 mmol) were dissolved in 5 mL n-BuOH and heated at reflux for 16 hours. After the solvent was removed, the reaction mixture was purified by column chromatography to give intermediate 29 as a white solid (182 mg, 16%).

$^1$H NMR (400 MHz, DMSO) δ 11.73 (s, 1H), 7.37 (d, J=9.0 Hz, 1H), 7.07 (d, J=2.7 Hz, 1H), 6.89 (dd, J=9.0, 2.7 Hz, 1H), 5.77 (s, 2H), 3.71-3.45 (m, 1H), 3.22-2.98 (m, 5H), 2.85-2.70 (m, 1H), 2.61-2.49 (m, 2H), 1.30 (d, J=6.9 Hz, 3H).

ESI-MS $C_{14}H_{18}Cl_2N_6$: 340.1, found: 341.0 (M+H⁺)⁺, 363.0 (M+Na⁺)⁺.

Step 3

Intermediate 29 (182 mg, 0.53 mmol) and 2-(3-chloro-benzyl)-3-oxo-butyric acid ethyl ester (135.5 mg, 0.53 mmol) were dissolved in 3 mL acetic acid and heated at reflux for 16 hours. After the solvent was removed, the reaction mixture was neutralized by saturated sodium bicarbonate solution and extracted by dicholoromethane. The organic layers were collected, dried over MgSO₄, filtered and concentrated to afford a crude, which was purified by column chromatography to afford Compound 69 as a pale-yellow solid (37.5 mg, 13%).

$^1$H NMR (400 MHz, DMSO) δ 7.35 (d, J=9.1 Hz, 1H), 7.31-7.16 (m, 4H), 7.06 (d, J=2.9 Hz, 1H), 6.88 (dd, J=9.1, 2.9 Hz, 1H), 3.90 (q, J=7.0 Hz, 1H), 3.85 (s, 2H), 3.21-3.07 (m, 4H), 2.70-2.55 (m, 4H), 2.29 (s, 3H), 1.43 (d, J=7.0 Hz, 3H).

ESI-MS $C_{25}H_{25}Cl_3N_6O$: 530.1, found: 531.0 (M+H⁺)⁺, 553.0 (M+Na⁺)⁺.

Example 70: 2-((2-(4-(4-methoxypyrimidin-2-yl)piperazin-1-yl)-2-oxoethyl)thio)-6-propylpyrimidin-4(3H)-one (Compound 70)

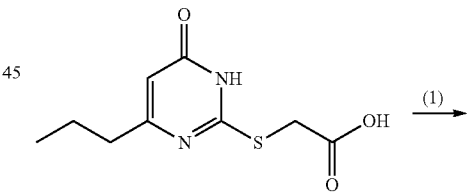

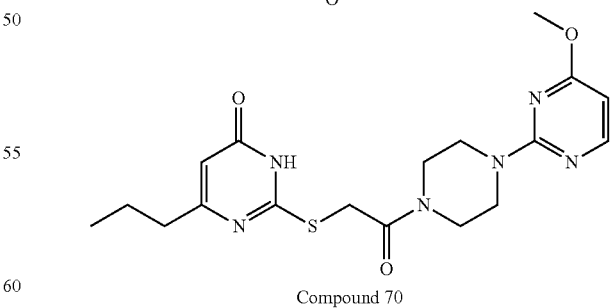

Compound 70

Reagents and conditions: 4-methoxy-2-(1-piperazino)pyrimidine, EDC, DMAP, DMF, r.t., 16 h, and yield 94%.

2-((6-Oxo-4-propyl-1,6-dihydropyrimidin-2-yl)thio)acetic acid (100 mg, 0.44 mmol), 4-methoxy-2-(1-piperazino) pyrimidine (94 mg, 0.48 mmol), EDC (101 mg, 0.53 mmol)

and DMAP (11 mg, 0.09 mmol) were dissolved in 2 mL DMF, and then stirred at room temperature for 16 hours. The reaction mixture was extracted with H$_2$O and CH$_2$Cl$_2$. The organic layer was dried over MgSO$_4$, filtered and concentrated to afford a crude, which was purified by column chromatography (10% MeOH in CH$_2$Cl$_2$ as eluent) to obtain Compound 70 as a white solid (167 mg, 94%).

$^1$H NMR (400 MHz, CDCl$_3$): δ 8.06 (d, J=5.7 Hz, 1H), 6.05 (d, J=5.7 Hz, 1H), 6.04 (s, 1H), 4.14 (s, 2H), 3.94-3.88 (m, 2H), 3.90 (s, 3H), 3.87-3.82 (m, 2H), 3.76-3.70 (m, 2H), 3.68-3.62 (m, 2H), 2.44 (t, J=7.4 Hz, 2H), 1.65 (h, J=7.4 Hz, 2H), 0.93 (t, J=7.4 Hz, 3H).

ESI-MS C$_{18}$H$_{24}$N$_6$O$_3$S: 404.2, found: 405.1 (M+H$^+$)$^+$, 427.1 (M+Na$^+$)$^+$.

Example 71: 2-((2-(4-(4-hydroxyphenyl)piperazin-1-yl)-2-oxoethyl)thio)-6-propylpyrimidin-4(3H)-one (Compound 71)

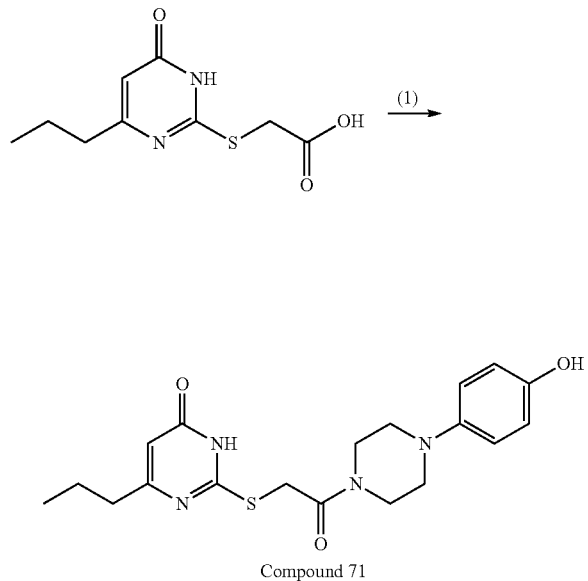

Compound 71

Reagents and conditions: 1-(4-hydroxyphenyl)piperazine, EDC, DMAP, DMF, r.t., 16 h, and yield 38%.

2-((6-Oxo-4-propyl-1,6-dihydropyrimidin-2-yl)thio)acetic acid (100 mg, 0.44 mmol), 1-(4-hydroxyphenyl)piperazine (86 mg, 0.48 mmol), EDC (101 mg, 0.53 mmol) and DMAP (11 mg, 0.09 mmol) were dissolved in 2 mL DMF, and then stirred at room temperature for 16 hours. The reaction mixture was extracted with H$_2$O and CH$_2$Cl$_2$. The organic layer was dried over MgSO$_4$, filtered and concentrated to afford a crude, which was purified by column chromatography (10% MeOH in CH$_2$Cl$_2$ as eluent) to obtain Compound 71 as a brown solid (65 mg, 38%).

$^1$H NMR (400 MHz, DMSO) δ 8.88 (s, 1H), 6.81 (d, J=8.8 Hz, 2H), 6.66 (d, J=8.8 Hz, 2H), 5.92 (s, 1H), 4.18 (s, 2H), 3.71-3.64 (m, 2H), 3.63-3.53 (m, 2H), 3.05-2.96 (m, 2H), 2.95-2.86 (m, 2H), 2.34 (t, J=7.4 Hz, 2H), 1.57 (sextet, J=7.4 Hz, 2H), 0.84 (t, J=7.4 Hz, 3H).

ESI-MS C$_{19}$H$_{24}$N$_4$O$_3$S: 388.2, found: 389.1 (M+H$^+$)$^+$, 411.1 (M+Na$^+$)$^+$.

Example 72: 2-((2-(4-(3-chloro-5-(trifluoromethyl)pyridin-2-yl)piperazin-1-yl)-2-oxoethyl)thio)-6-propyl pyrimidin-4(3H)-one (Compound 72)

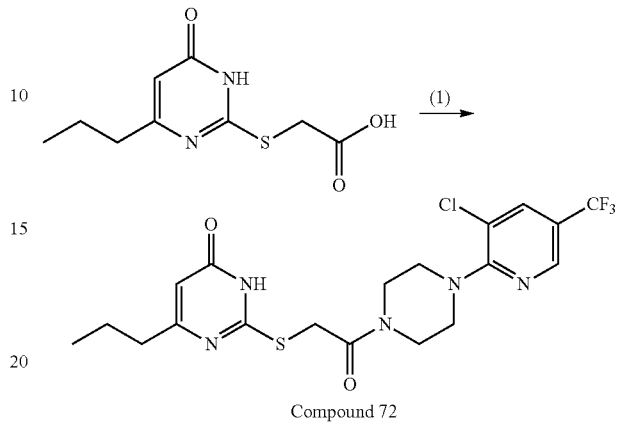

Compound 72

Reagents and conditions: 1-[3-choro-5-(trifloromethyl)pyrid-2-yl]piperazine, EDC, DMAP, DMF, r.t., 16 h, and yield 89%.

2-((6-Oxo-4-propyl-1,6-dihydropyrimidin-2-yl)thio)acetic acid (100 mg, 0.44 mmol), 1-[3-choro-5-(trifloromethyl)pyrid-2-yl]piperazine (128 mg, 0.48 mmol), EDC (101 mg, 0.53 mmol) and DMAP (11 mg, 0.09 mmol) were dissolved in 2 mL DMF, and then stirred at room temperature for 16 hours. The reaction mixture was extracted with H$_2$O and CH$_2$Cl$_2$. The organic layer was dried over MgSO$_4$, filtered and concentrated to afford a crude, which was purified by column chromatography (10% MeOH in CH$_2$Cl$_2$ as eluent) to obtain Compound 72 as a white solid (186 mg, 89%).

$^1$H NMR (400 MHz, CDCl$_3$): δ 8.41 (d, J=2.2 Hz, 1H), 7.80 (d, J=2.2 Hz, 1H), 6.05 (s, 1H), 4.15 (s, 2H), 3.83-3.70 (m, 4H), 3.59-3.46 (m, 4H), 2.46 (t, J=7.4 Hz, 2H), 1.67 (sextet, J=7.4 Hz, 2H), 0.95 (t, J=7.4 Hz, 3H).

ESI-MS C$_{19}$H$_{21}$ClF$_3$N$_5$O$_2$S: 475.1, found: 476.1 (M+H$^+$)$^+$, 498.1 (M+Na$^+$)$^+$.

PTGR2 Inhibiting Activity

Exemplary compounds thus prepared were evaluated for their efficacy in inhibiting PTGR2.

In vitro enzyme activity was measured to determine the half maximal inhibitory concentration (IC$_{50}$) of compounds of this invention as PTGR2 inhibitors. The reduction of 15-keto-PGE2 by PTGR2 requires NADPH. The decrease of NADPH during the reduction reaction indicates inhibition of PTGR2 and thus is used to calculate the IC$_{50}$ of a PTGR2 inhibitor. Human PTGR2 recombinant protein was mixed with a PTGR2 inhibitor (i.e., a compound of this invention) in a potassium phosphate buffer having a final concentration of 30 mM and a pH value of 7.3. The resultant mixture was pre-incubated at room temperature for 15 minutes. After the incubation, 15-keto-PGE2 was added to a final concentration of 20 μM, together with NADPH (20 μM, final concentration) and a Glo-NADPH reagent (commercially available from Promega Corporation, Madison, Wisconsin). After incubating at room temperature for 30 minutes, the signal by luminometer was recorded and used to calculate the IC$_{50}$ value of a PTGR2 inhibitor. See Table 2 below.

In a cell-based reporter assay, a compound of this invention was evaluated to determine its half maximal effective concentration (EC$_{50}$) as a PTGR2 inhibitor. HEK293T cells were seeded at 1×10⁵ cells/well in a 24-well plate. After allowing to grow for 24 hours, a DNA solution containing a UASG reporter construct, a GAL4-PPAR expression vector, a TK-Rluc (*Renilla luciferase*) reporter construct (internal control), and a human PTGR2-Tag expression vector (or a Tag expression vector as 100% inhibition) were transfected using a TurboFect™ transfection reagent (commercially available from Thermo Fisher, Waltham, Massachusetts). Cells were treated and harvested in two batches, one after 24 hours and another after 48 hours. The luciferase activity was measured by a Luc-Pair™ Duo-Luciferase HS Assay Kit (commercially available from Promega Corporation) and normalized to the TK-Rluc reporter signal, which was recorded and used to calculate the $EC_{50}$ value of a PTGR2 inhibitor. See Table 2 below.

TABLE 2

| Compound | IC$_{50}$ (nM) | EC$_{50}$ (nM) |
|---|---|---|
| 1 | 0.2 | 873.8 |
| 2 | 43 | 112.3 |
| 3 | 24.3 | 23.3 |
| 5 | 12.6 | 40.5 |
| 6 | 0.02 | 300.5 |
| 7 | 4.1 | 7 |
| 10 | 7.9 | 77.4 |
| 11 | 54.3 | 61.4 |
| 12 | 0.01 | 232.9 |
| 13 | 61.9 | 19.2 |
| 15 | 33.9 | 64.5 |
| 16 | 33.9 | 16.5 |
| 17 | 12 | 104.2 |
| 18 | 1.7 | 279.8 |
| 19 | 8.9 | 56.9 |
| 20 | 17.2 | 161.1 |
| 26 | 23.5 | 530.3 |
| 28 | 85 | 107.9 |
| 32 | 0.5 | 173.9 |
| 34 | 60.2 | 426.8 |
| 46 | 86.9 | 119.4 |
| 47 | 2.6 | 545.8 |
| 48 | 86.1 | 128.6 |
| 53 | 52.5 | 206.9 |
| 54 | 31.8 | 247.6 |
| 63 | 81.8 | 164.3 |

ITT and i.p.GTT Studies

Exemplary compounds were evaluated for their in vivo efficacy (i.p.GTT and ITT) in mice which were received exemplary compounds.

Figure 2:
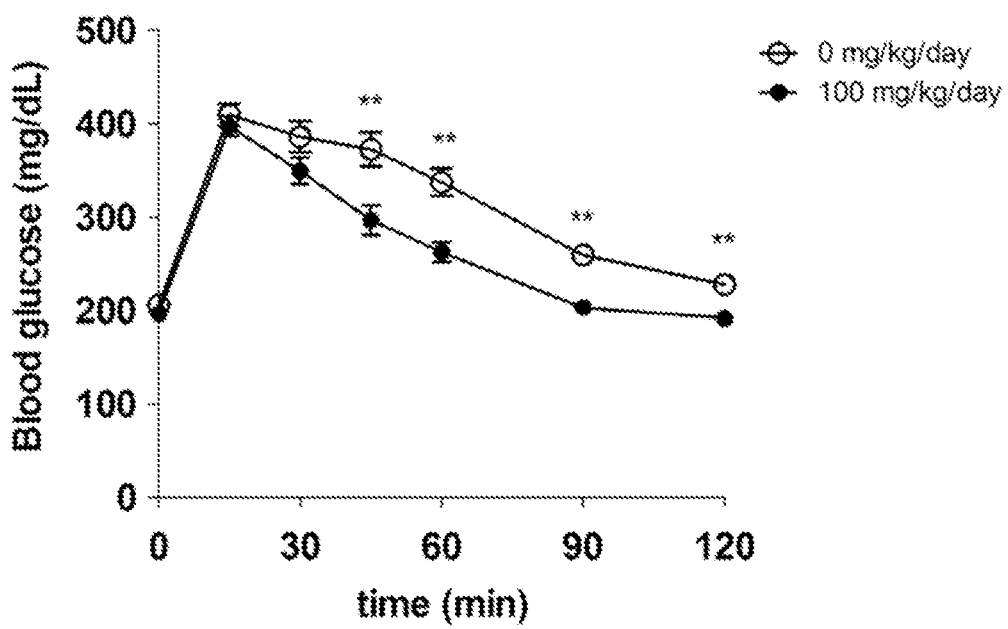
FIG. 2 shows animal blood glucose levels in a study of an intraperitoneal glucose tolerance test ("ipGTT"; glucose dose: 1 mg/kg), comparing two groups of mice treated with: (i) 100 mg/kg/day of compound 3 dissolved in an aqueous solution containing 3% dimethylacetamide and 10% cremophor and (ii) an aqueous solution containing 3% dimethylacetamide and 10% cremophor as a vehicle control.
Figure 4:
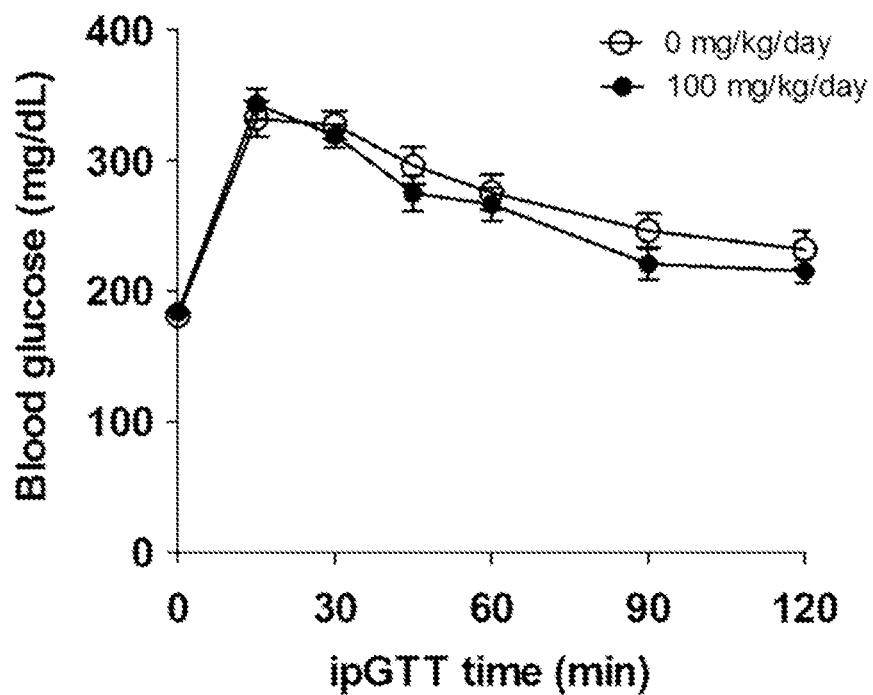
FIG. 4 shows animal blood glucose levels in an ipGTT (glucose dose: 1 mg/kg) study, comparing two groups of mice treated with: (i) 100 mg/kg/day of compound 7 dissolved in an aqueous solution containing 3% dimethylacetamide and 10% cremophor and (ii) an aqueous solution containing 3% dimethylacetamide and 10% cremophor as a vehicle control. No insulin is used.
Figure 6:
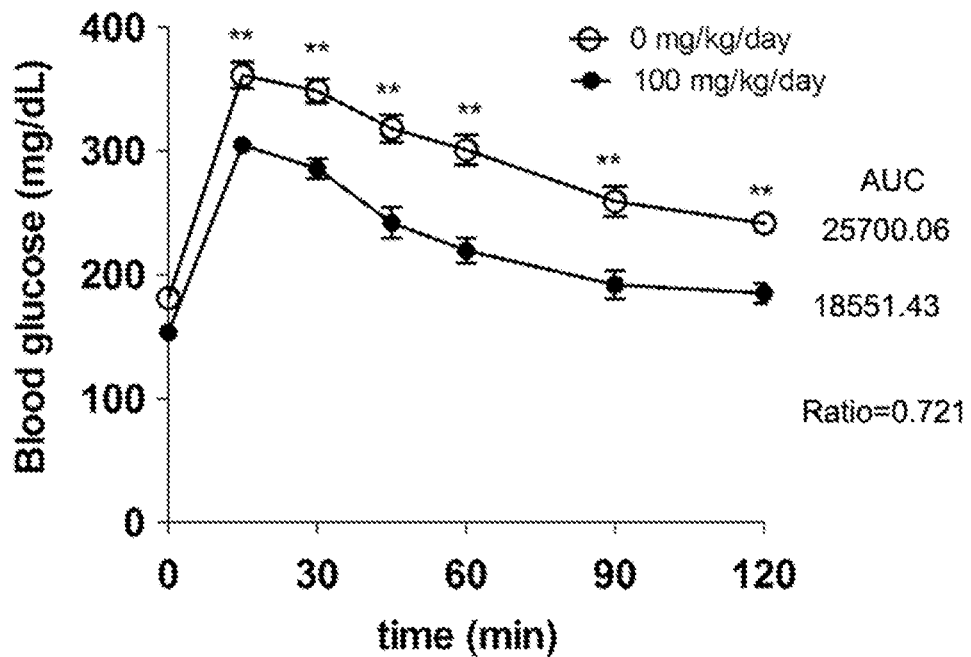
FIG. 6 shows animal blood glucose levels in an ipGTT study, comparing two groups of mice treated with: (i) 100 mg/kg/day of compound 19 dissolved in an aqueous solution containing 3% dimethylacetamide and 10% cremophor and (ii) an aqueous solution containing 3% dimethylacetamide and 10% cremophor as a vehicle control. No insulin is used.

Glucose tolerance was evaluated by the intraperitoneal glucose tolerance test (i.p.GTT) after a 6-hour fast. For the i.p.GTT, glucose water (1 mg/kg) was given by intraperitoneal (IP) injection and tail blood glucose was measured with a glucometer (ACCU-CHECK Performa, Roche Diabetes Care, Inc., Indianapolis, IN) at 0, 15, 30, 45, 60, 90, and 120 minutes. See FIGS. 2, 4, and 6.

Figure 3:
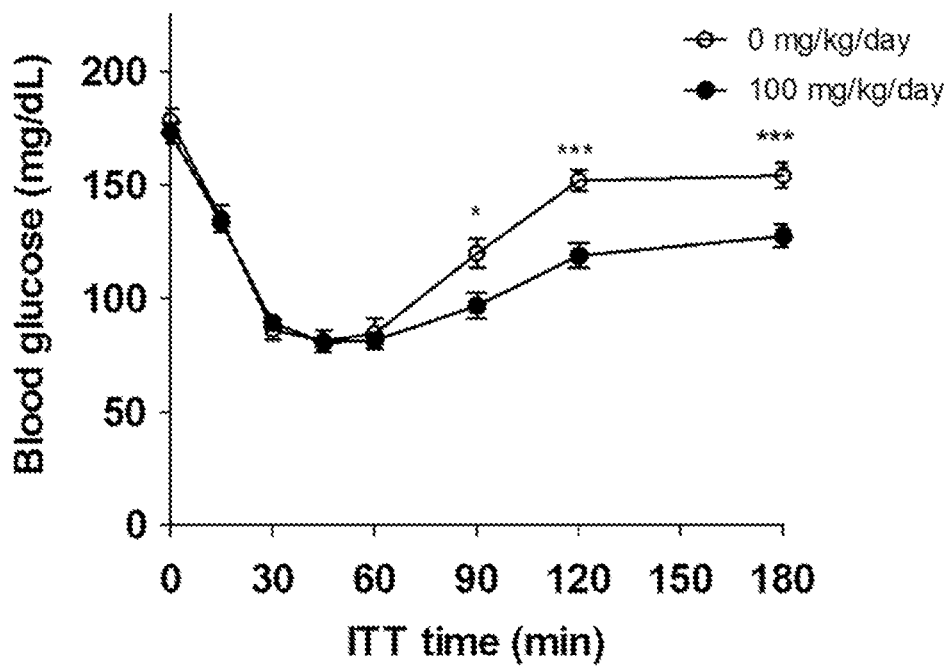
FIG. 3 shows animal blood glucose levels in an ITT (0.7 IU/kg of insulin) study, comparing two groups of mice treated with: (i) 100 mg/kg/day of compound 7 dissolved in an aqueous solution containing 3% dimethylacetamide and 10% cremophor and (ii) an aqueous solution containing 3% dimethylacetamide and 10% cremophor as a vehicle control.
Figure 5:
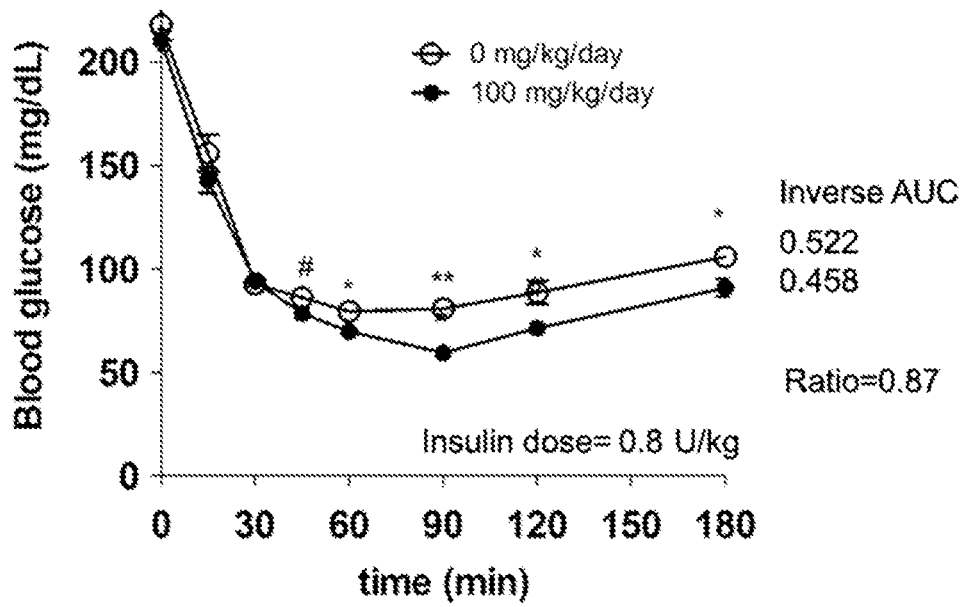
FIG. 5 shows animal blood glucose levels in an ITT (0.8 IU/kg of insulin) study, comparing two groups of mice treated with: (i) compound 19 dissolved in an aqueous solution containing 3% dimethylacetamide and 10% cremophor and (ii) an aqueous solution containing 3% dimethylacetamide and 10% cremophor as a vehicle control.

For the insulin tolerance test (ITT), mice were fasted for 4 hours and then injected intraperitoneally with 0.7-0.8 U/kg of insulin (Humulin R, Eli Lilly). Tail blood glucose was measured at 0, 15, 30, 45, 60, 90, 120, and 180 minutes. See FIGS. 1, 3, and 5.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:
1. A compound of formula (I):

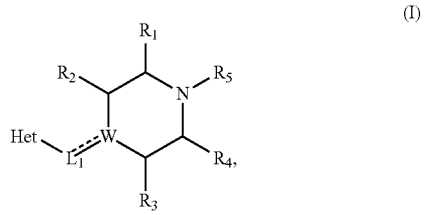

in which
each of $R_1$, $R_2$, $R_3$, and $R_4$, independently, is H, halo, $C_{1-6}$ alkyl, $C_{1-6}$ alkoxy, or $R_2$ and $R_4$ together is a $C_{1-6}$ alkyl;
$R_5$ is $C_{1-6}$ alkyl, $C_{3-10}$ cycloalkyl, $C_{1-10}$ heterocycloalkyl, aryl, heteroaryl, $C_{7-10}$ aralkyl, $C_{1-10}$ heteroaralkyl, $C(O)CH_2SR_6$, or $C(O)OR_7$, $R_6$ being $C_{1-10}$ heterocycloalkyl and $R_7$ being $C_{1-6}$ alkyl or $C_{7-10}$ aralkyl;
W is N or CH;
$L_1$ is $CH(CH_3)$;
Het is $C_{1-10}$ heterocyclyl;
--- is a single or double bond; and
each of $C_{1-6}$ alkyl, $C_{3-10}$ cycloalkyl, $C_{1-10}$ heterocycloalkyl, aryl, heteroaryl, $C_{7-10}$ aralkyl, $C_{1-10}$ heteroaralkyl, and heterocyclyl is optionally substituted with one or more of the chemical groups consisting of hydroxyl, halo, nitro, cyano, amino, $C_{1-6}$ alkyl, $C_{1-6}$ alkoxyl, $C_{3-10}$ cycloalkyl, aralkyl, and heteroaryl.

2. The compound of claim 1, wherein each of $R_1$, $R_2$, $R_3$, and $R_4$, independently, is H or methyl, or $R_2$ and $R_4$ together is methyl and each of $R_1$ and $R_3$ is H.

3. The compound of claim 1, wherein $R_5$ is phenyl, chlorophenyl, dichlorophenyl, fluorophenyl, difluorophenyl, hydroxylphenyl, methylphenyl, dimethylphenyl, trifluoromethylphenyl, methoxyphenyl, ethoxyphenyl, phenylmethoxy, benzyl, thiazolyl, benzo[d]isothiazolyl, pyridinyl, trifluoromethylpyridinyl, benzo[d][1,3]dioxolyl, pyrimidinyl, methoxypyrimidinyl, dimethoxypyrimidinyl, trifluoromethylpyrimidinyl, chlorotrifluoromethylpyridinyl, methoxyethyl, phenylethyl, or cyclohexyl.

4. The compound of claim 2, wherein each of $R_1$, $R_2$, $R_3$, and $R_4$ is H; and $R_5$ is phenyl.

5. The compound of claim 1, wherein W is N and --- is a single bond.

6. The compound of claim 1, wherein Het is

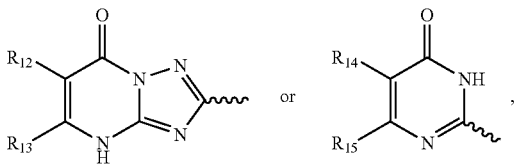

each of $R_{12}$, $R_{13}$, $R_{14}$, and $R_{15}$, independently, being hydroxyl, halo, nitro, cyano, amino, $C_{1-6}$ alkyl, $C_{1-6}$ alkoxyl, $C_{3-10}$ cycloalkyl, aralkyl, or heteroaryl.

7. The compound of claim 1, wherein Het is

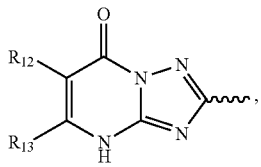

each of $R_{12}$ and $R_{13}$, independently, being halo, $C_{1-6}$ alkyl, $C_{1-6}$ alkoxyl, $C_{3-100}$ cycloalkyl, or aralkyl.

8. A compound selected from the group consisting of Compounds 1-72.

9. The compound of claim 6, wherein the compound is a compound of formula (II):

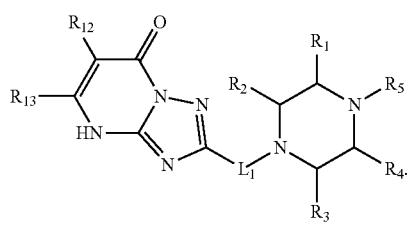

10. The compound of claim 9, wherein each of $R_1$, $R_2$, $R_3$, and $R_4$, independently, is H or methyl, or $R_2$ and $R_4$ together is methyl and each of $R_1$ and $R_3$ is H.

11. The compound of claim 9, wherein $R_5$ is phenyl, chlorophenyl, dichlorophenyl, fluorophenyl, difluorophenyl, hydroxylphenyl, methylphenyl, dimethylphenyl, trifluoromethylphenyl, methoxyphenyl, ethoxyphenyl, phenylmethoxy, benzyl, thiazolyl, benzo[d]isothiazolyl, pyridinyl, trifluoromethylpyridinyl, benzo[d][1,3]dioxolyl, pyrimidinyl, methoxypyrimidinyl, dimethoxypyrimidinyl, trifluoromethylpyrimidinyl, chlorotrifluoromethylpyridinyl, methoxyethyl, phenylethyl, or cyclohexyl.

12. The compound of claim 9, wherein each of $R_1$, $R_2$, $R_3$, and $R_4$ is H; and $R_5$ is phenyl.

13. The compound of claim 9, wherein $R_{12}$ is benzyl optionally substituted with one or more halo, and $R_{13}$ is methyl.

14. The compound of claim 9, wherein the compound is Compound 3, Compound 7, Compound 10, Compound 16, or Compound 19.

15. A compound of formula (III):

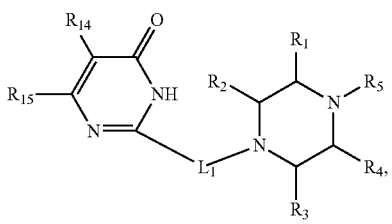

in which
each of $R_1$, $R_2$, $R_3$, and $R_4$, independently, is H, halo, $C_{1-6}$ alkyl, $C_{1-6}$ alkoxy, or $R_2$ and $R_4$ together is a $C_{1-6}$ alkyl;
$R_5$ is chlorophenyl, dichlorophenyl, fluorophenyl, difluorophenyl, hydroxylphenyl, methylphenyl, dimethylphenyl, trifluoromethylphenyl, methoxyphenyl, ethoxyphenyl, phenylmethoxy, benzyl, thiazolyl, benzo[d]isothiazolyl, pyridinyl, trifluoromethylpyridinyl, benzo[d][1,3]dioxolyl, pyrimidinyl, methoxypyrimidinyl, dimethoxypyrimidinyl, trifluoromethylpyrimidinyl, chlorotrifluoromethylpyridinyl, methoxyethyl, phenylethyl, or cyclohexyl;
$L_1$ is $SCH_2C(O)$, $SCH_2CH_2C(O)$, $NHCH_2C(O)$, $SCH(CH_3)C(O)$, $SCH(C_3H_7)C(O)$, or $SCH_2C(CH_3)_2C(O)$;
each of $R_{14}$ and $R_{15}$, independently, is hydroxyl, halo, nitro, cyano, amino, $C_{1-6}$ alkyl, $C_{1-6}$ alkoxyl, $C_{3-10}$ cycloalkyl, aralkyl, or heteroaryl; and
each of $C_{1-6}$ alkyl, $C_{3-10}$ cycloalkyl, heteroaryl, and aralkyl, is optionally substituted with one or more of the chemical groups consisting of hydroxyl, halo, nitro, cyano, amino, $C_{1-6}$ alkyl, $C_{1-6}$ alkoxyl, $C_{3-10}$ cycloalkyl, aralkyl, and heteroaryl.

16. The compound of claim 15, wherein each of $R_1$, $R_2$, $R_3$, and $R_4$ is H or methyl; and each of $R_{14}$ and $R_{15}$, independently, is H, $C_{1-6}$ alkyl, or $C_{3-10}$ cycloalkyl.

17. A method of inhibiting prostaglandin reductase 2 ("PTGR2"), the method comprising administering to a subject in need thereof an effective amount of a compound of claim 1.

18. A pharmaceutical composition comprising a compound of claim 1 and a pharmaceutically acceptable carrier.

19. A method of inhibiting prostaglandin reductase 2 ("PTGR2"), the method comprising administering to a subject in need thereof an effective amount of a compound of claim 8.

20. A pharmaceutical composition comprising a compound of claim 8 and a pharmaceutically acceptable carrier.

21. A method of inhibiting prostaglandin reductase 2 ("PTGR2"), the method comprising administering to a subject in need thereof an effective amount of a compound of claim 15.

22. A pharmaceutical composition comprising a compound of claim 15 and a pharmaceutically acceptable carrier.

* * * * *